US010542923B2

(12) United States Patent
Chang et al.

(10) Patent No.: US 10,542,923 B2
(45) Date of Patent: Jan. 28, 2020

(54) SYSTEM AND URINE SENSING DEVICES FOR AND METHOD OF MONITORING KIDNEY FUNCTION

(71) Applicant: THE JOHNS HOPKINS UNIVERSITY, Baltimore, MD (US)

(72) Inventors: Aaron Chang, Grand Prairie, TX (US); Sriram Chadalavada, Baltimore, MD (US); Madeleine Clegg, Baltimore, MD (US); Patience Osei, Baltimore, MD (US); Alexandra Sibole, Baltimore, MD (US); Nevin Katz, McLean, VA (US); Jonathan Trent Magruder, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 270 days.

(21) Appl. No.: 15/566,155

(22) PCT Filed: Apr. 15, 2016

(86) PCT No.: PCT/US2016/027674
§ 371 (c)(1),
(2) Date: Oct. 12, 2017

(87) PCT Pub. No.: WO2016/168541
PCT Pub. Date: Oct. 20, 2016

(65) Prior Publication Data
US 2018/0110455 A1 Apr. 26, 2018

Related U.S. Application Data

(60) Provisional application No. 62/147,940, filed on Apr. 15, 2015.

(51) Int. Cl.
*A61B 5/20* (2006.01)
*A61B 5/145* (2006.01)
(Continued)

(52) U.S. Cl.
CPC .............. *A61B 5/201* (2013.01); *A61B 5/207* (2013.01); *A61B 5/14507* (2013.01);
(Continued)

(58) Field of Classification Search
CPC ..... A61B 5/201; A61B 5/207; A61B 5/14507; A61B 5/743; A61B 5/208; A61B 2505/05; G01G 17/04; G01G 17/06
See application file for complete search history.

(56) References Cited

U.S. PATENT DOCUMENTS 4,602,693 A * 7/1986 Racicot ................. G01G 21/23
177/255
4,606,420 A 8/1986 Silver
(Continued)

FOREIGN PATENT DOCUMENTS

EP 0749685 A1 12/1996
EP 0679247 B1 4/1998
(Continued)

OTHER PUBLICATIONS

Extended European Search Report for EP16780799.9 dated Feb. 28, 2019, 11 pages.
(Continued)

*Primary Examiner* — Eric F Winakur
*Assistant Examiner* — Chu Chuan Liu
(74) *Attorney, Agent, or Firm* — Casimir Jones S.C.; Jeffrey W. Childers

(57) ABSTRACT

A system and urine sensing devices for and method of monitoring kidney function is disclosed, wherein the system and method can be used for the early detection of acute kidney injury (AKI). Namely, a kidney function monitoring system provides a portable urine monitor system that can provide real-time and continuous feedback about urine output and/or level of at least one urinary component (e.g.,
(Continued)

sodium). The kidney function monitoring system further comprises at least one urine sensing device, wherein the urine sensing device comprises a digital weight scale, a stand onto which a urine collection vessel can be positioned, and an interface between the digital weight scale and the stand that transfers the force of the stand and contents of the urine collection vessel to the digital weight scale. Further, the portable monitoring device comprises an adaptive and modular self-learning algorithm for the real-time assessment of AKI risk.

45 Claims, 44 Drawing Sheets

(51) Int. Cl.
*A61B 10/00* (2006.01)
*G01N 33/493* (2006.01)

(52) U.S. Cl.
CPC ......... *A61B 10/007* (2013.01); *A61B 2505/05* (2013.01); *G01N 33/493* (2013.01)

(56) References Cited

U.S. PATENT DOCUMENTS

| | | | |
|---|---|---|---|
| 5,571,964 A | 11/1996 | Sawada et al. | |
| 5,596,948 A * | 1/1997 | Ritchie | A01K 1/031 119/417 |
| 5,769,087 A | 6/1998 | Westphal et al. | |
| 5,776,077 A | 7/1998 | Kottig | |
| 6,021,339 A | 2/2000 | Saito et al. | |
| 6,998,543 B2 * | 2/2006 | Sugrue | G01G 19/005 177/126 |
| 7,736,354 B2 | 6/2010 | Gelfand et al. | |
| 8,006,400 B2 * | 8/2011 | Gerster | A61B 5/1072 33/512 |
| 8,663,128 B2 | 3/2014 | Paz et al. | |
| 8,827,924 B2 | 9/2014 | Paz et al. | |
| 2006/0253064 A1 | 11/2006 | Gelfand et al. | |
| 2008/0076970 A1 | 3/2008 | Foulis et al. | |
| 2011/0265576 A1 | 11/2011 | Cha et al. | |
| 2014/0073991 A1 | 3/2014 | Paz et al. | |

FOREIGN PATENT DOCUMENTS

| | | |
|---|---|---|
| EP | 2730215 A1 | 5/2014 |
| WO | 1999026447 A1 | 5/1999 |
| WO | 2007079942 A1 | 7/2007 |
| WO | 2009024985 A1 | 2/2009 |
| WO | 2011104710 A1 | 9/2011 |
| WO | 2011128890 A1 | 10/2011 |
| WO | 2013184868 A1 | 12/2013 |
| WO | 2014113558 A1 | 7/2014 |

OTHER PUBLICATIONS

Shahian, et al., The Society of Thoracic Surgeons 2008 cardiac surgery risk models: part 1—coronary artery bypass grafting surgery. Ann Thorac Surg 2009; 88: S2-22.

Shahian, et al., The society of thoracic surgeons national database. Heart 2013; 99: 1494-1501.

Prins, et al., Cardiac surgery risk-stratification models. Cardiovasc J Afr 2012; 23: 160-164.

Otero, et al., On the minute by minute variations of urine output: a study in a porcine model. J Nephrol 2014; 27: 45-50.

Hoste, et al., RIFLE criteria for acute kidney injury are associated with hospital mortality in critically ill patients: a cohort analysis. Crit Care 2006; 10: R73.

Rosner, et al., Acute kidney injury associated with cardiac surgery. Clinical journal of the American Society of Nephrology 2006; 1:19-32.

Okusa, et al., Physiological biomarkers of acute kidney injury: a conceptual approach to improving outcomes. Contrib Nephrol 2013; 182: 65-81.

Macedo, et al., Defining urine output criterion for acute kidney injury in critically ill patients. Nephrol Dial Transplant 2011; 26: 509-515.

Klein, et al., Minute-to-minute urine flow rate variability: a new renal physiology variable. Anesth Analg 2012; 115: 843-847.

Maciel, et al., Physicochemical analysis of blood and urine in the course of acute kidney injury in critically ill patients: a prospective, observational study. BMC Anethesiology 2013; 13: 31.

* cited by examiner

AKI risk GUI 124

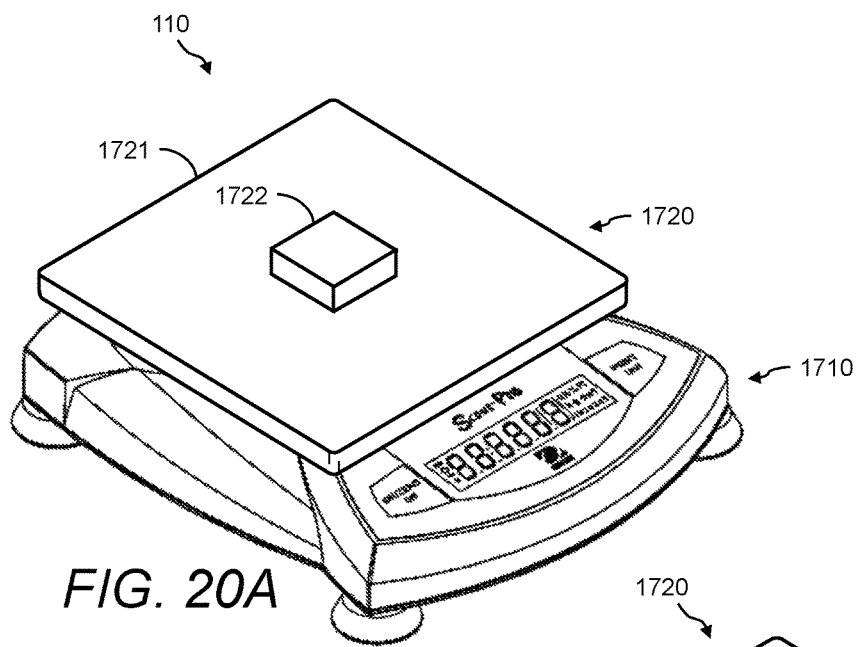
FIG. 20A
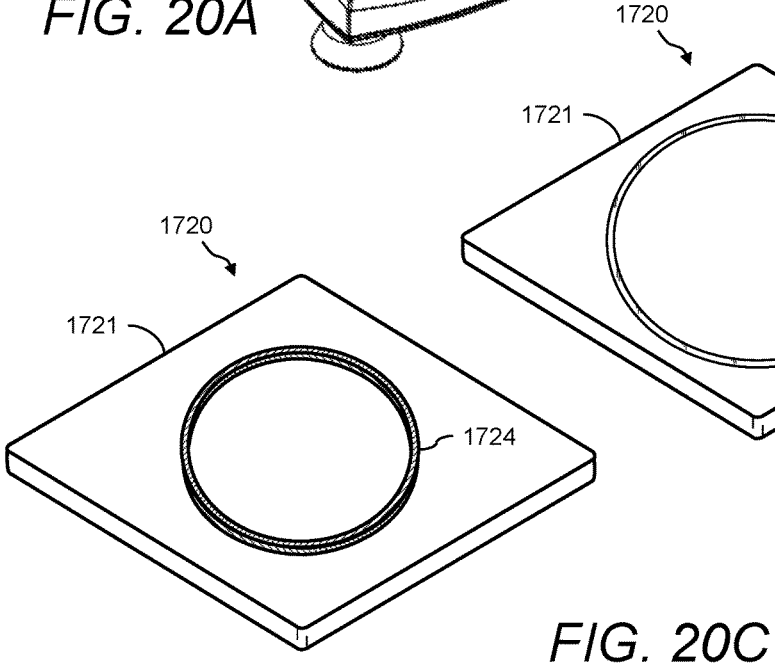
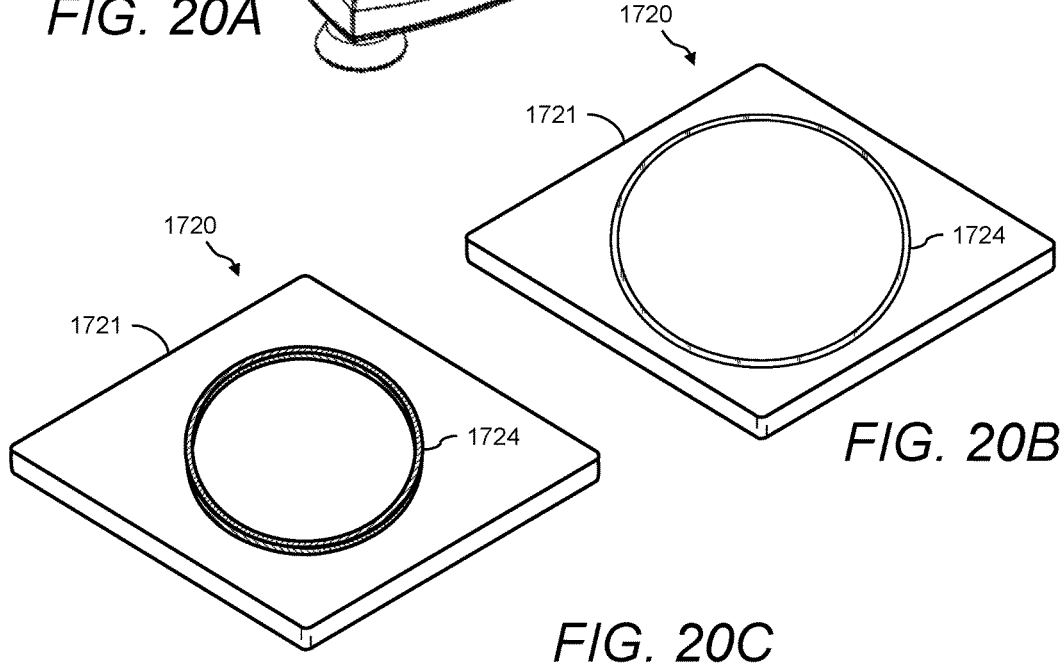
FIG. 20C
FIG. 20B

AKI risk GUI 124

AKI risk GUI 124

FIG. 38

AKI risk GUI 124

AKI risk GUI 124

SYSTEM AND URINE SENSING DEVICES FOR AND METHOD OF MONITORING KIDNEY FUNCTION

CROSS-REFERENCE TO RELATED APPLICATIONS

This application is a 35 U.S.C. § 371 National Stage Entry of International Application No. PCT/US2016/027674 having an international filing date of Apr. 15, 2016, which claims the benefit of U.S. Provisional Application No. 62/147,940, filed Apr. 15, 2015, the contents of which are incorporated herein by reference in its their entirety.

TECHNICAL FIELD

The presently disclosed subject matter relates generally to health monitoring systems and/or methods and more particularly to a system and urine sensing devices for and method of monitoring kidney function, wherein the system, urine sensing devices, and method can be used for the early detection of acute kidney injury (AKI).

BACKGROUND

Acute kidney injury (AKI) is a common event in cardiac surgery, with 5-30% of patients developing clinically significant AKI. AKI is a condition in which the kidneys become unable to adequately filter the blood, causing toxic levels of waste to accumulate throughout the body. AKI is formally defined as a greater than 50% decrease in glomerular filtration rate (GFR) over a period of hours to days, which leads to a decline in urine output over time. At present, measuring urine output is one of the most acceptable forms of assessing a patient for AKI, and is an important component of the established RIFLE criteria that assess kidney function.

In current clinical practice, Foley catheters are connected to urine collection vessels that are inscribed with volumetric scales. These are used by anesthesiologists intra-operatively and in the intensive care unit (ICU) to manually observe and measure urine output at certain time intervals. However, this method is subjective, and very rarely are measurements taken at frequent enough intervals for any incremental changes to be recorded. Bulk urine volume measurements are not reliable indicators of kidney function because these do not take into account the potential effects of medications and fluids that patients receive, or individual patient histories.

SUMMARY OF THE INVENTION

The practice of the present invention will typically employ, unless otherwise indicated, conventional techniques of cell biology, cell culture, molecular biology, transgenic biology, microbiology, recombinant nucleic acid (e.g., DNA) technology, immunology, and RNA interference (RNAi) which are within the skill of the art. Non-limiting descriptions of certain of these techniques are found in the following publications: Ausubel, F., et al., (eds.), *Current Protocols in Molecular Biology, Current Protocols in Immunology, Current Protocols in Protein Science*, and *Current Protocols in Cell Biology*, all John Wiley & Sons, N.Y., edition as of December 2008; Sambrook, Russell, and Sambrook, *Molecular Cloning. A Laboratory Manual*, $3^{rd}$ ed., Cold Spring Harbor Laboratory Press, Cold Spring Harbor, 2001; Harlow, E. and Lane, D., Antibodies—A Laboratory Manual, Cold Spring Harbor Laboratory Press, Cold Spring Harbor, 1988; Freshney, R. I., "Culture of Animal Cells, A Manual of Basic Technique", 5th ed., John Wiley & Sons, Hoboken, N.J., 2005. Non-limiting information regarding therapeutic agents and human diseases is found in Goodman and Gilman's The Pharmacological Basis of Therapeutics, 11th Ed., McGraw Hill, 2005, Katzung, B. (ed.) Basic and Clinical Pharmacology, McGraw-Hill/Appleton & Lange $10^{th}$ ed. (2006) or 11th edition (July 2009). Non-limiting information regarding genes and genetic disorders is found in McKusick, V. A.: Mendelian Inheritance in Man. A Catalog of Human Genes and Genetic Disorders. Baltimore: Johns Hopkins University Press, 1998 (12th edition) or the more recent online database: Online Mendelian Inheritance in Man, OMIM™. McKusick-Nathans Institute of Genetic Medicine, Johns Hopkins University (Baltimore, Md.) and National Center for Biotechnology Information, National Library of Medicine (Bethesda, Md.), as of May 1, 2010, World Wide Web URL: http://www.ncbi.nlm.nih.gov/omim/ and in Online Mendelian Inheritance in Animals (OMIA), a database of genes, inherited disorders and traits in animal species (other than human and mouse), at http://omia.angis.org.au/contact.shtml.

In one aspect, the presently disclosed subject matter provides a urine sensing device, the device comprising: (a) a weight scale comprising a platform; (b) a stand for positioning a urine collection vessel thereon, the stand comprising: (i) a base member, the base member comprising a first end, a second end, and an opening between the first end and second end; (ii) a first wall member extending radially from the first end of the base member, and angled at less than 90 degrees with respect to a horizontal axis of the base member, and (iii) a second wall member extending radially from the second end of the base member; and (c) an interface, for transferring the force of the stand and any contents thereon to the weight scale, positioned between the weight scale and the stand, the interface comprising: (i) a support member onto which the stand rests, (ii) a first alignment member atop the support member for interfacing with the stand via the opening, and (iii) a second alignment member underneath the support member for interfacing with the weight scale via the platform, wherein the first alignment member and the second alignment member are positioned such that the center of mass of the stand is aligned with respect to the center of mass of the weight scale.

In accordance with aspects of the disclosed subject matter, the first wall member comprises a first side aligned with a front face of the weight scale, and an opposite second side facing the second wall member, and wherein the first side of the first wall member further comprises a plurality of retaining members for securing a urinometer thereto in such a way as to prevent the urinometer from swinging from side-to-side.

In accordance with aspects of the disclosed subject matter, the second wall member further comprises a handle. In accordance with aspects of the disclosed subject matter, the second wall member has a height that is greater than the height of the first wall member. In accordance with aspects of the disclosed subject matter, the interface is constructed using a 3-D printer. In accordance with aspects of the disclosed subject matter, the first alignment member comprises a protuberance that extends through the opening of the base member and securely holds the stand in place on the interface. In accordance with aspects of the disclosed subject matter, the protuberance engages the base member on at least a portion of the perimeter of the opening. In accordance with aspects of the disclosed subject matter, the protuberance engages the base member on the entire perimeter of the opening. In accordance with aspects of the disclosed subject matter, the second alignment member comprises a groove in the support member that receives a perimeter of the platform, or wherein the second alignment member comprises a ridge on the support member that encloses perimeter of the platform.

In accordance with aspects of the disclosed subject matter, the urine sensing device further comprises a covering placed over the stand, the interface, and the weight scale, in such a way that at least a portion of the covering hangs over and in between the first wall member and the second wall member to create a pocket. In accordance with aspects of the disclosed subject matter, the urine sensing device includes a urine collection vessel positioned in the pocket. In accordance with aspects of the disclosed subject matter, the urine sensing device includes a urine collection vessel hanging from the second wall member such that it is positioned in between the first wall member and the second wall member. In accordance with aspects of the disclosed subject matter, the urine collection vessel in fluid communication with a urinometer that is secured to the first wall member.

In accordance with aspects of the disclosed subject matter, urine sensing device comprises a force transducer for converting the force transferred to the weight scale into to a digital output signal indicating the weight of the urine collected in the urine collection vessel. In accordance with aspects of the disclosed subject matter, the urine sensing device includes a communications interface for continuously transmitting in real-time the digital output signal from the urine sensing device to a portable monitoring device for real-time and continuous monitoring of urine output, and optionally at least one intra-operative risk factor indicative of acute kidney injury. In accordance with aspects of the disclosed subject matter, the portable monitoring device continuously monitors the urine output, and optionally monitors the at least one intra-operative risk factor indicative of acute kidney injury in real-time in second to second intervals or minute to minute intervals.

In another aspect, the presently disclosed subject matter provides a system for real-time and continuous monitoring of kidney function, comprising: (a) the urine sensing device, wherein the urine sensing device continuously monitors urine output flowing through a catheter of a catheterized patient into the urine collection vessel; and (b) a portable monitoring device for real-time and continuous assessment of kidney function based on a combination of real-time and continuous monitoring of urine output and volumetric flow rate based on second to second measurement of the weight of the urine collection vessel, and real-time and continuous monitoring of at least one intra-operative risk factor indicative of acute kidney injury.

In accordance with aspects of the disclosed subject matter, the catheter comprises a Foley catheter. In accordance with aspects of the disclosed subject matter, the system includes an external device selected from the group consisting of an anesthesia monitor, a perfusion pump, a heart-lung machine, a cerebral oximeter, an oxygenator, a patient monitor, or any combination thereof. In accordance with aspects of the disclosed subject matter, the anesthesia monitor or the patient monitor continuously monitors in real-time at least one of a mean arterial pressure of the catheterized patient, a medication administered to the catheterized patient, a fluid administered to the catheterized patient, and combinations thereof. In accordance with aspects of the disclosed subject matter, the portable monitoring device comprises: (i) a communications interface for automatically receiving real-time urine output continuously transmitted via the communications interface of the urine sensing device, optionally real-time levels of at least one urinary component, and real-time input comprising the at least one intra-operative risk factor indicative of acute kidney injury continuously transmitted from the external device via the communications interface of (i); (ii) a non-transitory computer readable storage medium having computer readable program code embodied thereon for executing an acute kidney injury risk algorithm that calculates the catheterized patient's risk of developing acute kidney injury as a percentage of the likelihood that the catheterized patient will develop acute kidney injury; and (iii) a graphical user interface comprising: (1) means for prompting a user to input pre-operative patient information, and (2) a display for graphically displaying the percentage of the likelihood that the catheterized patient will develop acute kidney injury.

In accordance with aspects of the disclosed subject matter, the pre-operative patient information is selected from group the consisting of a pre-operative Society of Thoracic Surgeons Risk Factor, pre-operative baseline urine density, pre-operative patient weight, and combinations thereof. In accordance with aspects of the disclosed subject matter, the display graphically displays at least one of real-time second to second urine output, real-time levels of the at least one urinary component, real-time input comprising the at least one intra-operative risk factor indicative of acute kidney injury, real-time second to second fluctuations in urine output, real-time second to second fluctuations in levels of the at least one urinary component, real-time second to second changes in the at least one intra-operative risk factor indicative of acute kidney injury, a plot of urine weight over time, an AKI risk score in the form of a percentage, alert color, literary instruction, and combinations thereof.

In accordance with aspects of the disclosed subject matter, the acute kidney injury risk algorithm calculates the catheterized patient's risk of developing acute kidney injury based on a weighting of acute kidney injury risk factors selected from the group consisting of the pre-operative Society of Thoracic Surgeon Risk Factors; KDIGO, RIFLE, and/or AKIN risk stratification Criteria for Urine Output; KDIGO/AKIN Criteria for Serum Creatinine; volumetric flow rate calculations based on baseline urine density, pre-operative patient weight, and real-time second to second fluctuations in weight of the urine collection vessel; real-time urine output adjusted for changes due to medication and/or fluid administered to the catheterized patient; real-time levels of the at least one urinary component adjusted for changes due to medication and/or fluid administered to the catheterized patient; and real-time input comprising changes in the at least one intra-operative risk factor indicative of acute kidney injury.

In accordance with aspects of the disclosed subject matter, the pre-operative Society of Thoracic Surgeon Risk Factors are selected from the group consisting of: the planned, unplanned, complicated, or unexpected nature of a Coronary Artery Bypass operation; whether or not a valve is being altered in the surgery; whether or not another cardiac procedure is indicated; if the patient is admitted with a ventricular assist device (VAD); if a VAD is implanted during current hospitalization; if an aortic procedure is to be performed; if an atrial fibrillation procedure is performed; if the current case is canceled; if there are other non-cardiac related operations; patient age, gender, height, and weight; if hemodynamic data such as ejection fraction is done; if a patient had experienced heart failure within 2 weeks; patient race, if the patient is Hispanic, Latino, or Spanish Ethnicity;

if the patient is in renal failure or on dialysis; the patient's last creatinine level; the occurrence of a cardiac symptoms at time of current admission selected from the group consisting of stable angina, unstable angina, angina equivalent, non-ST Elevation myocardial infarction, ST Elevation myocardial infarction, and combinations thereof; the occurrence of a cardiac symptoms at time of surgery selected from the group consisting of stable angina, unstable angina, angina equivalent, non-ST Elevation myocardial infarction, ST Elevation myocardial infarction, and combinations thereof; if a prior myocardial infarction existed; if cardiac arrhythmia is present; if patient has chronic lung disease; if patient has cerebrovascular disease; if peripheral arterial disease is present; if patient has diabetes; if hypertension is present; whether or not the patient is immunocompromised; if endocarditis is present; if coronary disease exists; the nature of the surgery; if the patient has been resuscitated within one hour of the start of the procedure; if the patient has been resuscitated between 1 and 24 hours from the start of the procedure; if the patient is experiencing cardiogenic shock; if patient has an intra-aortic balloon pump installed; if patient is on inotropes; if patient has had a previous cardiac intervention; if mitral valve or aortic disease is present, the degree of mitral valve insufficiency, the degree of tricuspid insufficiency; the degree of aortic insufficiency, and the incidence of current cardiovascular surgery, and combinations thereof.

In accordance with aspects of the disclosed subject matter, the KDIGO Criteria for Urine Output is selected from the group consisting of stratification of acute kidney injury in increasing severity stages wherein said stages are defined as the following: stage 1 is defined as <0.5 ml/kg/h for 6-12 hours, stage 2 is defined as <0.5 ml/kg/h for >12 hours, and stage three is defined as <0.3 ml/kg/h for more than 24 hours, or anuria for more than 12 hours, and combinations thereof, and/or wherein the KDIGO/AKIN Criteria for Serum Creatinine is selected from the group consisting of stratification of acute kidney injury in increasing severity stages wherein said stages are defined as the following: stage 1 is defined as a 50%-99% increase in serum creatinine from baseline, or an acute increase of 0.3 mg/dL or more from baseline, stage 2 is defined as a 100%-199% increase in serum creatinine from baseline, and stage 3 is defined as a 200% or greater increase in serum creatinine from baseline, or any new need for hemodialysis.

In accordance with aspects of the disclosed subject matter, the at least one urinary component is selected from the group consisting of urine sodium levels, urine oxygen tension levels, urine creatinine levels, urine potassium levels, and urine chloride levels. In accordance with aspects of the disclosed subject matter, the at least one intra-operative risk factor indicative of acute kidney injury is selected from the group consisting of a real-time cerebral oximetry autoregulation threshold, nadir oxygen delivery, oxygen tension, mean arterial blood pressure, vasopressor dosage, diuretic delivery, fluid delivery, and combinations thereof. In accordance with aspects of the disclosed subject matter, the acute kidney injury risk algorithm comprises a self-learning algorithm that adjusts the weighting of the acute kidney injury risk factors for each catheterized patient based on the relative significance of the acute kidney injury risk factors toward influencing outcomes of other catheterized patients presenting with similar acute kidney injury risk factors.

In accordance with aspects of the disclosed subject matter, the system includes a patient database in electronic communication with the portable monitoring device, wherein the patient database comprises for each catheterized patient, the calculation of the patient's acute kidney injury risk, the acute kidney injury risk factors present in the patient, the weighting of the patient's acute kidney injury risk factors, and an indication of whether the patient developed acute kidney injury.

In accordance with aspects of the disclosed subject matter, the system includes a function for filtering the digital output signal.

In yet another aspect, the presently disclosed subject matter provides a method for real-time assessment of a patient's risk of developing acute kidney injury, the method comprising: (a) connecting a catheter of a catheterized patient to a urine collection vessel positioned on a urine sensing device, wherein the urine sensing device measures second-to-second urine output; (b) continuously monitoring urine output of said catheterized patient by measuring real-time second to second fluctuations in urine output with the urine sensing device; (c) transmitting the continuously monitored real-time fluctuations in urine output measured in (b) to a patient monitoring device, wherein the patient monitoring device comprises: (i) a communications interface for automatically receiving the continuously monitored real-time fluctuations transmitted in (c); (ii) a non-transitory computer readable storage medium having computer readable program code embodied thereon for executing an acute kidney injury risk algorithm that calculates the catheterized patient's risk of developing acute kidney injury as a percentage of the likelihood that the catheterized patient will develop acute kidney injury; and (iii) a graphical user interface comprising means for prompting a user to input pre-operative patient information; (e) calculating the catheterized patient's risk of developing acute kidney injury as a percentage of the likelihood that the catheterized patient will develop acute kidney injury; and (f) displaying through the graphical user interface the catheterized patient's risk of developing acute kidney injury as a percentage of the likelihood that the catheterized patient will develop acute kidney injury.

In accordance with aspects of the disclosed subject matter, the method includes continuously transmitting via a communications interface the digital output signal from the urine sensing device to the portable monitoring device. In accordance with aspects of the disclosed subject matter, the method includes continuously monitoring at least one intra-operative risk factor indicative of acute kidney injury by measuring real-time second to second changes in the at least one intra-operative risk factor indicative of acute kidney injury using an external device. In accordance with aspects of the disclosed subject matter, the external device is selected from the group consisting of an anesthesia monitor, a perfusion pump, a heart-lung machine, a cerebral oximeter, an oxygenator, a patient monitor, and combinations thereof.

In accordance with aspects of the disclosed subject matter, the method includes automatically receiving, via the communications interface, the measured real-time second to second changes in the at least one intra-operative risk factor indicative of acute kidney injury. In accordance with aspects of the disclosed subject matter, the pre-operative patient information is selected from group the consisting of a pre-operative Society of Thoracic Surgeons Risk Factor, pre-operative baseline urine density, pre-operative patient weight, and combinations thereof.

In accordance with aspects of the disclosed subject matter, the method includes displaying at least one of real-time second to second urine output, real-time levels of the at least one urinary component, real-time input comprising the at least one intra-operative risk factor indicative of acute kidney injury, real-time second to second fluctuations in urine output, real-time second to second fluctuations in levels of the at least one urinary component, real-time second to second changes in the at least one intra-operative risk factor indicative of acute kidney injury, a plot of urine weight over time, an AKI risk score in the form of a numerical percentage, alert color, or literary instruction, and combinations thereof.

In accordance with aspects of the disclosed subject matter, the acute kidney injury risk algorithm calculates the catheterized patient's risk of developing acute kidney injury based on a weighting of acute kidney injury risk factors selected from the group consisting of the pre-operative Society of Thoracic Surgeon Risk Factors; KDIGO Criteria for Urine Output; KDIGO/AKIN Criteria for Serum Creatinine; volumetric flow rate calculations based on baseline urine density, pre-operative patient weight, and real-time second to second fluctuations in weight of the urine collection vessel; real-time urine output adjusted for changes due to medication and/or fluid administered to the catheterized patient; optionally real-time levels of the at least one urinary component adjusted for changes due to medication and/or fluid administered to the catheterized patient; and real-time changes in the at least one intra-operative risk factor indicative of acute kidney injury. In accordance with aspects of the disclosed subject matter, the pre-operative Society of Thoracic Surgeon Risk Factors are selected from the group consisting of: the planned, unplanned, complicated, or unexpected nature of a Coronary Artery Bypass operation; whether or not a valve is being altered in the surgery; whether or not another cardiac procedure is indicated; if the patient is admitted with a ventricular assist device (VAD); if a VAD is implanted during current hospitalization; if an aortic procedure is to be performed; if an atrial fibrillation procedure is performed; if the current case is canceled; if there are other non-cardiac related operations; patient age, gender, height, and weight; if hemodynamic data such as ejection fraction is done; if a patient had experienced heart failure within 2 weeks; patient race, if the patient is Hispanic, Latino, or Spanish Ethnicity; if the patient is in renal failure or on dialysis; the patient's last creatinine level; the occurrence of a cardiac symptoms at time of current admission selected from the group consisting of stable angina, unstable angina, angina equivalent, non-ST Elevation myocardial infarction, ST Elevation myocardial infarction, and combinations thereof; the occurrence of a cardiac symptoms at time of surgery selected from the group consisting of stable angina, unstable angina, angina equivalent, non-ST Elevation myocardial infarction, ST Elevation myocardial infarction, and combinations thereof; if a prior myocardial infarction existed; if cardiac arrhythmia is present; if patient has chronic lung disease; if patient has cerebrovascular disease; if peripheral arterial disease is present; if patient has diabetes; if hypertension is present; whether or not the patient is immunocompromised; if endocarditis is present; if coronary disease exists; the nature of the surgery; if the patient has been resuscitated within one hour of the start of the procedure; if the patient has been resuscitated between 1 and 24 hours from the start of the procedure; if the patient is experiencing cardiogenic shock; if patient has an intra-aortic balloon pump installed; if patient is on inotropes; if patient has had a previous cardiac intervention; if mitral valve or aortic disease is present, the degree of mitral valve insufficiency, the degree of tricuspid insufficiency; the degree of aortic insufficiency, and the incidence of current cardiovascular surgery, and combinations thereof.

In accordance with aspects of the disclosed subject matter, the KDIGO Criteria for Urine Output is selected from the group consisting of stratification of acute kidney injury in increasing severity stages wherein said stages are defined as the following: stage 1 is defined as <0.5 ml/kg/h for 6-12 hours, stage 2 is defined as <0.5 ml/kg/h for >12 hours, and stage three is defined as <0.3 ml/kg/h for more than 24 hours, or anuria for more than 12 hours, and combinations thereof, and/or wherein the KDIGO/AKIN Criteria for Serum Creatinine is selected from the group consisting of stratification of acute kidney injury in increasing severity stages wherein said stages are defined as the following: stage 1 is defined as a 50%-99% increase in serum creatinine from baseline, or an acute increase of 0.3 mg/dL or more from baseline, stage 2 is defined as a 100%-199% increase in serum creatinine from baseline, and stage 3 is defined as a 200% or greater increase in serum creatinine from baseline, or any new need for hemodialysis.

In accordance with aspects of the disclosed subject matter, the at least one urinary component is selected from the group consisting of urine sodium levels, urine oxygen tension levels, urine creatinine levels, urine potassium levels, and urine chloride levels.

In accordance with aspects of the disclosed subject matter, the at least one intra-operative risk factor indicative of acute kidney injury is selected from the group consisting of a real-time cerebral oximetry autoregulation threshold, nadir oxygen delivery, oxygen tension, mean arterial blood pressure, and combinations thereof.

In accordance with aspects of the disclosed subject matter, the method includes adjusting the weighting of the acute kidney injury risk factors for each catheterized patient via the acute kidney injury risk algorithm based on the relative significance of the acute kidney injury risk factors toward influencing outcomes of other catheterized patients presenting with similar acute kidney injury risk factors.

In accordance with aspects of the disclosed subject matter, the method includes storing in a patient database in communication with the portable monitoring device, for each catheterized patient, the calculation of the patient's acute kidney injury risk, the acute kidney injury risk factors for the patient, the weighting of the patient's acute kidney injury risk factors, and an indication of whether the patient developed acute kidney injury.

In accordance with aspects of the disclosed subject matter, the method performs a function for filtering the digital output signal.

In one aspect, the presently disclosed subject matter provides a urine sensing device, the device comprising: (a) a base member comprising a housing having a weight scale disposed therein; (b) a compression member for transferring a force to the weight scale, the compression member comprising a first end mechanically coupled to the weight scale, a second end outside the housing opposite the first end, and a central portion extending longitudinally from the first end to the second end; and (c) a first hook extending radially and upwardly from the second end of the compression member for hanging a urine collection vessel thereon, wherein the force of the weight of the urine collection vessel hanging on the first hook is transferred to the weight scale in the base member via the compression member.

In accordance with aspects of the disclosed subject matter, the base member further includes a force transducer disposed inside the housing for converting the force transferred to the weight scale into to a digital output signal indicating the weight of the urine collection vessel. In accordance with aspects of the disclosed subject matter, the urine sensing device includes a communications interface for continuously transmitting in real-time the digital output signal from the urine sensing device to a portable monitoring device for real-time and continuous monitoring of urine output, a level of at least one urinary component, and at least one intra-operative risk factor indicative of acute kidney injury.

In another aspect, the presently disclosed subject matter provides a urine sensing device, the device comprising: (a) a weight scale, (b) an interface, and (c) a stand, wherein a Foley bag and urinometer can be installed in/on the stand.

In accordance with aspects of the disclosed subject matter, the portable monitoring device continuously monitors the urine output, optionally the level of the at least one urinary component, and/or at least one intra-operative risk factor indicative of acute kidney injury in real-time in second to second intervals or minute to minute intervals. In accordance with aspects of the disclosed subject matter, the base member further comprises at least one ionic species sensor disposed inside the housing for measuring the level of the at least one urinary component. In accordance with aspects of the disclosed subject matter, the at least one urinary component is selected from the group consisting of urine sodium, urine oxygen tension, urine creatinine, urine potassium, and urine chloride. In accordance with aspects of the disclosed subject matter, the base member further includes a tube positioned near a perimeter of the base member, wherein the tube projects outwardly away from and extends inwardly into the base member along a longitudinal axis that is perpendicular to a horizontal plane of the base member, and wherein the tube comprises a channel through which a volume of urine in fluid communication with the urine collection vessel flows along the longitudinal axis into a chamber inside the base member. In accordance with aspects of the disclosed subject matter, the volume of urine comprises a metered volume of urine that flows into the chamber at a predetermined volume and at predetermined time intervals. In accordance with aspects of the disclosed subject matter, the urine sensing device further includes a second hook extending radially and downwardly from the second end of the compression member opposite the first hook for hanging the urine sensing device onto an object external to the urine sensing device. In accordance with aspects of the disclosed subject matter, the second hook further comprises a curved portion comprising a handle for transporting the urine sensing device.

In yet another aspect, the presently disclosed subject matter provides a system for real-time and continuous monitoring of kidney function, comprising: (a) the urine sensing device as described herein, wherein the urine sensing device continuously monitors urine output flowing through a catheter of a catheterized patient into the urine collection vessel hanging on the first hook of the urine sensing device; and (b) a portable monitoring device for real-time and continuous assessment of kidney function based on a combination of real-time and continuous monitoring of urine output and volumetric flow rate based on second to second measurement of the weight of the urine collection vessel, optionally real-time and continuous monitoring of levels of the at least one urinary component, and/or real-time and continuous monitoring of at least one intra-operative risk factor indicative of acute kidney injury.

In accordance with aspects of the disclosed subject matter, the catheter comprises a Foley catheter. In accordance with aspects of the disclosed subject matter, the system includes a non-kink snap on tube guard for the Foley catheter. In accordance with aspects of the disclosed subject matter, the system includes an external device selected from the group consisting of an anesthesia monitor, a perfusion pump, a heart-lung machine, a cerebral oximeter, an oxygenator, a patient monitor, or any combination thereof. In accordance with aspects of the disclosed subject matter, the anesthesia monitor or the patient monitor continuously monitors in real-time at least one of a mean arterial pressure of the catheterized patient, a medication administered to the catheterized patient, a fluid administered to the catheterized patient, and combinations thereof.

In accordance with aspects of the disclosed subject matter, the portable monitoring device comprises: (i) a communications interface for automatically receiving real-time urine output continuously transmitted via the communications interface of the urine sensing device, optionally real-time levels of the at least one urinary component continuously transmitted from the at least one sensor via the communications interface of either the urine sensing device or the communications interface of (i), and/or real-time input comprising the at least one intra-operative risk factor indicative of acute kidney injury continuously transmitted from the external device via the communications interface of (i); (ii) a non-transitory computer readable storage medium having computer readable program code embodied thereon for executing an acute kidney injury risk algorithm that calculates the catheterized patient's risk of developing acute kidney injury as a percentage of the likelihood that the catheterized patient will develop acute kidney injury; and (iii) a graphical user interface comprising: (1) means for prompting a user to input pre-operative patient information, and (2) a display for graphically displaying the percentage of the likelihood that the catheterized patient will develop acute kidney injury.

In accordance with aspects of the disclosed subject matter, the pre-operative patient information is selected from group the consisting of a pre-operative Society of Thoracic Surgeons Risk Factor, pre-operative baseline urine density, pre-operative patient weight, and combinations thereof. In accordance with aspects of the disclosed subject matter, the display graphically displays at least one of real-time second to second urine output, real-time levels of the at least one urinary component, real-time input comprising the at least one intra-operative risk factor indicative of acute kidney injury, real-time second to second fluctuations in urine output, real-time second to second fluctuations in levels of the at least one urinary component, real-time second to second changes in the at least one intra-operative risk factor indicative of acute kidney injury, a plot of urine weight over time, an AKI risk score in the form of a percentage, alert color, literary instruction, and combinations thereof.

In accordance with aspects of the disclosed subject matter, the acute kidney injury risk algorithm calculates the catheterized patient's risk of developing acute kidney injury based on a weighting of acute kidney injury risk factors selected from the group consisting of the pre-operative Society of Thoracic Surgeon Risk Factors; KDIGO, RIFLE, and/or AKIN risk stratification Criteria for Urine Output; KDIGO/AKIN Criteria for Serum Creatinine; volumetric flow rate calculations based on baseline urine density, pre-operative patient weight, and real-time second to second fluctuations in weight of the urine collection vessel; real-time urine output adjusted for changes due to medication and/or fluid administered to the catheterized patient; optionally real-time levels of the at least one urinary component adjusted for changes due to medication and/or fluid administered to the catheterized patient; and/or real-time input comprising changes in the at least one intra-operative risk factor indicative of acute kidney injury.

In accordance with aspects of the disclosed subject matter, the pre-operative Society of Thoracic Surgeon Risk Factors are selected from the group consisting of: the planned, unplanned, complicated, or unexpected nature of a Coronary Artery Bypass operation; whether or not a valve is being altered in the surgery; whether or not another cardiac procedure is indicated; if the patient is admitted with a ventricular assist device (VAD); if a VAD is implanted during current hospitalization; if an aortic procedure is to be performed; if an atrial fibrillation procedure is performed; if the current case is canceled; if there are other non-cardiac related operations; patient age, gender, height, and weight; if hemodynamic data such as ejection fraction is done; if a patient had experienced heart failure within 2 weeks; patient race, if the patient is Hispanic, Latino, or Spanish Ethnicity; if the patient is in renal failure or on dialysis; the patient's last creatinine level; the occurrence of a cardiac symptoms at time of current admission selected from the group consisting of stable angina, unstable angina, angina equivalent, non-ST Elevation myocardial infarction, ST Elevation myocardial infarction, and combinations thereof; the occurrence of a cardiac symptoms at time of surgery selected from the group consisting of stable angina, unstable angina, angina equivalent, non-ST Elevation myocardial infarction, ST Elevation myocardial infarction, and combinations thereof; if a prior myocardial infarction existed; if cardiac arrhythmia is present; if patient has chronic lung disease; if patient has cerebrovascular disease; if peripheral arterial disease is present; if patient has diabetes; if hypertension is present; whether or not the patient is immunocompromised; if endocarditis is present; if coronary disease exists; the nature of the surgery; if the patient has been resuscitated within one hour of the start of the procedure; if the patient has been resuscitated between 1 and 24 hours from the start of the procedure; if the patient is experiencing cardiogenic shock; if patient has an intra-aortic balloon pump installed; if patient is on inotropes; if patient has had a previous cardiac intervention; if mitral valve or aortic disease is present, the degree of mitral valve insufficiency, the degree of tricuspid insufficiency; the degree of aortic insufficiency, and the incidence of current cardiovascular surgery, and combinations thereof.

In accordance with aspects of the disclosed subject matter, the KDIGO Criteria for Urine Output is selected from the group consisting of stratification of acute kidney injury in increasing severity stages wherein said stages are defined as the following: stage 1 is defined as <0.5 ml/kg/h for 6-12 hours, stage 2 is defined as <0.5 ml/kg/h for >12 hours, and stage three is defined as <0.3 ml/kg/h for more than 24 hours, or anuria for more than 12 hours, and combinations thereof. In accordance with aspects of the disclosed subject matter, the KDIGO/AKIN Criteria for Serum Creatinine is selected from the group consisting of stratification of acute kidney injury in increasing severity stages wherein said stages are defined as the following: stage 1 is defined as a 50%-99% increase in serum creatinine from baseline, or an acute increase of 0.3 mg/dL or more from baseline, stage 2 is defined as a 100%-199% increase in serum creatinine from baseline, and stage 3 is defined as a 200% or greater increase in serum creatinine from baseline, or any new need for hemodialysis.

In accordance with aspects of the disclosed subject matter, at least one urinary component is selected from the group consisting of urine sodium levels, urine oxygen tension levels, urine creatinine levels, urine potassium levels, and urine chloride levels. In accordance with aspects of the disclosed subject matter, at least one intra-operative risk factor indicative of acute kidney injury is selected from the group consisting of a real-time cerebral oximetry autoregulation threshold, nadir oxygen delivery, oxygen tension, mean arterial blood pressure, vasopressor dosage, diuretic delivery, fluid delivery, and combinations thereof.

In accordance with aspects of the disclosed subject matter, the acute kidney injury risk algorithm comprises a self-learning algorithm that adjusts the weighting of the acute kidney injury risk factors for each catheterized patient based on the relative significance of the acute kidney injury risk factors toward influencing outcomes of other catheterized patients presenting with similar acute kidney injury risk factors. In accordance with aspects of the disclosed subject matter, the system further comprises a patient database in electronic communication with the portable monitoring device, wherein the patient database comprises for each catheterized patient, the calculation of the patient's acute kidney injury risk, the acute kidney injury risk factors present in the patient, the weighting of the patient's acute kidney injury risk factors, and an indication of whether the patient developed acute kidney injury.

In still another aspect, the presently disclosed subject matter provides a method for real-time assessment of a patient's risk of developing acute kidney injury, the method comprising: (a) connecting a catheter of a catheterized patient to a urine collection vessel hanging on a urine sensing device, wherein the urine sensing device comprises a gravimetric sensor for second to second measuring of urine output, and optionally at least one ionic species sensor for second to second monitoring of at least one urinary component; (b) continuously monitoring urine output of said catheterized patient by measuring real-time second to second fluctuations in urine output with the gravimetric sensor; (c) optionally continuously monitoring a level of the at least one urinary component by measuring real-time second to second fluctuations in the level of the at least one urinary component with the at least one ionic species sensor; (d) transmitting the continuously monitored real-time fluctuations in urine output measured in (b) and optionally transmitting the continuously monitored real-time fluctuations in the level of the at least one urinary component measured in (c) to a patient monitoring device, wherein the patient monitoring device comprises: (i) a communications interface for automatically receiving the continuously monitored real-time fluctuations transmitted in (d); (ii) a non-transitory computer readable storage medium having computer readable program code embodied thereon for executing an acute kidney injury risk algorithm that calculates the catheterized patient's risk of developing acute kidney injury as a percentage of the likelihood that the catheterized patient will develop acute kidney injury; and (iii) a graphical user interface comprising means for prompting a user to input pre-operative patient information; (e) calculating the catheterized patient's risk of developing acute kidney injury as a percentage of the likelihood that the catheterized patient will develop acute kidney injury; and (f) displaying through the graphical user interface the catheterized patient's risk of developing acute kidney injury as a percentage of the likelihood that the catheterized patient will develop acute kidney injury.

In accordance with aspects of the disclosed subject matter, the urine sensing device further comprises: (i) a base member comprising a housing having a weight scale disposed therein; (ii) a compression member for transferring a force to the weight scale, the compression member comprising a first end mechanically coupled to the weight scale, a second end outside the housing opposite the first end, and a central portion extending longitudinally from the first end to the second end; and (iii) a first hook extending radially and upwardly from the second end of the compression member for hanging a urine collection vessel thereon, wherein the force of the weight of the urine collection vessel hanging on the first hook is transferred to the weight scale in the base member via the compression member. In accordance with aspects of the disclosed subject matter, the base member further comprises a force transducer disposed inside the housing for converting the force transferred to the weight scale into to a digital output signal indicating the weight of the urine collection vessel. In accordance with aspects of the disclosed subject matter, the method comprises continuously transmitting via a communications interface the digital output signal from the urine sensing device to the portable monitoring device. In accordance with aspects of the disclosed subject matter, at least one ionic species sensor is disposed inside the housing. In accordance with aspects of the disclosed subject matter, the urine sensing device further comprises a second hook extending radially and downwardly from the second end of the compression member opposite the first hook for hanging the urine sensing device onto an object external to the urine sensing device. In accordance with aspects of the disclosed subject matter, the second hook comprises a curved portion comprising a handle for transporting the urine sensing device. In accordance with aspects of the disclosed subject matter, the method further comprises continuously monitoring at least one intra-operative risk factor indicative of acute kidney injury by measuring real-time second to second changes in the at least one intra-operative risk factor indicative of acute kidney injury using an external device. In accordance with aspects of the disclosed subject matter, the external device is selected from the group consisting of an anesthesia monitor, a perfusion pump, a heart-lung machine, a cerebral oximeter, an oxygenator, a patient monitor, and combinations thereof. In accordance with aspects of the disclosed subject matter, the method further comprises automatically receiving, via the communications interface, the measured real-time second to second changes in the at least one intra-operative risk factor indicative of acute kidney injury. In accordance with aspects of the disclosed subject matter, the pre-operative patient information is selected from group the consisting of a pre-operative Society of Thoracic Surgeons Risk Factor, pre-operative baseline urine density, pre-operative patient weight, and combinations thereof. In accordance with aspects of the disclosed subject matter, the method further comprises displaying at least one of real-time second to second urine output, real-time levels of the at least one urinary component, real-time input comprising the at least one intra-operative risk factor indicative of acute kidney injury, real-time second to second fluctuations in urine output, real-time second to second fluctuations in levels of the at least one urinary component, real-time second to second changes in the at least one intra-operative risk factor indicative of acute kidney injury, a plot of urine weight over time, an AKI risk score in the form of a numerical percentage, alert color, or literary instruction, and combinations thereof.

In accordance with aspects of the disclosed subject matter, the method comprises adjusting the weighting of the acute kidney injury risk factors for each catheterized patient via the acute kidney injury risk algorithm based on the relative significance of the acute kidney injury risk factors toward influencing outcomes of other catheterized patients presenting with similar acute kidney injury risk factors. In accordance with aspects of the disclosed subject matter, the method comprises storing in a patient database in communication with the portable monitoring device, for each catheterized patient, the calculation of the patient's acute kidney injury risk, the acute kidney injury risk factors for the patient, the weighting of the patient's acute kidney injury risk factors, and an indication of whether the patient developed acute kidney injury.

Certain aspects of the presently disclosed subject matter having been stated hereinabove, which are addressed in whole or in part by the presently disclosed subject matter, other aspects will become evident as the description proceeds when taken in connection with the accompanying Examples and Drawings as best described herein below.

BRIEF DESCRIPTION OF THE DRAWINGS

Figure 1:
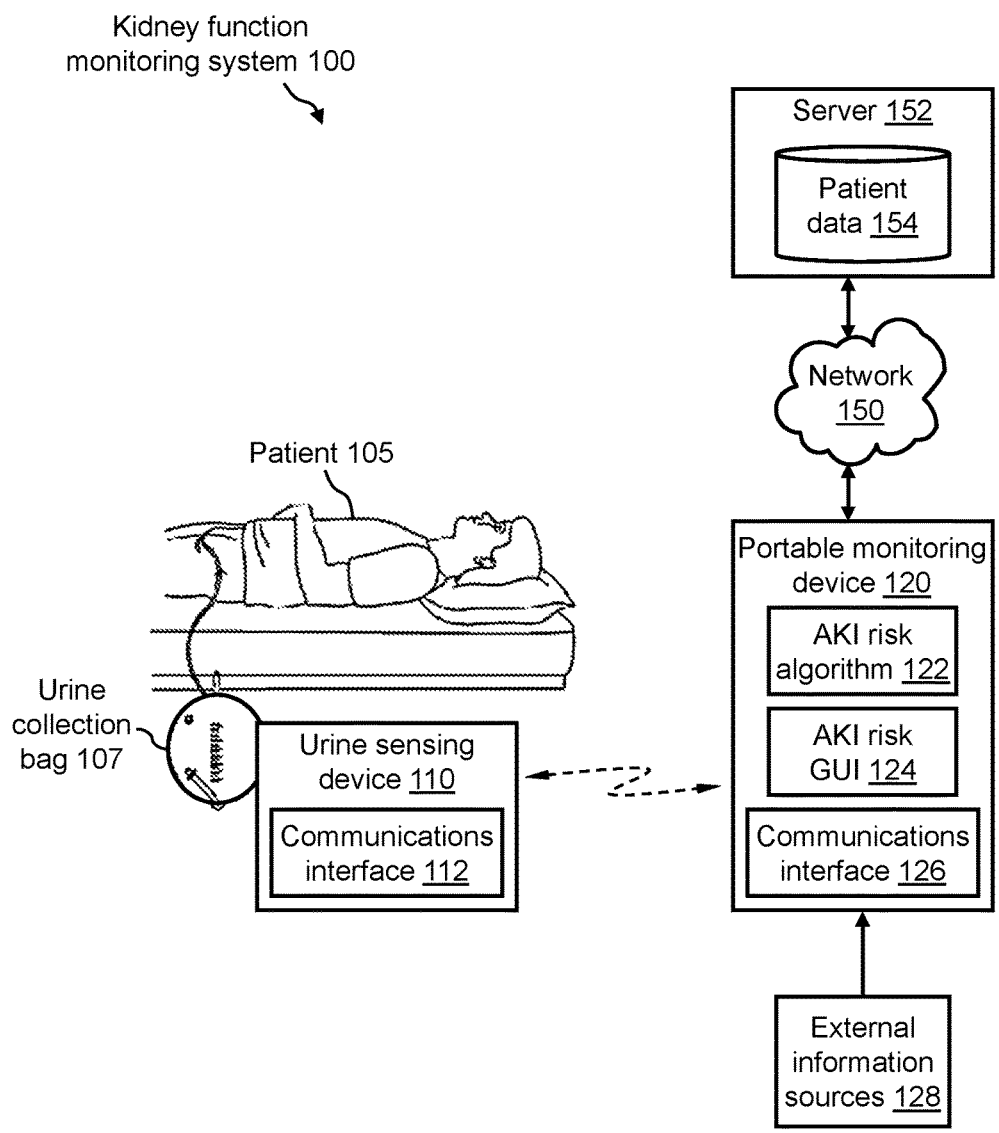
Figure 2:
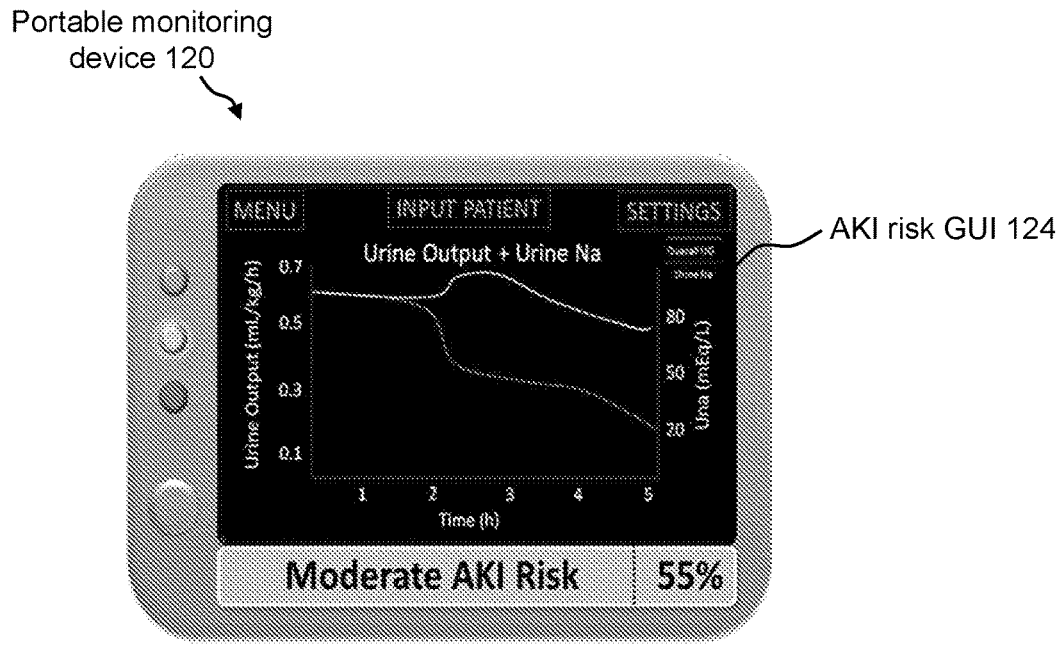
Figure 3:
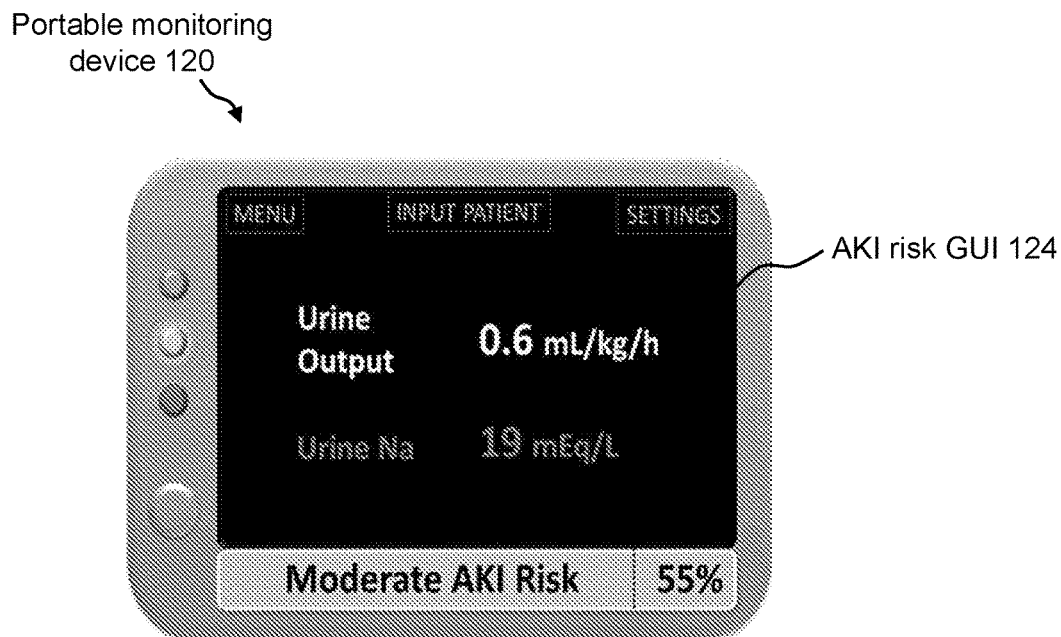
Figure 4:
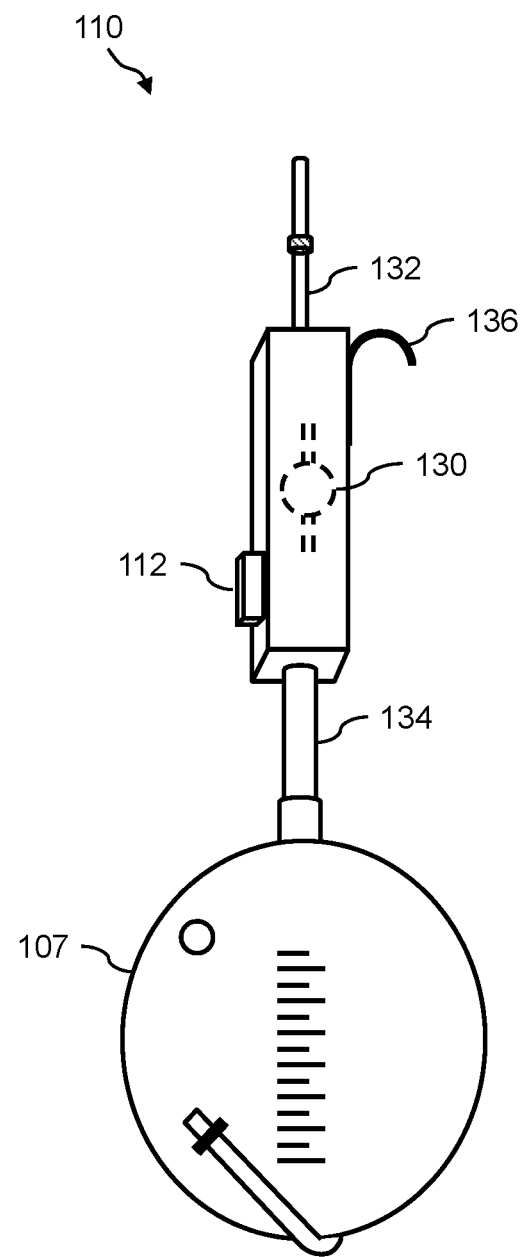
Figure 5:
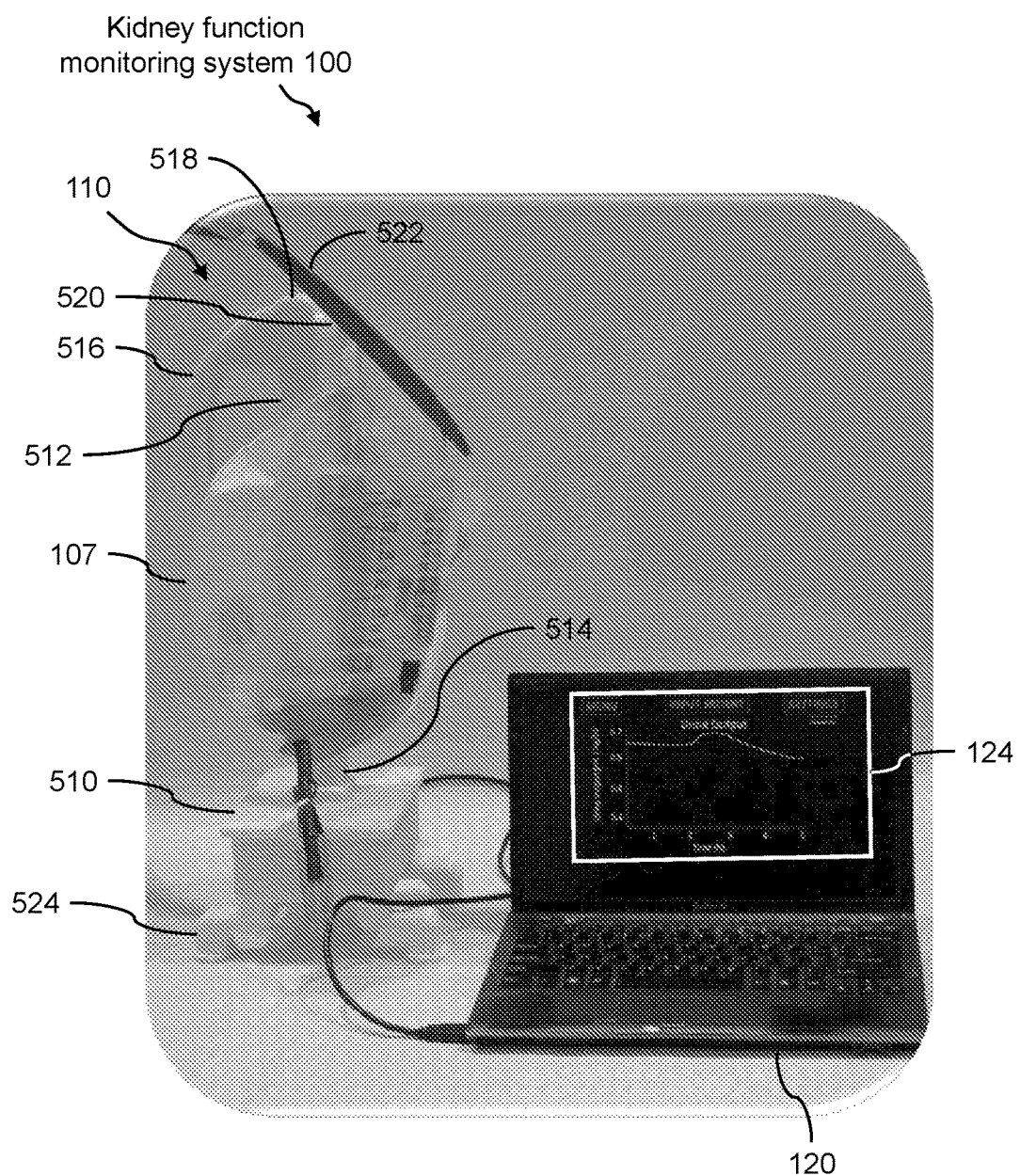
Figure 6:
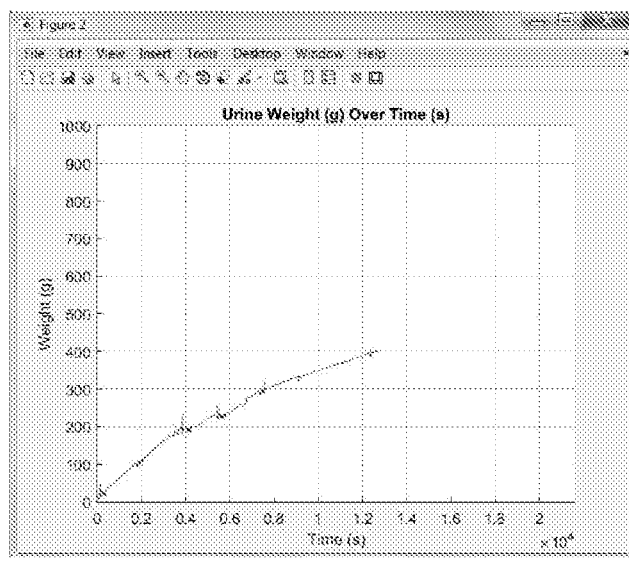
Figure 7:
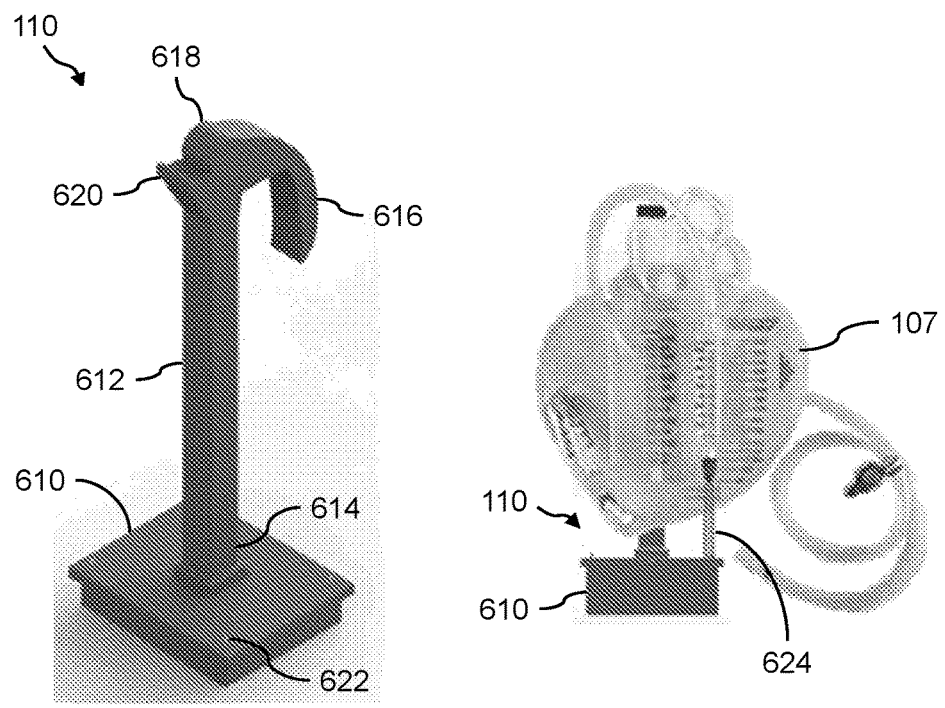
Figure 8:
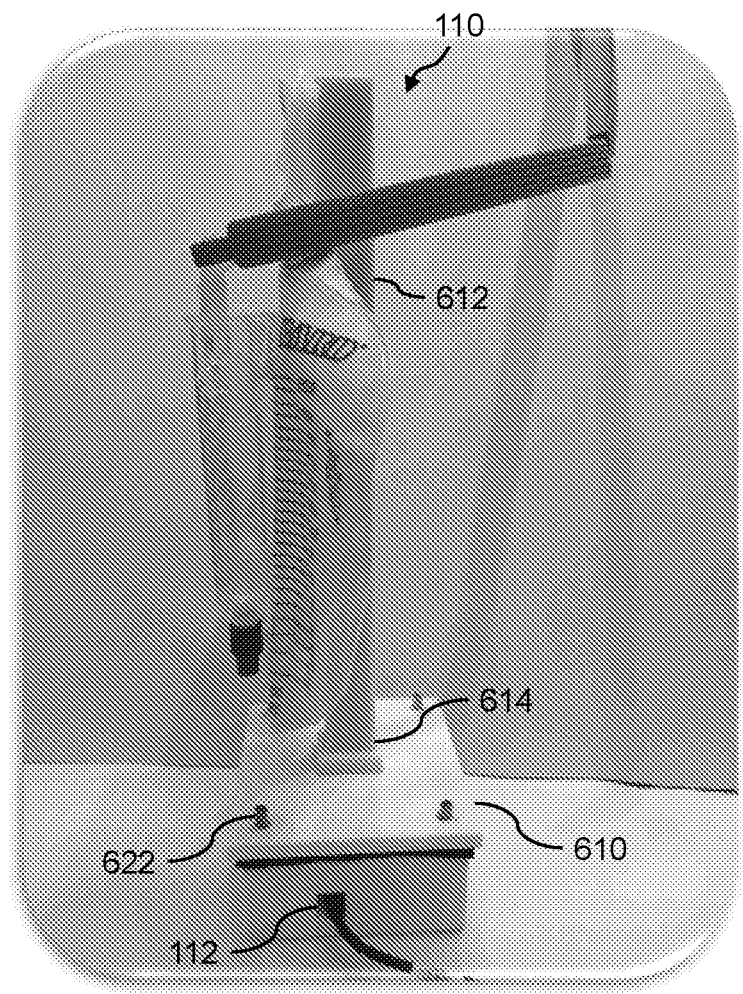
Figure 9:
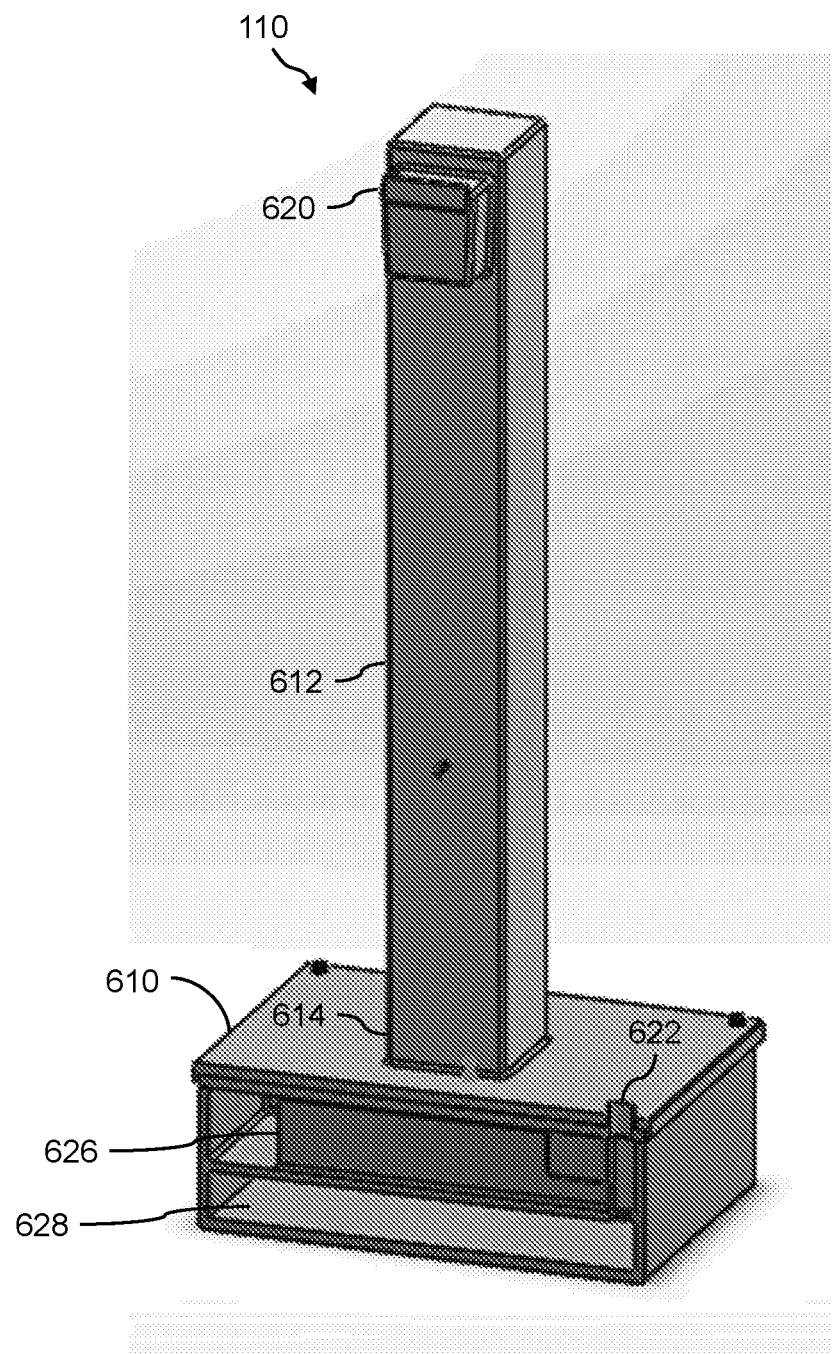
Figure 17:
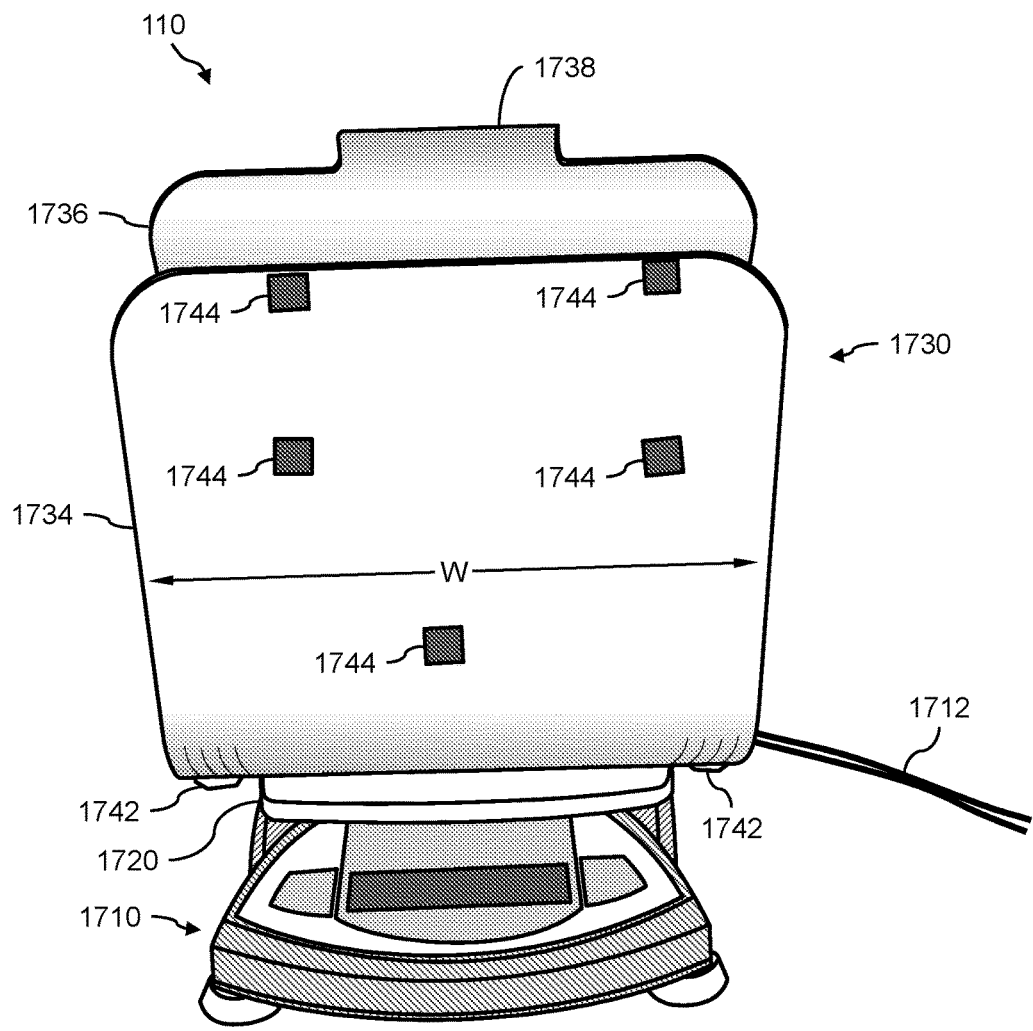
Figure 18:
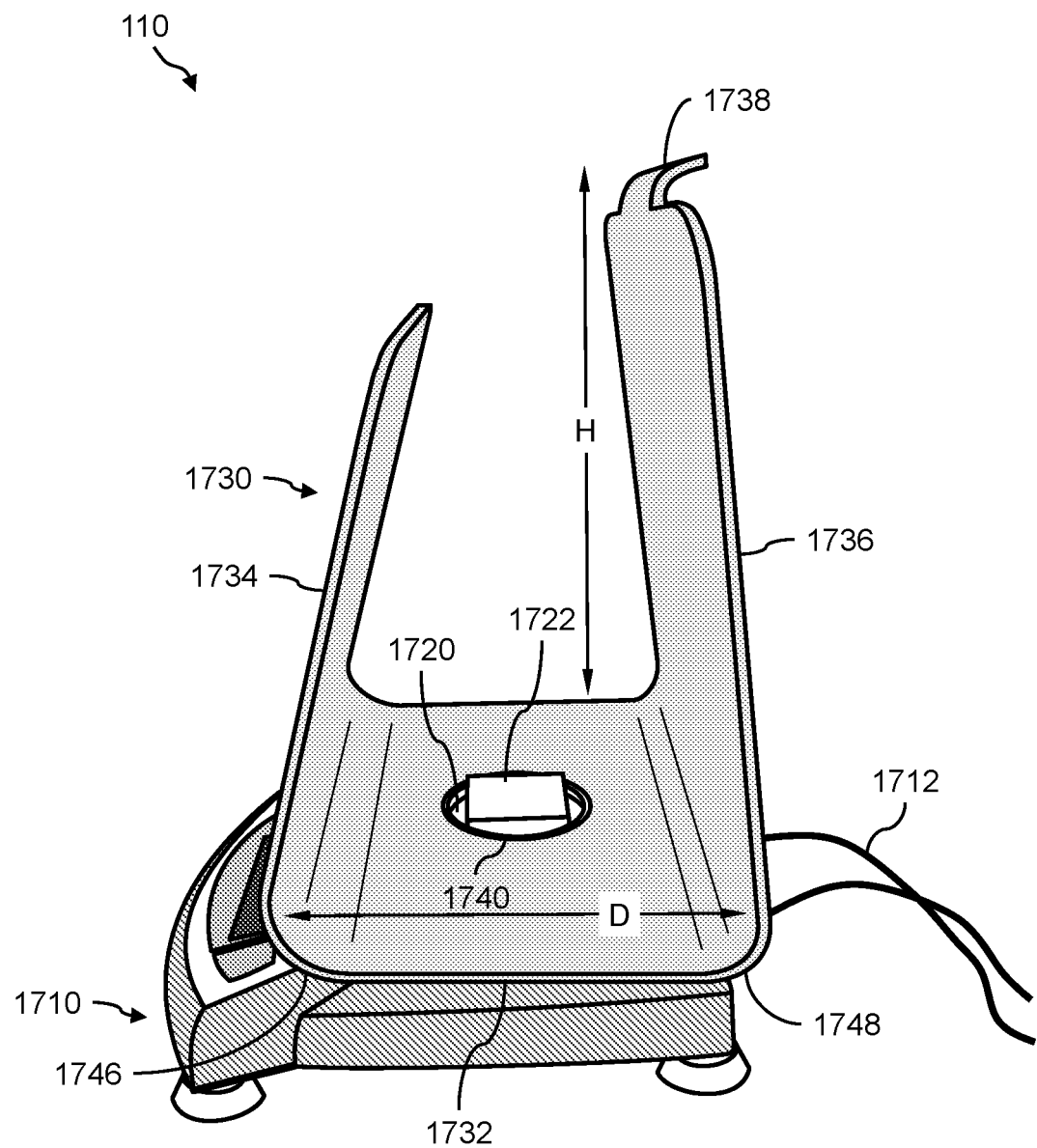
Figure 19:
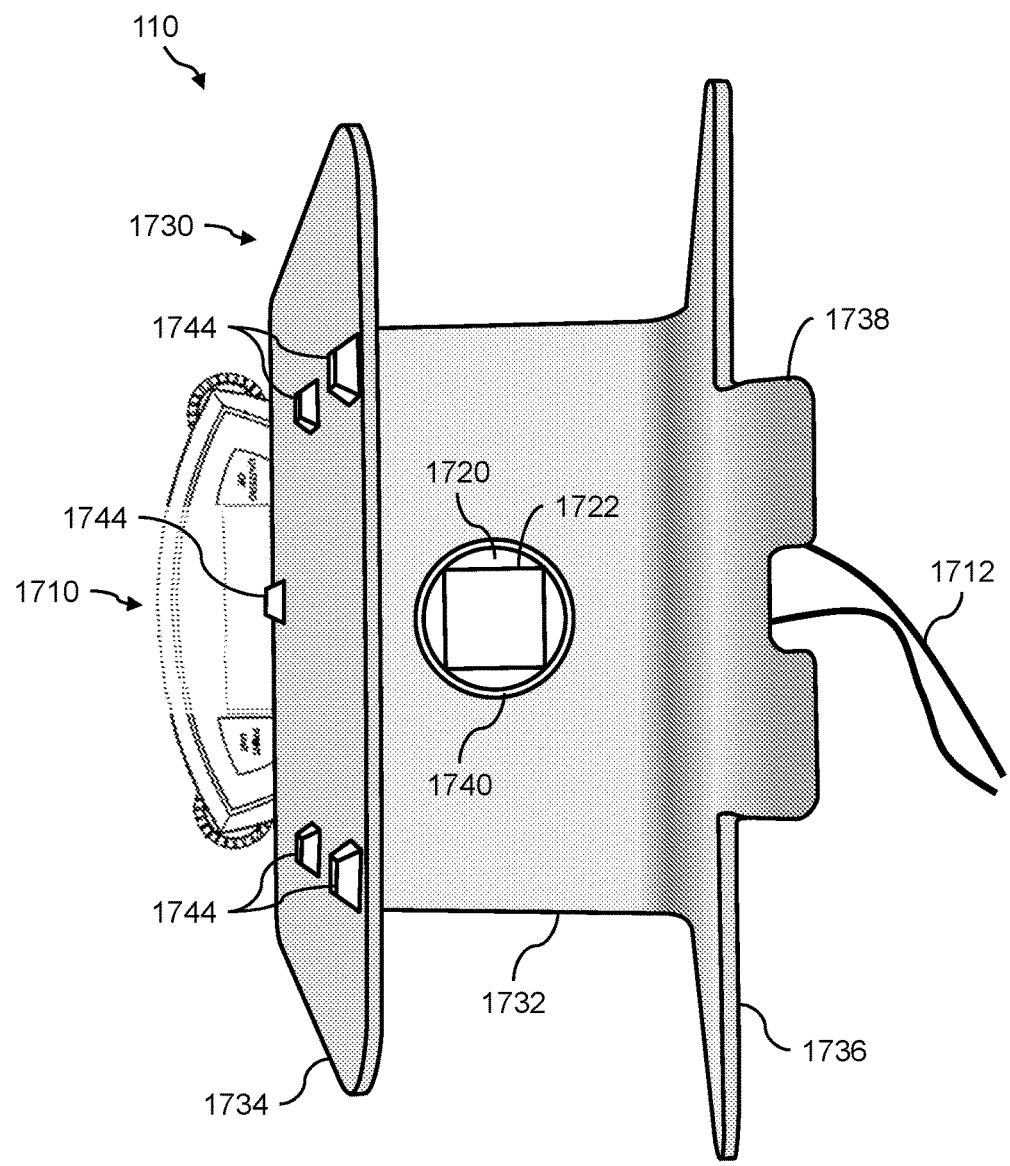
Figure 21:
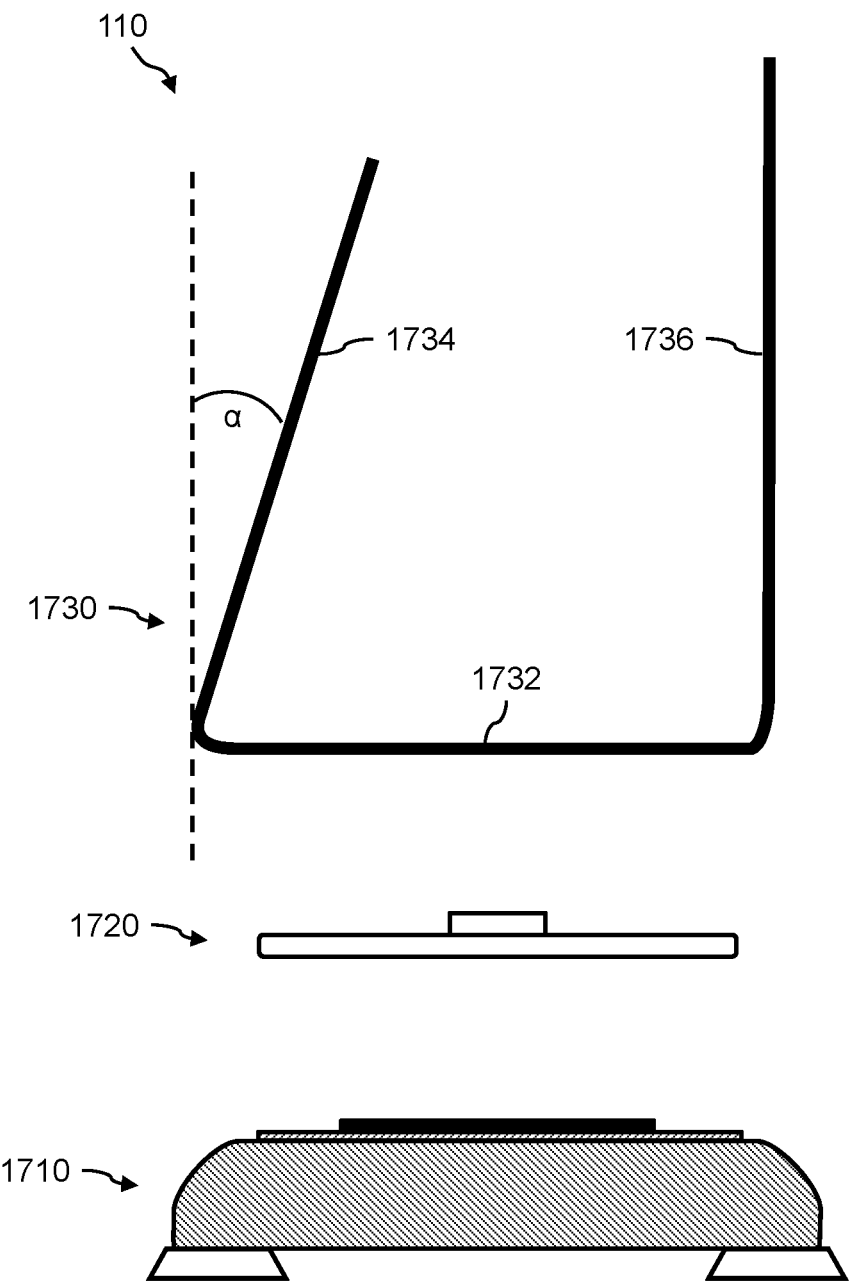
Figure 22A:
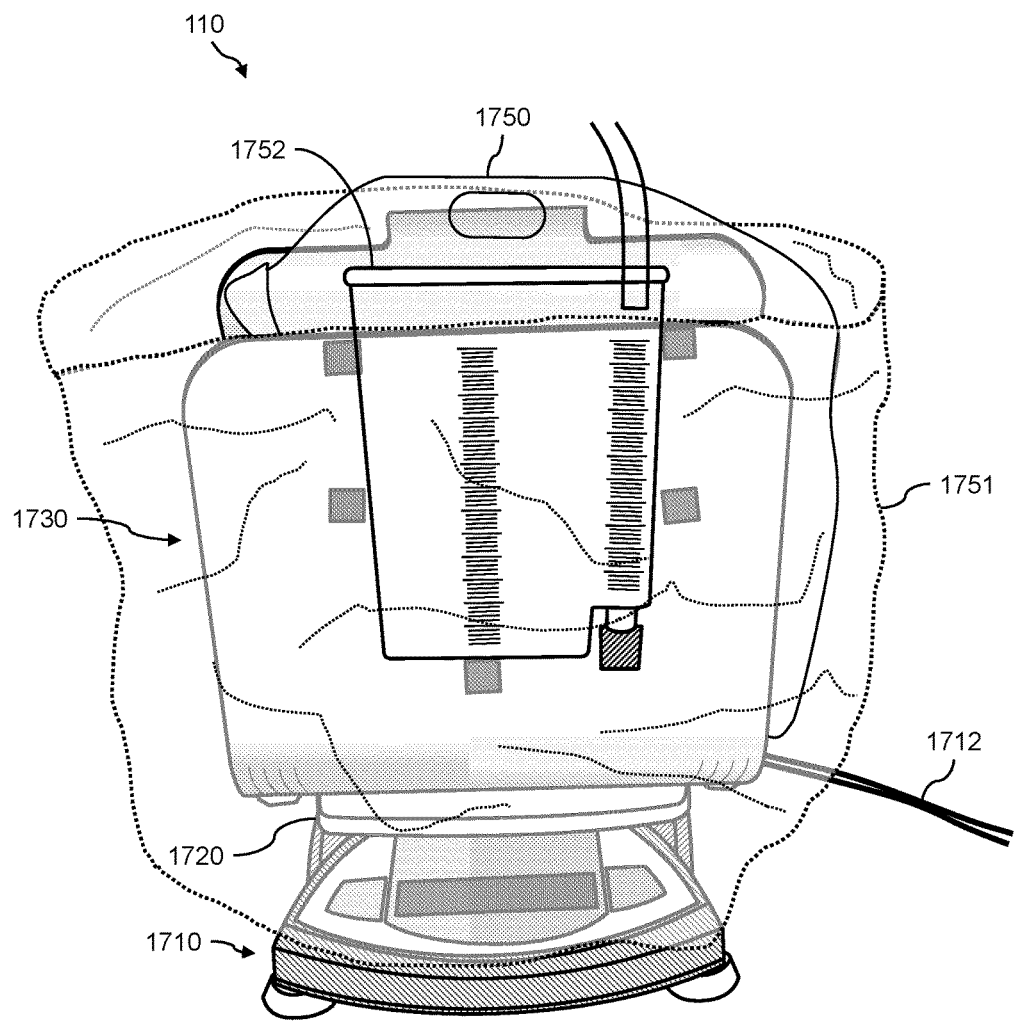
Figure 22B:
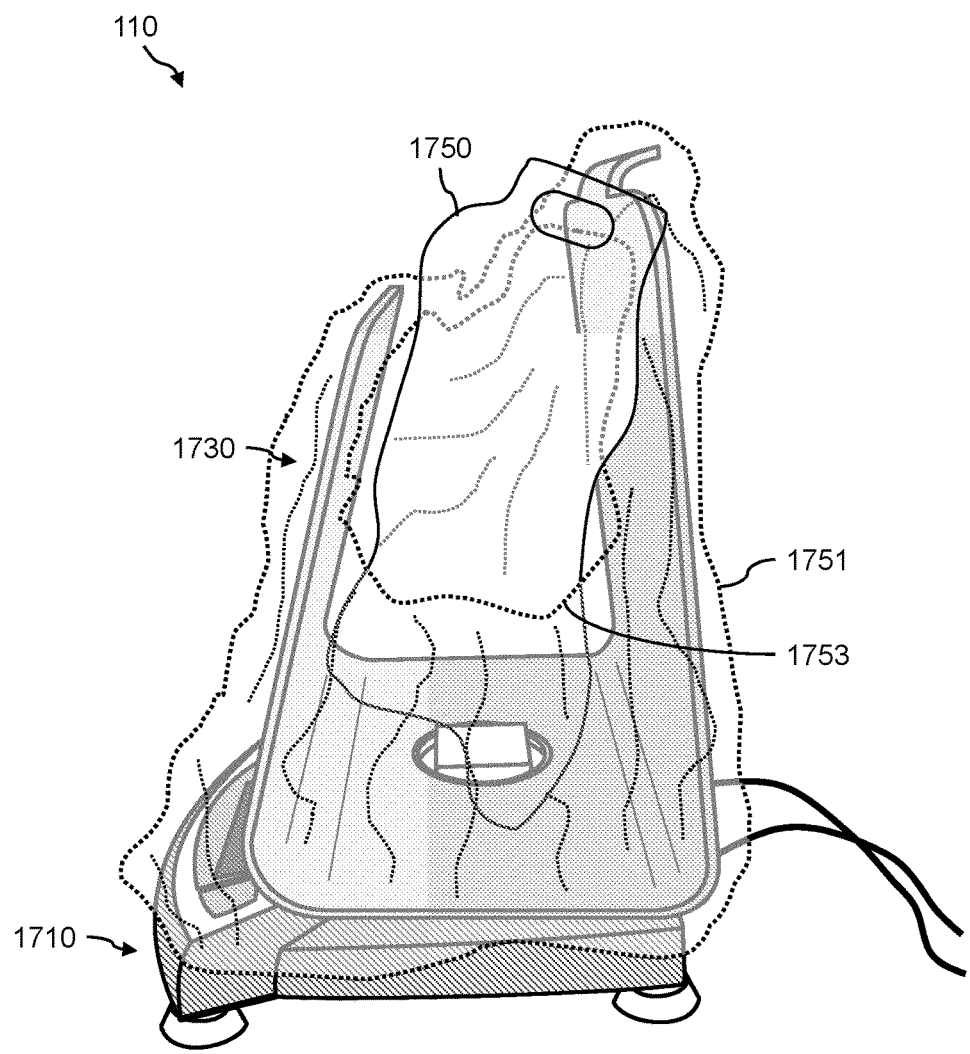
Figure 23A:
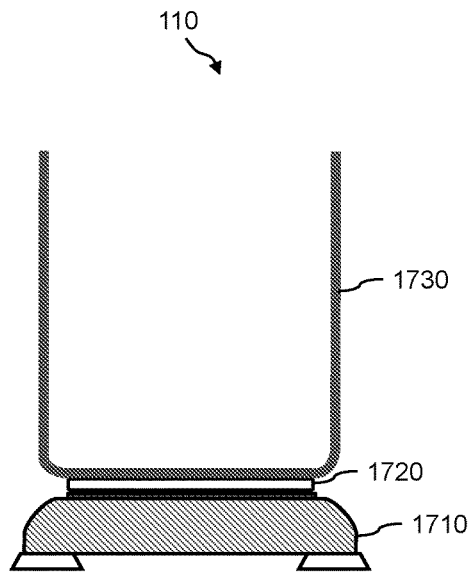
Figure 23B:
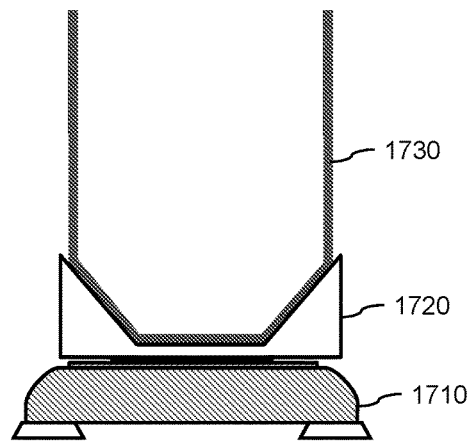
Figure 23C:
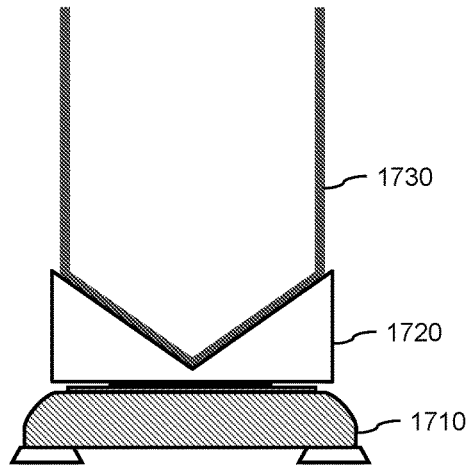
Figure 23D:
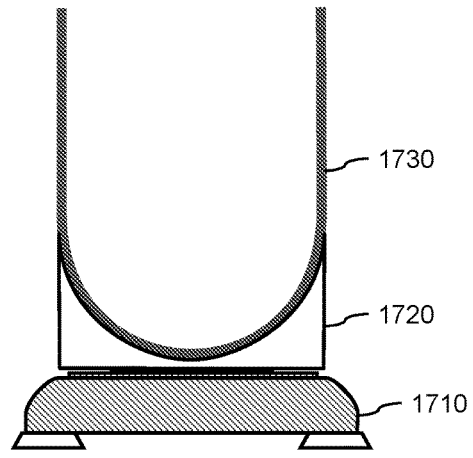
Figure 24:
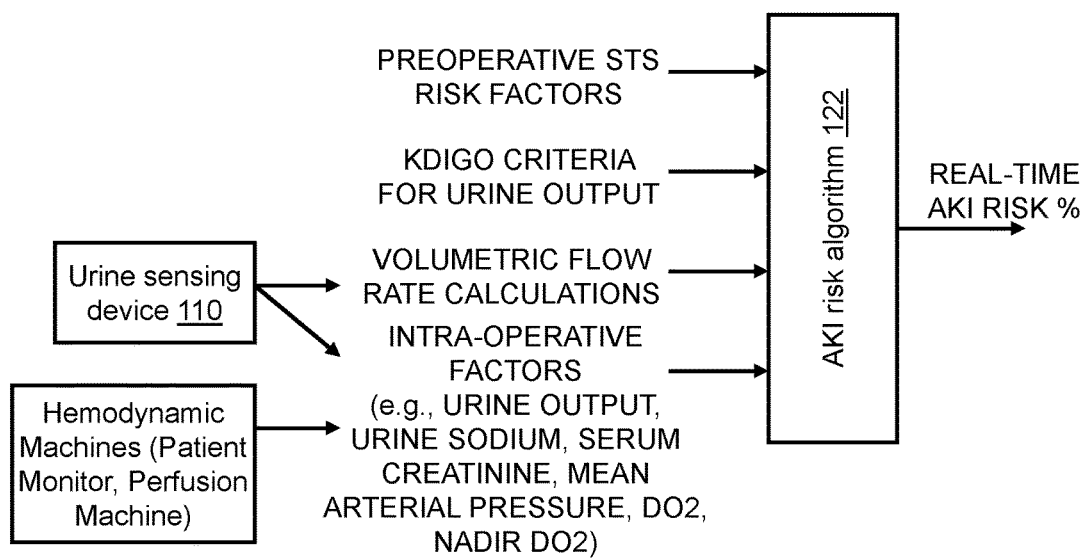
Figure 25:
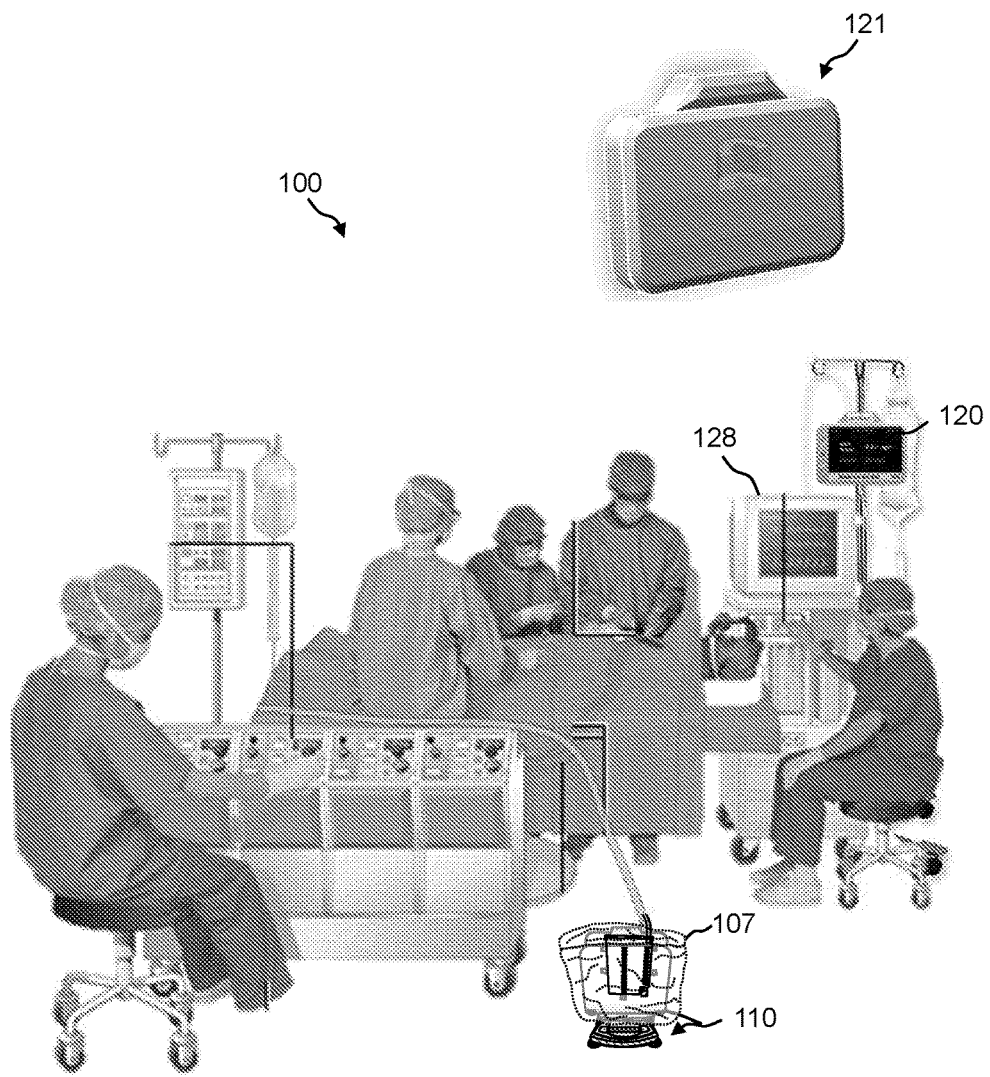
Figure 26:
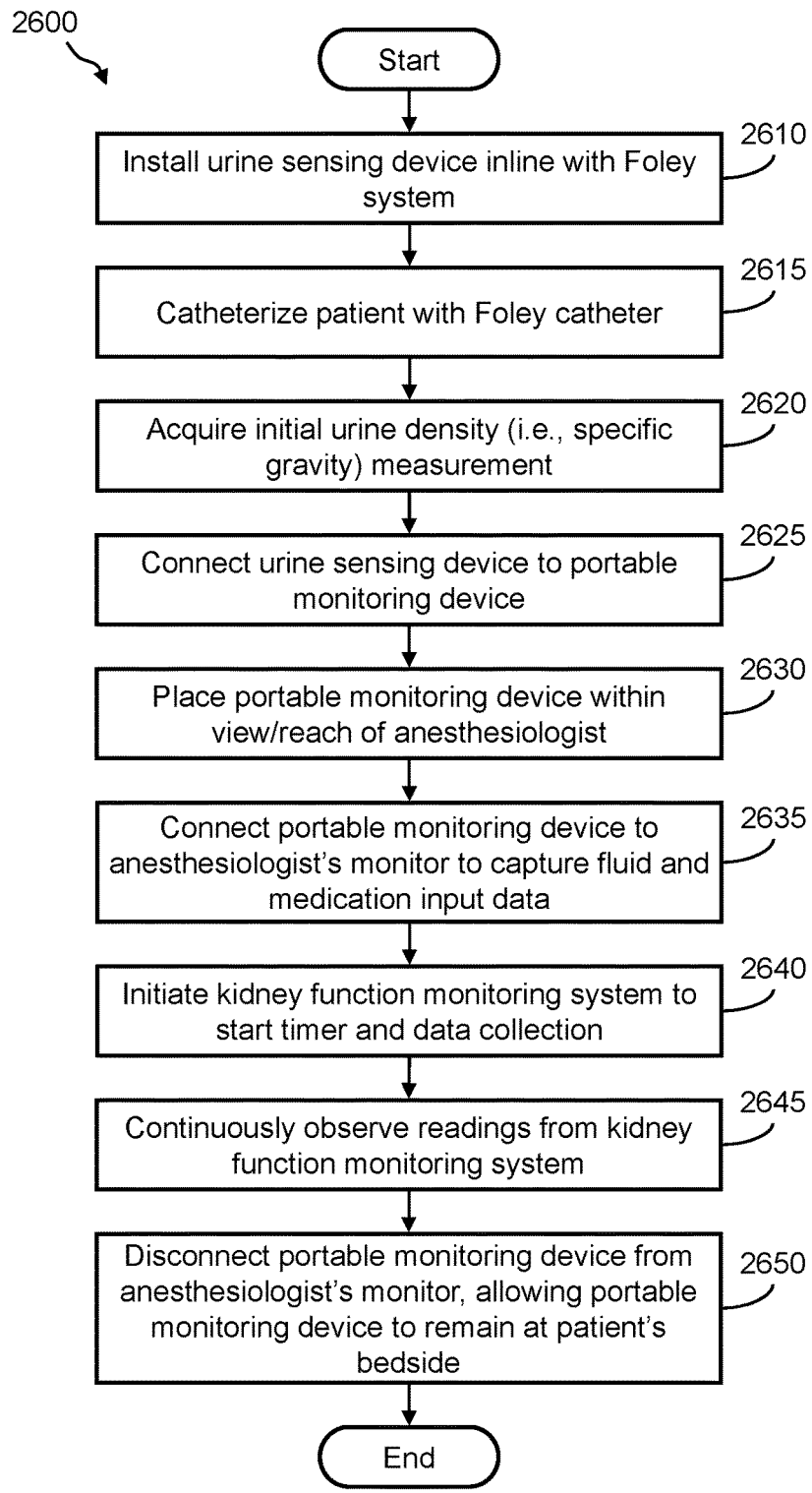
Figure 27:
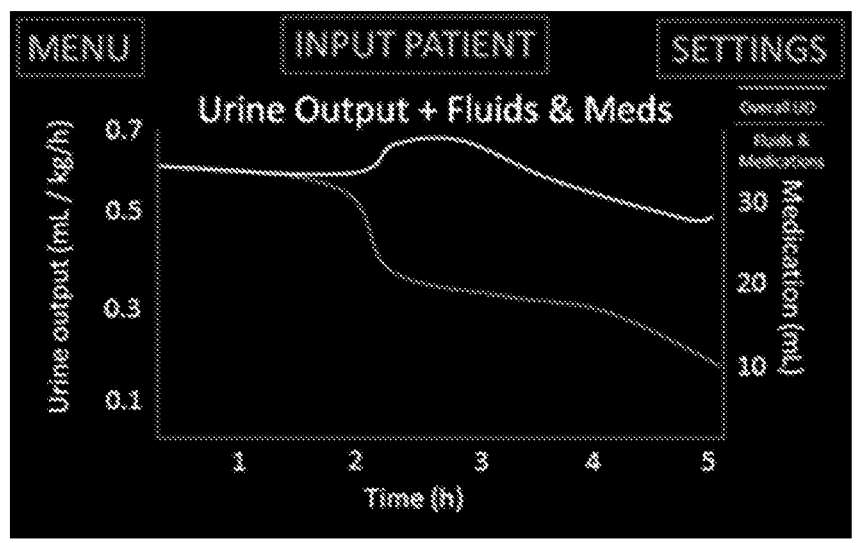

Having thus described the presently disclosed subject matter in general terms, reference will now be made to the accompanying Drawings, which are not necessarily drawn to scale, and wherein:

FIG. 1 illustrates a block diagram of an example of the presently disclosed kidney function monitoring system for early detection of AKI;

FIG. 2 and FIG. 3 show images of examples of a portable monitoring device and an AKI risk GUI of the presently disclosed kidney function monitoring system;

FIG. 4 illustrates a perspective view of an example of a urine sensing device of the presently disclosed kidney function monitoring system;

FIG. 5 shows an image of an example of the presently disclosed kidney function monitoring system comprising another example of the urine sensing device;

FIG. 6 shows a screenshot of another example of the AKI risk GUI of the presently disclosed kidney function monitoring system;

FIG. 7 and FIG. 8 show various views of yet another example of the urine sensing device of the presently disclosed kidney function monitoring system;

FIG. 9 shows a cutaway view of the base portion of the urine sensing device shown in FIG. 7 and FIG. 8;

FIG. 10, FIG. 11, FIG. 12, FIG. 13, FIG. 14, FIG. 15, and FIG. 16 show views of more details of the urine sensing device shown in FIG. 7, FIG. 8, and FIG. 9, which includes an ionic species sensor;

FIG. 17, FIG. 18, and FIG. 19 illustrate a front perspective view, a side perspective view, and a top down perspective view, respectively, of another example of the urine sensing device of the presently disclosed kidney function monitoring system;

FIG. 20A shows a perspective view of the urine sensing device of FIG. 17, FIG. 18, and FIG. 19 absent the stand and showing the interface;

FIG. 20B and FIG. 20C show perspective views of different embodiments of the bottom side of the interface;

FIG. 21 shows an exploded side view of the urine sensing device of FIG. 17, FIG. 18, and FIG. 19;

FIG. 22A shows a front perspective view of the urine sensing device of FIG. 17, FIG. 18, and FIG. 19 with a Foley bag and a urinometer installed thereon;

FIG. 22B shows a side perspective view of the urine sensing device of FIG. 17, FIG. 18, and FIG. 19 with a Foley bag and a urinometer installed thereon;

FIG. 23A, FIG. 23B, FIG. 23C, and FIG. 23D show side views of examples of other shapes of the stand and interface of the urine sensing device of FIG. 17, FIG. 18, and FIG. 19;

FIG. 24 illustrates a block diagram of an example an AKI risk algorithm of the presently disclosed kidney function monitoring system for early detection of AKI;

FIG. 25 shows an image of an operating room and an example of using the presently disclosed kidney function monitoring system for early detection of AKI;

FIG. 26 illustrates a flow diagram of an example of a method of using the presently disclosed kidney function monitoring system for early detection of AKI;

FIG. 27 shows a screenshot of yet another example of the AKI risk GUI of the presently disclosed kidney function monitoring system;

FIG. 28, FIG. 29, FIG. 30, and FIG. 31 show yet other views of the AKI risk GUI displaying plots of urine output vs various other conditions; and FIG. 32 through FIG. 46 show various screenshots of the AKI risk GUI when using the presently disclosed kidney function monitoring system.

The patent or application file contains at least one drawing executed in color. Copies of this patent or patent application publication with color drawings will be provided by the Office upon request and payment of the necessary fee.

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

In some embodiments, the presently disclosed subject matter provides a system 100 for and method of monitoring kidney function, wherein the system and method can be used for the early detection of acute kidney injury (AKI). Namely, a kidney function monitoring system is provided that is a portable urine monitor system that can provide real-time and continuous feedback about urine output, optionally levels of at least one urinary component (e.g., urine sodium levels), and/or at least one intra-operative risk factor indicative of acute kidney injury (e.g., a hemodynamic threshold for mean arterial pressure (MAP) and/or nadir oxygen delivery ($DO_2$)), for example, during cardiac surgery (e.g., coronary bypass surgery) and in the intensive care unit.

The presently disclosed kidney function monitoring system comprises at least one urine sensing device (e.g., an external Foley catheter attachment unit), wherein the urine sensing device comprises a flowmeter, a gravimetric scale, a weight scale, at least one ionic species sensor (also referred to herein as an ion selective sensor), or any combinations thereof for the second-to-second monitoring of urine output and continuous sodium and/or other monovalent ion species. In one example, the urine sensing device comprises a weight scale, an interface, and a stand, wherein a Foley bag and urinometer can be installed in/on the stand, for the second-to-second monitoring of urine output.

Further, the presently disclosed kidney function monitoring system comprises a portable monitoring device, which is a multi-parameter monitor, for receiving a plurality of inputs from the urine sensing device and any other sources external to the urine sensing device and portable monitoring device. The portable monitoring device comprises an adaptive and modular self-learning algorithm (i.e., an AKI risk algorithm) for the real-time assessment of AKI risk based, for example, on a weighted combination of inputs and established pre-operative based AKI clinical risk scores, such as Thakar's risk score, the Society of Thoracic Surgeon's risk score, and the like, and any combinations thereof. The portable monitoring device also comprises a graphical user interface (i.e., an AKI risk GUI) capable of prompting a user for inputs to the AKI risk algorithm. Information displayed on the graphical user interface may include, for example, readings from any of the pre-operative and real-time inputs from urine sensing device, optionally the ionic species sensor and/or any other external information sources, for the real-time and continuous monitoring of kidney function.

The intended use of the presently disclosed kidney function monitoring system 100 and method is to monitor real-time changes in urine output, which can facilitate in the early detection of developing conditions, such as AKI. The target population consists of cardiac surgery and critical care patients, with an extension to all major surgeries. The urine sensing device is attached to the standard Foley catheter system, and designed to be used as frequently as close monitoring of patient urine output is deemed appropriate. The kidney function monitoring system is intended for inpatient and/or outpatient use in perioperative settings.

Referring now to FIG. 1 is a block diagram of an example of the presently disclosed kidney function monitoring system 100 for early detection of AKI. Kidney function monitoring system 100 comprises a urine sensing device 110 that further includes a communications interface 112. Kidney function monitoring system 100 is a portable urine monitor system that can provide real-time and continuous feedback about a plurality of kidney parameters, such as urine output, optionally at least one urinary component, and/or at least one intra-operative risk factor independently indicative of acute kidney injury other than urine output or the at least one urinary component, for example, during cardiac surgery and in the intensive care unit.

Urine sensing device 110 can include a gravimetric sensor (e.g., to measure the volume of urine produced every second using a weight scale and density-to-volume conversions), optionally an ion selective sensor, or any combinations thereof for the second-to-second monitoring of urine output and/or continuous sodium and/or other monovalent ion species. Using the gravimetric sensor to determine urine flow, urine sensing device 110 can be used to acquire real-time measurements of urine outflow. This is important because incremental decreases in urine flow can be an indicator that the kidney is not perfusing properly. An example of a urine sensing device 110 that includes a gravimetric sensor is shown herein below with reference to FIG. 4. An example of a urine sensing device 110 that includes a weight scale is shown hereinbelow with reference to FIG. 5.

Further, optionally using the ion selective sensor to analyze, for example, levels of at least one urinary component (e.g., sodium) in the urine, urine sensing device 110 can be used to acquire real-time measurements of sodium and/or any other monovalent ion species in urine. This may be important in some embodiments because many monovalent ion species, such as sodium constitute functional biomarkers that are implicated in the physiological development of AKI. For example, sodium urine levels can change as soon as ischemic damage occurs, as opposed to many other urine "damage" biomarkers that detect injury only after it has occurred. The value of monitoring sodium has been shown in literature. Additional examples of a urine sensing device 110 that include both the weight scale and the ion selective sensor are shown hereinbelow with reference to FIG. 7, FIG. 8, FIG. 9, and FIG. 10.

Communications interface 112 of urine sensing device 110 may be any wired and/or wireless communication interface for connecting to a network (not shown) or other devices and by which information may be exchanged with other devices. Examples of wired communication interfaces may include, but are not limited to, USB ports, RS232 connectors, RJ45 connectors, Ethernet, and any combinations thereof. Examples of wireless communication interfaces may include, but are not limited to, an Intranet connection, Internet, ISM, Bluetooth® technology, Bluetooth® Low Energy (BLE) technology, Wi-Fi, Wi-Max, IEEE 402.11 technology, ZigBee technology, Z-Wave technology, 6LoWPAN technology (i.e., IPv6 over Low Power Wireless Area Network (6LoWPAN)), ANT or ANT+ (Advanced Network Tools) technology, radio frequency (RF), Infrared Data Association (IrDA) compatible protocols, Local Area Networks (LAN), Wide Area Networks (WAN), Shared Wireless Access Protocol (SWAP), any combinations thereof, and other types of wireless networking protocols. Examples of information facilitated by the communications interface 112 include the transmission of readings from the urine sensing device 110, ion selective sensor, and other external sources of information 128, such as an external device that obtains real-time measurements of at least one-intraoperative risk factor indicative of acute kidney injury. In some embodiments, communications interface 112 continuously transmits in real-time a digital output signal from urine sensing device 110 to portable monitoring device 112 for real-time and continuous monitoring of urine output, a level of at least one urinary component, and at least one intra-operative risk factor indicative of acute kidney injury (i.e., at least one intra-operative risk factor indicative of acute kidney injury other than urine output or the at least one urinary component).

Kidney function monitoring system 100 further comprises a portable monitoring device 120, which is a multi-parameter monitor, for receiving a plurality of inputs from urine sensing device 110 and any other sources (e.g., external information sources 128). Examples of external information sources 128 include, without limitation, an external device such as, an anesthesia monitor, a perfusion pump, a heart-lung machine, a cerebral oximeter, an oxygenator, a patient monitor, and combinations thereof.

Portable monitoring device 120 can be any handheld or portable computing device capable of executing program instructions. Portable monitoring device 120 can be, for example, a tablet device (see FIG. 2 and FIG. 3), a laptop computer (see FIG. 5), a smartphone, a personal digital assistant (PDA), and the like. Portable monitoring device 120 continuously monitors urine output, optionally levels of at least one urinary component, and/or changes in at least one intra-operative risk factor indicative of acute kidney injury in real-time, for example, in some embodiments in second to second intervals, and/or in other embodiments minute to minute intervals. In some embodiments, portable monitoring device 120 provides for real-time and continuous assessment of kidney function based on a combination of real-time and continuous monitoring of urine output and volumetric flow rate based on second to second measurement of the weight of the urine collection vessel, optionally real-time and continuous monitoring of levels of at least one urinary component, and/or real-time and continuous monitoring of at least one intra-operative risk factor indicative of acute kidney injury.

An AKI risk algorithm 122 is installed and executing on portable monitoring device 120. In some embodiments, for example, portable monitoring device 120 includes a non-transitory computer readable storage medium having computer readable program code embodied thereon for executing an acute kidney injury risk algorithm 122 that calculates a catheterized patient's 105 risk of developing acute kidney injury as a percentage of the likelihood that the catheterized patient will develop acute kidney injury. AKI risk algorithm 122 is an adaptive and modular self-learning algorithm for the real-time assessment of AKI risk based, for example, on a weighted combination of inputs and established pre-operative based AKI clinical risk scores, such as Thakar's risk score, the Society of Thoracic Surgeon's risk score, and the like, and combinations thereof. The self-learning capability of AKI risk algorithm 122 can translate a weighting of pre-operative and real-time inputs into an AKI risk score. More details of AKI risk algorithm 122 are described hereinbelow with reference to FIG. 24.

Portable monitoring device 120 also comprises a graphical user interface (GUI); namely, an AKI risk GUI 124. Using AKI risk GUI 124, portable monitoring device 120 includes means for prompting a user for inputs to AKI risk algorithm 122 (e.g., prompting a user to input pre-operative patient information, such as a pre-operative Society of Thoracic Surgeons Risk Factor, pre-operative baseline urine density, pre-operative patient weight, and combinations thereof). Exemplary means for prompting a user to input pre-operative patient information include, without limitation, a touch screen, a pushbutton, a mouse, voice activation or dictation, a stylus, a digital input of data from an external source, for example, in the form of a .csv file, .m file, a .txt file, comma delimited, xml file, or other file type. GUI also includes a display for graphically depicting the percentage of the likelihood that a catheterized patient will develop acute kidney injury based on real-time inputs analyzed via AKI risk algorithm 122. Information displayed on AKI risk GUI 124 may include, for example, readings from any of the pre-operative and real-time inputs from urine sensing device 110 and/or any other sources (e.g., external information sources 128), for the real-time monitoring of kidney function. For example, AKI risk GUI 124 graphically displays at least one of real-time second to second urine output, optionally real-time levels of at least one urinary component, real-time input comprising at least one intra-operative risk factor indicative of acute kidney injury, real-time second to second fluctuations in urine output, optionally real-time second to second fluctuations in levels of the at least one urinary component, real-time second to second changes in the at least one intra-operative risk factor indicative of acute kidney injury, such as MAP, nadir delivered oxygen, vasopressor dosage, fluid perfusion levels, a plot of urine weight over time, an AKI risk score in the form of a numerical percentage, an alert color, or literary instruction, and combinations thereof. One example of an external information source 128 is the anesthesia monitor (not shown), which tracks fluids and medications administered to the patient 105 at different times and observes the patient's physiological response.

Additionally, portable monitoring device 120 comprises a communications interface 126. Communications interface 126 is the counterpart to communications interface 112 of urine sensing device 110. Accordingly, communications interface 126 can be substantially the same as communications interface 112 of urine sensing device 110, which is described above. For example, communications interface 126 and 112 can be a cable, such as a single USB cable, connecting urine sensing device 110 and portable monitoring device 120. Communications interface 126 of portable monitoring device 120 may incorporate a multi-input channel to receive a plurality of inputs from urine sensing device 110 and/or external information sources 128. Communications interface 126 automatically receives real-time urine output continuously transmitted via communications interface 112 of urine sensing device, optionally real-time levels of at least one urinary component continuously transmitted from at least one ionic species sensor via communications interface 112 of urine sensing device 110, or communications interface 126 of portable monitoring device 120 (depending on whether at least one ionic species sensor is disposed inside the housing of weight sensing base 510/610), and real-time input comprising at least one intra-operative risk factor indicative of acute kidney injury continuously transmitted from the external device or external information source 128 via communications interface 126.

FIG. 1 shows kidney function monitoring system 100 in use with respect to a patient 105, for example a catheterized patient. Namely, a Foley catheter in patient 105 supplies a conventional urine collection vessel 107. Urine sensing device 110 can be installed in line between the Foley catheter and urine collection vessel 107. Urine sensing device 110 has input and output ports that can be easily integrated into any existing Foley system, an example of which is shown in FIG. 4. Optionally, portable monitoring device 120 of kidney function monitoring system 100 can connect to a network, such as a network 150, via communications interface 126. Network 150 can be, for example, a local area network (LAN) or a wide area network (WAN) for connecting to the Internet. Using network 150, patient data can be transmitted from portable monitoring device 120 to, for example, a server 152. Server 152 can be any centralized computing device, server, or cloud server. A database of patient data 154 may reside at server 152 for storing patient-specific records of all surgical procedures and/or ICU care events with respect to portable monitoring device 120. In some embodiments, the patient data comprises information pertaining to the calculated AKI risk for the patient, as described further herein below. Multiple portable monitoring devices 120 (not shown) can be communicating with server 152 and logging data in patient data 154 (e.g., from each catheterized patient for which the presently disclosed self-learning algorithm calculated an AKI risk).

Referring now to FIG. 2 and FIG. 3 are images of examples of portable monitoring device 120 and AKI risk GUI 124 of the presently disclosed kidney function monitoring system 100. In these examples, portable monitoring device 120 is a tablet device with certain pushbutton and touchscreen controls. In one example, FIG. 2 shows AKI risk GUI 124 displaying a plot of the urine outflow and a plot of the level of at least one urinary component (e.g., sodium level) over time. Also displayed in AKI risk GUI 124 is an "AKI Risk" value, which is expressed as a percent and corresponding alert color. In this example, an "AKI Risk" value of 55% is considered a "Moderate AKI Risk," with a yellow alert color. In another example, FIG. 3 shows AKI risk GUI 124 displaying the current digital value of the urine outflow and the current digital value of the level of the at least one urinary component (e.g., sodium level). Again, the "AKI Risk" is displayed as a percent and alert color.

Referring now to FIG. 4 is a perspective view of an example of the urine sensing device 110 of the presently disclosed kidney function monitoring system 100. In this example, a gravimetric sensor 130 is provided in the body of urine sensing device 110. Gravimetric sensor 130 has an input line or tube 132 that can be fluidly connected to a standard Foley catheter. Gravimetric sensor 130 has an output line or tube 134 that can be fluidly connected to urine collection vessel 107. In this example, communications interface 112 provides an electrical connection port for signals and power to/from gravimetric sensor 130. Namely, the power to gravimetric sensor 130 can be supplied by portable monitoring device 120. Further, urine sensing device 110 includes a clip or hook 136 by which urine sensing device 110 can be hung vertically along with urine collection vessel 107 off the patient bed.

Gravimetric sensor 130 is used to measure at predefined intervals, such as every second or minute, the volume of urine produced. Gravimetric sensor 130 uses a mass scale and density-volume conversions. Gravimetric sensor 130 can be calibrated to zero-out any external disturbances, such as accidental bumping of urine collection vessel 107 through a plurality of signal processing filters such as Butterworth filters, moving average filters, Kalman filters, wavelet analysis, and the like, and any combinations thereof.

Referring now to FIG. 5 is an image of an example of the presently disclosed kidney function monitoring system 100 comprising an example embodiment of the urine sensing device 110. In this example, portable monitoring device 120 is a laptop computer, wherein AKI risk algorithm 122 is installed and executing on the laptop computer. The laptop computer 120 comprises a non-transitory computer readable storage medium having computer readable program code embodied thereon for executing AKI risk algorithm 122. AKI risk GUI 124 is shown in the display of the laptop computer 120.

Further, in this example, urine sensing device 110 comprises a weight sensing base 510 and a compression member 512. Weight sensing base 510 is a base member that comprises a housing and a built-in weight scale (not shown) for measuring the load (mass) pressing down from compression member 512 onto the surface or platform of weight sensing base 510. Compression member 512 (i.e., a vertical member) is mounted atop weight sensing base 510. Namely, a first end 514 of compression member 512 is mechanically coupled to the upper surface or platform of weight sensing base 510, wherein the platform of weight sensing base 510 is mechanically coupled to the built-in weight scale (not shown).

A hook 516 is provided at a second end 518 of compression member 512 for hanging urine sensing device 110 off the patient bed, for example, to facilitate transport of the urine sensing device 110 from the OR to the ICU. Further, a urine collection vessel hook 520 is provided near second end 518 of compression member 512, from which urine collection vessel 107 can be hung. FIG. 5 also shows a Foley catheter non-kink snap on tube guard 522, which is optional. When in use, weight sensing base 510 of urine sensing device 110 simply sits on a flat surface near the patient bed. Optionally, weight sensing base 510 can include stabilizing legs 524 for better security against tipping over.

The force of urine collection vessel 107 hanging on the urine bag hook 520 is transferred to the built-in weight scale in weight sensing base 510 via compression member 512.

Using the built-in weight scale in weight sensing base 510, weight measurements can be captured at predefined intervals, such as every second or minute, and then correlated to urine output volume. In some embodiments, weight sensing base 510 includes a force transducer (not shown) disposed inside the housing for converting the force transferred to the weight scale into a digital output signal indicating the weight of the urine collection vessel 107. In some embodiments, weight sensing base 510 includes at least one ionic species sensor disposed inside the housing for measuring levels of at least one urinary component.

Referring now to FIG. 6 is a screenshot of another example of AKI risk GUI 124 of the presently disclosed kidney function monitoring system 100. Namely, the AKI risk GUI 124 shown in FIG. 6 is an example of the urine output readout of the urine sensing device 110 shown in FIG. 5, depicting a plot of change in urine weight (g) over time (s).

Referring now to FIG. 7 and FIG. 8 are various views of yet another example embodiment of the urine sensing device 110 of the presently disclosed kidney function monitoring system 100. In this example, urine sensing device 110 comprises both a weight scale and at least one ionic species sensor, e.g., a sodium sensor.

In this example, urine sensing device 110 comprises a sensing base 610 and a compression member 612. Sensing base 610 is a base member that comprises a housing and a built-in weight scale (not shown) for measuring the load (mass) pressing down from compression member 612 onto the surface or platform of sensing base 610. Compression member 612 (i.e., a vertical member) is mounted atop sensing base 610. Namely, a first end 614 of compression member 612 is mechanically coupled to the upper surface or platform of sensing base 610, wherein the platform of sensing base 610 is mechanically coupled to the built-in weight scale (not shown).

A hook 616 is provided at a second end 618 of compression member 612 for hanging urine sensing device 110 off the patient bed. In some embodiments, hook 616 is provided with a curved portion that functions as a handle for transporting the urine sensing device. Further, a urine bag hook 620 is provided near second end 618 of compression member 612, from which urine collection vessel 107 can be hung. When in use, sensing base 610 of urine sensing device 110 simply sits on a flat surface near the patient bed.

The force of urine collection vessel 107 hanging on the urine bag hook 620 is transferred to the built-in weight scale in sensing base 610 via compression member 612. Using the built-in weight scale in sensing base 610, weight measurements can be captured at predefined intervals, such as every second or minute, and then correlated to urine output volume.

In some embodiments, weight sensing base 610 includes a force transducer (not shown) disposed inside the housing for converting the force transferred to the weight scale into to a digital output signal indicating the weight of the urine collection vessel 107.

In addition to the weight scale (not shown), sensing base 610 optionally includes an ion selective sensor. For example, sensing base 610 includes a sodium level sensing mechanism (see FIG. 9 through FIG. 16) that can be used to measure at predefined intervals, such as every minute, the urine sodium level.

Referring now to FIG. 9 is another view of the urine sensing device 110 shown in FIG. 7 and FIG. 8. This view shows that sensing base 610 of the urine sensing device 110 of FIG. 7 and FIG. 8 includes a built-in weight scale 626 and optionally a sodium sensing portion 628. In the example shown in FIG. 9, weight sensing base 610 includes one or more sample loading ports 622 installed in the upper surface of weight sensing base 610. Each of the sample loading ports 622 projects outwardly for receiving, for example, a tube 624 by which urine may flow into a chamber (e.g., a sodium sensing portion 628) inside the weight sensing base member 610. Namely, tube 624 is in fluid communication with the urine collection vessel 107 (see FIG. 7). The volume of urine can be a metered volume of urine that flows into the chamber at a predetermined volume and at predetermined time intervals, as described below.

Sodium sensing portion 628 may comprise certain features and/or functions for automatically extracting and measuring the sodium content of urine from a urine collection vessel. For example, sodium sensing portion 628 may comprise one or more motors to open and close a sample loading port 622 in fluid communication with a urine collection vessel by either twisting the cap on the sample loading port 622 or covering and uncovering the opening on the sample loading port 622, releasing a specified amount of urine.

Further, sodium sensing portion 628 may be either integrated into sensing base 610 of urine sensing device 110 or attached as a separate modular component; wherein sodium sensing portion 628 comprises a container to hold the urine being measured and tubing to connect the sensing chamber to the sample loading port 622.

Further, sodium sensing portion 628 may comprise a drainage chamber to accommodate urine after it has been analyzed. This prevents urine from flowing back into the patient's urine bag while also ensuring that the measurement of subsequent samples do not reflect the sodium concentration of previous samples. This drainage chamber can be incorporated into urine sensing device 110 or be housed separately and connected via tubing.

Further, sodium sensing portion 628 may comprise one or more ion-selective electrodes to measure the sodium content in the urine using electrochemical means. This can either be a combination electrode or a glass electrode and a reference electrode used together.

Further, sodium sensing portion 628 may comprise a mechanism to remove protein buildup from the tip of the sodium sensor. Possible embodiments include a motor to vibrate the electrode and shake proteins off the surface, a passive filtering system at the tip to prevent proteins from contacting the electrode surface, a charge-based electrophoresis system to remove charged proteins, or a chemical coating to prevent proteins from adhering to the surface. Another embodiment involves incorporating a separate chamber filled with water and/or an electrode cleaning solution to automatically fill and rinse the chamber after each sodium measurement.

Further, sodium sensing portion 628 may comprise a mechanism to dilute the urine in the sodium sensing chamber with water to enable the electrode to measure high sodium concentrations by incorporating a chamber with water to automatically drain into the sodium sensing chamber and dilute the urine sample.

Further, sodium sensing portion 628 and/or portable monitoring device 120 may comprise an analyzer to measure the voltage of the urine via electrode(s) in order to determine the ionic concentration of the urine. Possible embodiments include a pH meter, a voltmeter, and/or a potentiostat. Further, computer software may be used to convert the voltage readings to sodium concentrations.

FIG. 10 through FIG. 16 show views of examples of sodium sensing portion 628 of the urine sensing device 110 that may include some of the aforementioned features and/or functions.

Figure 10:
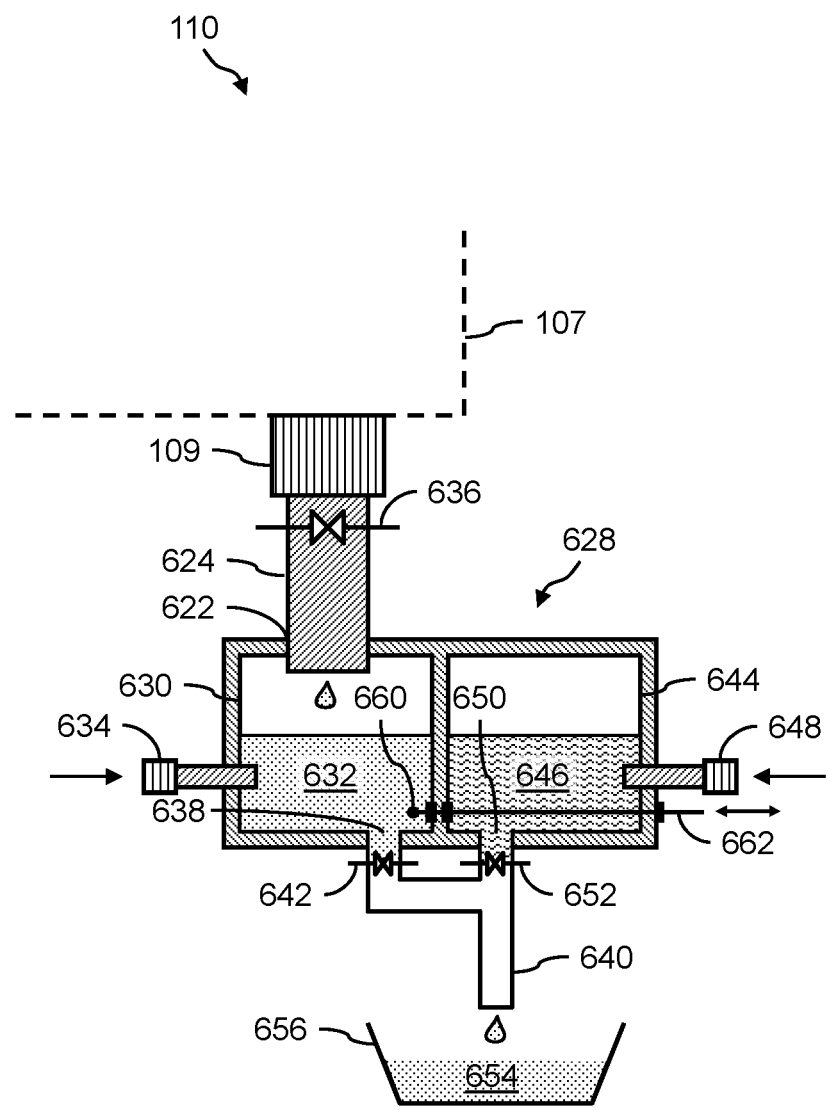

FIG. 10 is a cross-sectional view of one example of sodium sensing portion 628 of sensing base 610 of the urine sensing device 110, wherein the sodium sensing portion 628 shown in FIG. 10 includes some of the aforementioned features and/or functions.

In this example, sodium sensing portion 628 includes a urine sampling chamber 630 for holding a volume of urine 632, wherein urine 632 can be diluted with water. Accordingly, urine sampling chamber 630 provides a dilution and measurement chamber. Namely, sampling tube 618 fluidly connects a sampling port 109 of urine collection vessel 107 to sampling input port 620 of sensing base 610, wherein sampling input port 620 supplies urine sampling chamber 630. A water input port 634 also supplies urine sampling chamber 630. Accordingly, urine is supplied to urine sampling chamber 630 via sampling input port 620 and water is supplied to urine sampling chamber 630 via water input port 634. A valve 636 (e.g., a butterfly valve) is provided in sampling tube 618 for controlling the flow of urine. Urine sampling chamber 630 has an outlet 638 that supplies a waste tube 640. A valve 642 (e.g., a butterfly valve) is provided at outlet 638 for controlling the discharge flow from urine sampling chamber 630.

Sodium sensing portion 628 further includes a deionizing chamber 644 for holding a deionizing solution 646, such as a potassium chloride (KCL) solution. An input port 648 is used to supply deionizing solution 646 to deionizing chamber 644. Deionizing chamber 644 has an outlet 650 that supplies waste tube 640. A valve 652 (e.g., a butterfly valve) is provided at outlet 650 for controlling the discharge flow from deionizing chamber 644. In one example, waste liquid 654 from waste tube 640 is collected in a waste basin 656. In another example, a suction tube (not shown) is connected to waste tube 640 for removing waste liquid 654.

An ion-selective electrode (ISE) 660, also known as a specific ion electrode (SIE), is provided in urine sampling chamber 630. ISE 660 is arranged at the tip of a connecting rod 662. Connecting rod 662 passes through the walls of urine sampling chamber 630 and deionizing chamber 644 for manipulating laterally the position of ISE 660 inside urine sampling chamber 630. With respect to connecting rod 662, seals are provided at the walls of urine sampling chamber 630 and deionizing chamber 644 to prevent leakage. In one example, a stepper motor (not shown) is connected to the end of connecting rod 662 for controlling the motion thereof. Optionally, sodium sensing portion 628 can include built-in mechanisms, such as a vibration sonicator, for preventing protein build-up on ISE 660.

ISE 660 is a transducer (or sensor) that converts the activity of a specific ion dissolved in a solution into an electrical potential, which can be measured by a voltmeter or pH meter. In the urine sensing device 110, ISE 660 is used to sense the urine sodium level. Readout signals from weight scale 626 and ISE 660 in sensing base 610 are supplied to portable monitoring device 120 and more particularly to AKI risk algorithm 122 of portable monitoring device 120.

Figure 11:
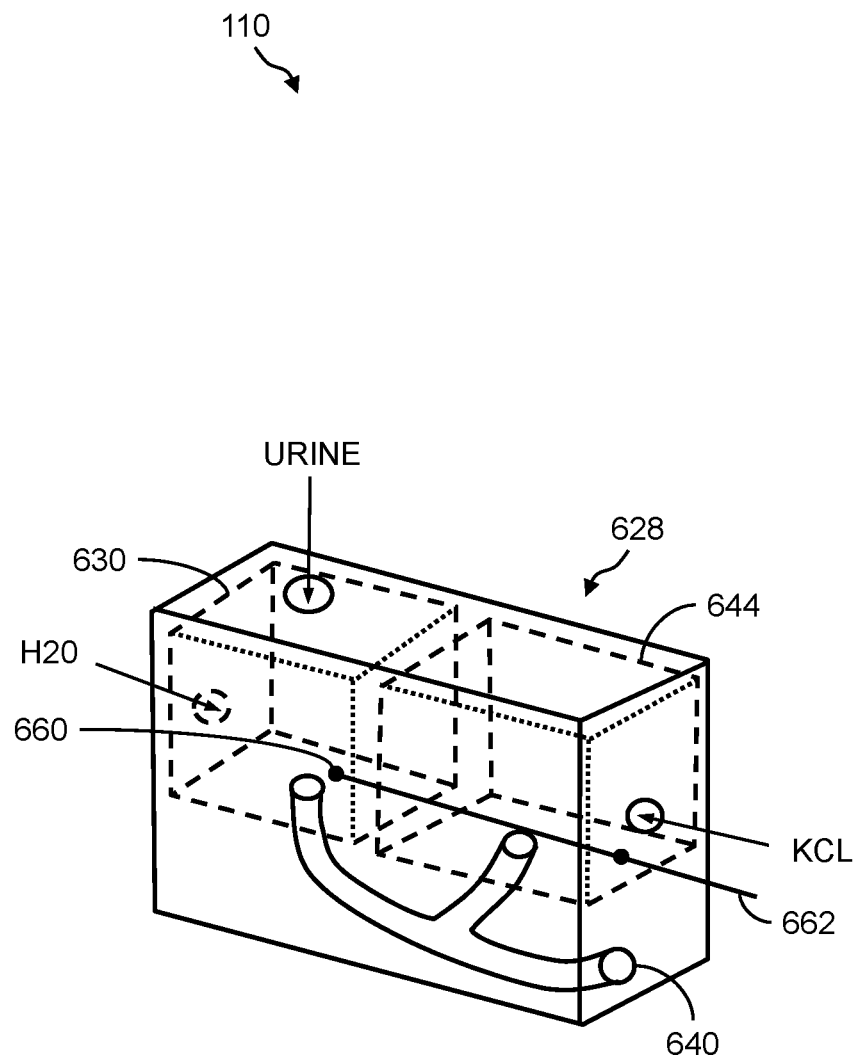

FIG. 11 is a perspective view of a box concept of implementing the sodium sensing portion 628 shown in FIG. 10. FIG. 10 and FIG. 11 show an example of a mechanism to remove protein buildup from the tip of ISE 660. This mechanism involves automatically retracting ISE 660 and filling deionizing chamber 644 with electrode cleaning solution to clean ISE 660 between measurements. FIG. 10 and FIG. 11 also show that urine sampling chamber 630 can be filled water to dilute the concentration of the urine. Sodium sensing portion 628 shown in FIG. 10 and FIG. 11 are examples of the sodium sensing portion 628 that is implemented directly into sensing base 610 of urine sensing device 110 and that is connected to the urine bag sampling port 109. Further, sodium sensing portion 628 shown in FIG. 10 and FIG. 11 may comprise one or more motors to open and close sampling port 109 of urine collection vessel 107 by either twisting the cap on sampling port 109 or covering and uncovering the opening on sampling port 109, releasing a specified amount of urine.

Figure 12:
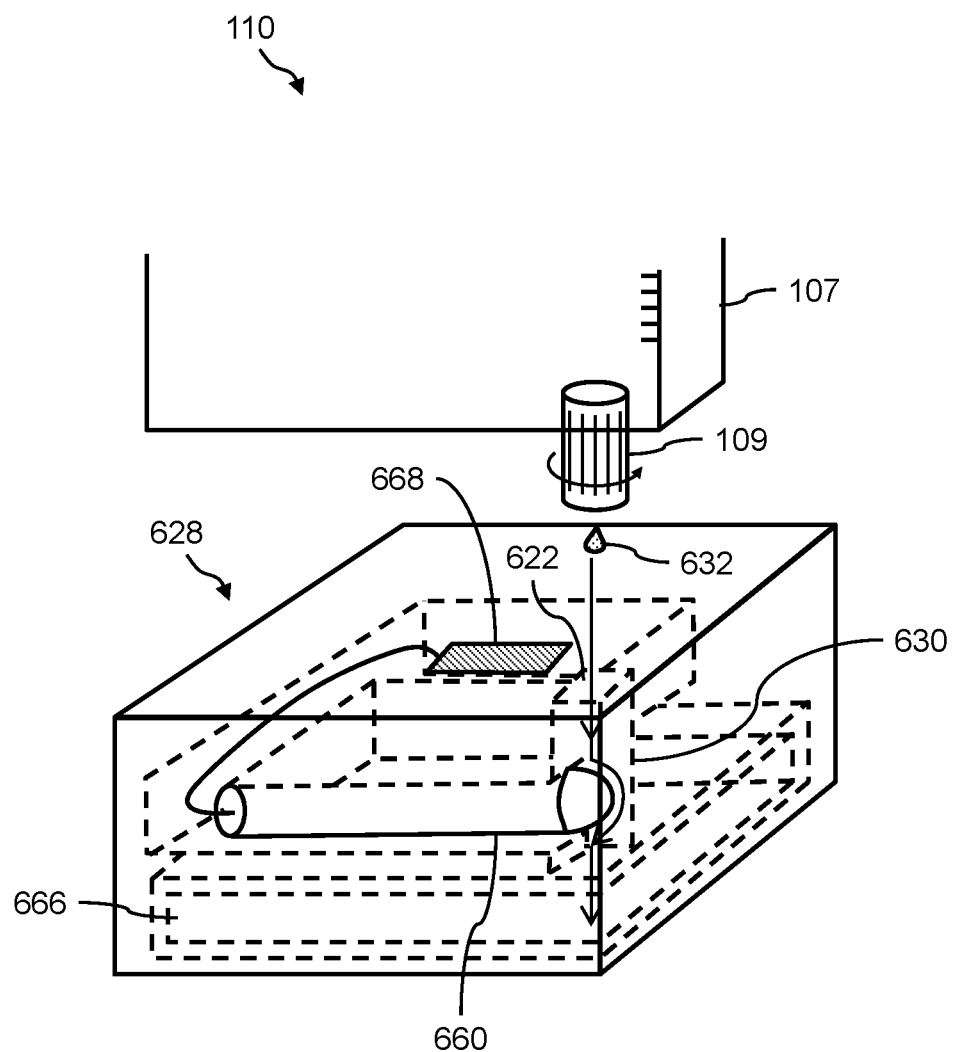
Figure 13:
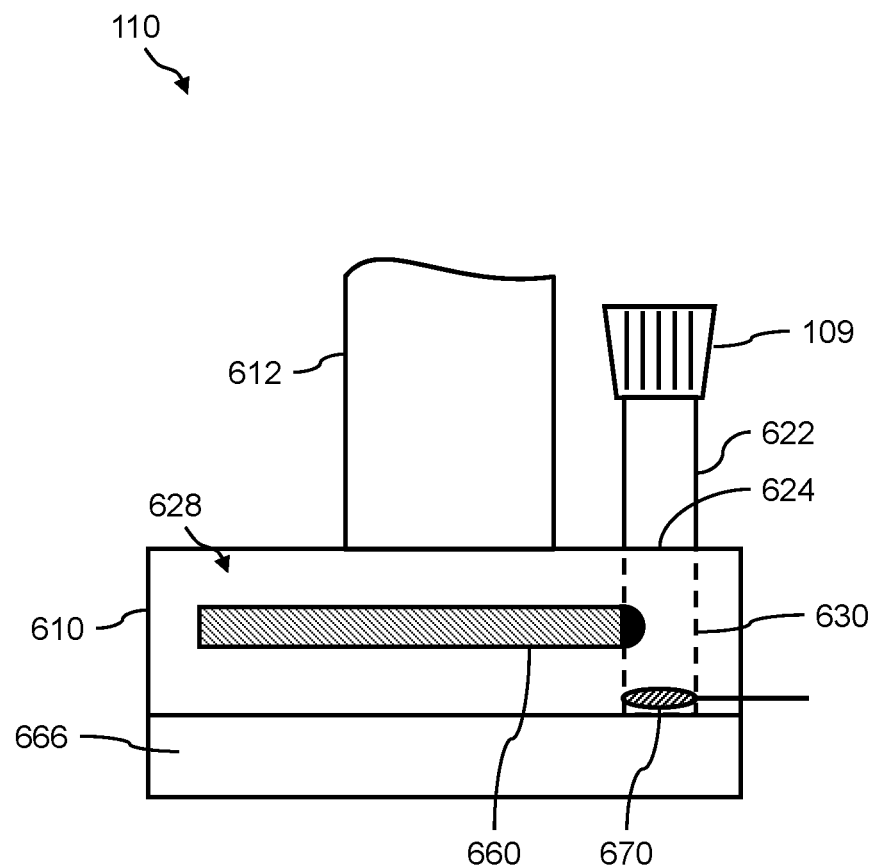

FIG. 12 and FIG. 13 show views of another example of sodium sensing portion 628 that is implemented directly into sensing base 610 of urine sensing device 110 and that is connected to the urine bag sampling port 109. Further, sodium sensing portion 628 shown in FIG. 12 and FIG. 13 may comprise one or more motors to open and close sampling port 109 of urine collection vessel 107 by either twisting the cap on sampling port 109 or covering and uncovering the opening on sampling port 109, releasing a specified amount of urine.

Further, the sodium sensing portion 628 shown in FIG. 12 and FIG. 13 includes a urine collection chamber 666 in place of waste basin 656. Namely, urine 632 passes through urine sampling chamber 630 and by ISE 660, then falls into urine collection chamber 666. Further, FIG. 12 shows a printed circuit board (PCB) 668 integrated into sodium sensing portion 628, wherein there is an electrical connection between PCB 668 and ISE 660. Further, FIG. 13 shows a valve 670 (e.g., a butterfly valve) at the outlet of urine sampling chamber 630 for controlling the flow of urine into urine collection chamber 666.

Figure 14:
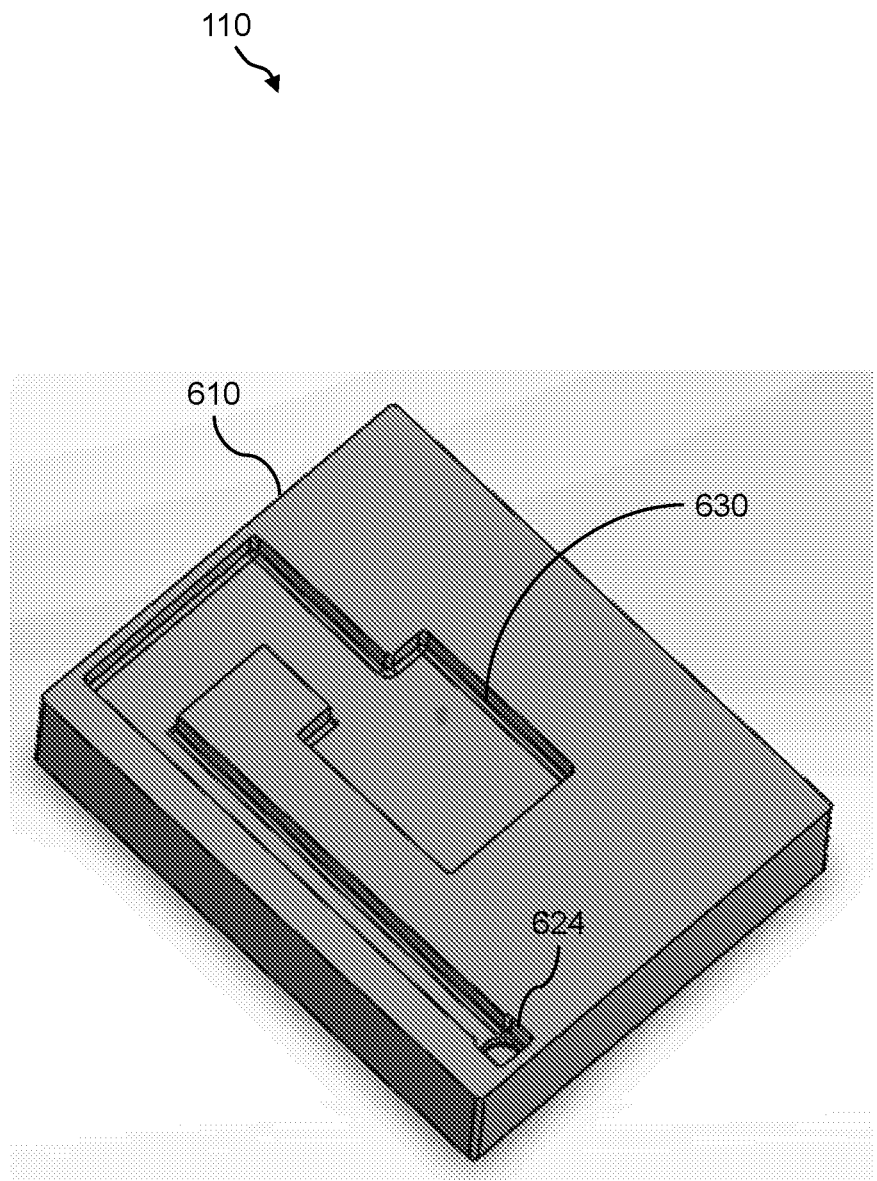

Referring now to FIG. 14 is a perspective view of the sensing base 610 only of the urine sensing device 110 shown in FIG. 9. Namely, FIG. 9 shows a view of urine sampling chamber 630, showing the path of the urine being sampled after it enters sensing base 610 of the urine sensing device 110.

Figure 15:
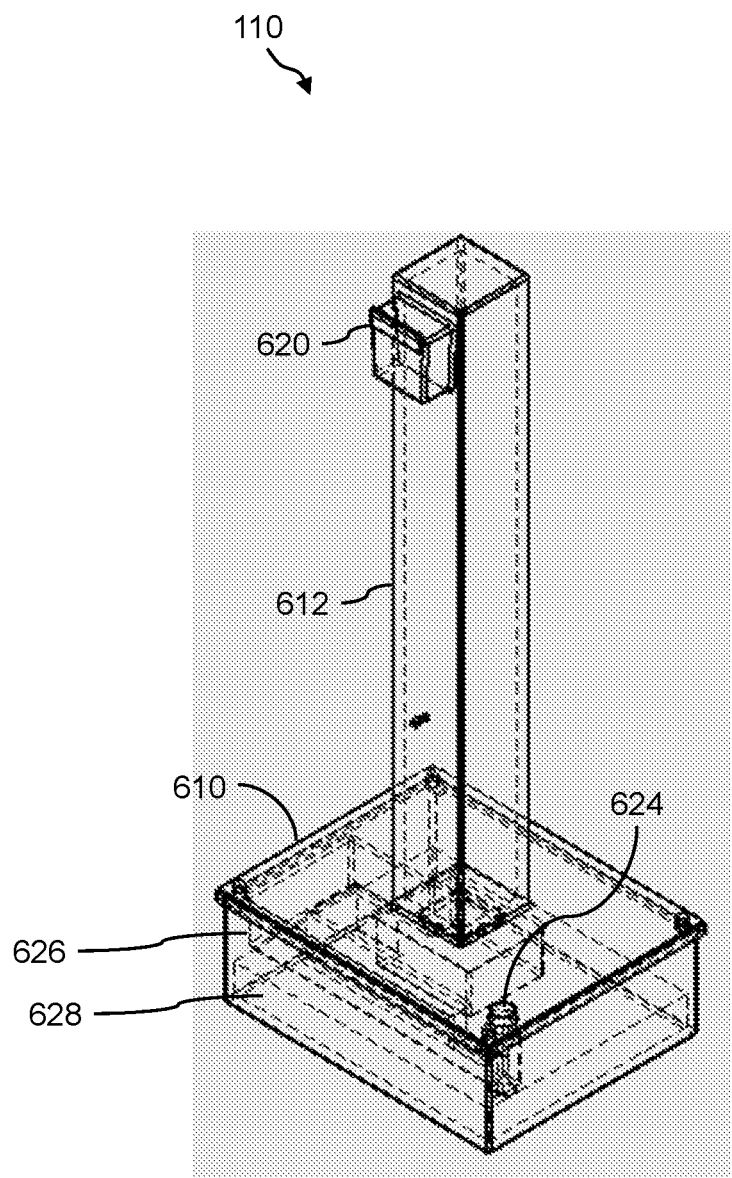
Figure 16:
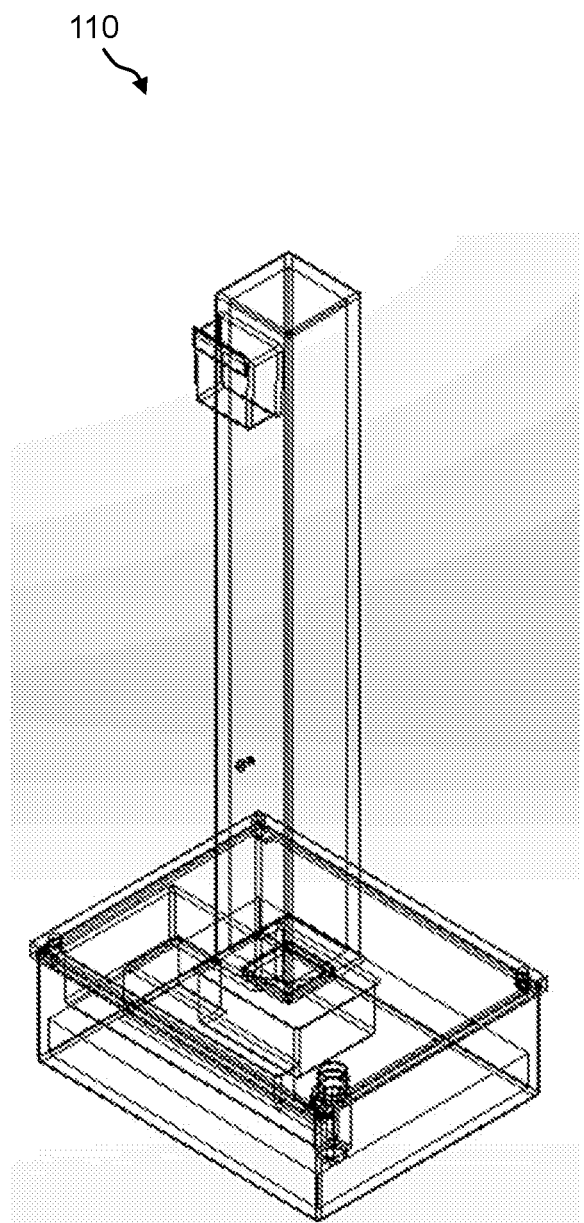

Referring now to FIG. 15 and FIG. 16 are perspective views of the urine sensing device 110 shown in FIG. 9. Namely, FIG. 15 and FIG. 16 show an example of how sodium sensing portion 628 is arranged in sensing base 610 of the urine sensing device 110.

The urine sensing device 110 shown in FIG. 7 through FIG. 16 features (1) automated methods of urine extraction from existing urine collection systems, (2) automated sodium sensing methods that do not rely on continuous flow or the use of multiple electrodes, and (3) built-in mechanisms, such as a vibration sonicator, for preventing protein build-up on the ion-selective electrode.

The urine sensing device 110 shown in FIG. 7 through FIG. 16 is not limited to measuring urine sodium levels only. Mechanisms can be provided to measure at least one urinary component other than sodium, such urine oxygen tension levels, urine creatinine levels, urine potassium levels, and urine chloride levels. Further, the sodium sensing function of urine sensing device 110 can be provided as a standalone device that is not combined with other mechanisms, such as a weight scale.

Referring now to FIG. 17, FIG. 18, and FIG. 19 is a front perspective view, a side perspective view, and a top down perspective view, respectively, of another example of urine sensing device 110 of the presently disclosed kidney function monitoring system 100. In this example, urine sensing device 110 includes a weight scale 1710, an interface 1720, and a stand 1730. The urine sensing device 110 may include a force transducer (not shown) for converting the force transferred to the weight scale into to a digital output signal indicating the weight of the urine collected in the urine collection vessel.

Weight scale 1710 can be any standard weight scale that has suitable accuracy and resolution to be used in kidney function monitoring system 100. In some embodiments, weight scale 1710 comprises a digital weight scale. In one example, weight scale 1710 is the Scout® Pro weight scale, model numbers SP6001, SP6000, or SP 4001], available from Ohaus Corporation (Parsippany, N.J.). Weight scale 1710 also includes, for example, a pair of wires 1722 (one for power, the other for the digital output signal).

Interface 1720 is customized to receive and hold stand 1730 in place over weight scale 1710 such that the centers of mass of the stand and weight scale are aligned. In particular, interface 1720 is designed to be positioned between the weight scale 1710 and stand 1730 and to transfer the force of stand 1730 and any contents thereof to weight scale 1710 for accurate weight measurement thereon. Interface 1720 includes a support member 1721 onto which stand 1730 rests, first alignment member 1722 and second alignment member 1724. First alignment member 1722 is positioned atop support member 1721 and interfaces with stand 1730 via opening 1740. Second alignment member 1724 is positioned underneath support member 1721 and interfaces with scale 1710 via its weighing platform (not shown). The first alignment member 1722 and second alignment member 1724 are positioned such that the center of mass of stand 1730 is aligned with respect to the center of mass of weight scale 1710. In one example, the underside of interface 1720 includes an alignment member 1724 for mating to the Scout® Pro weight scale.

Stand 1730 is any structure for positioning a urine collection vessel thereon, for example, a Foley bag and a urinometer (see FIG. 22A and FIG. 22B) so that the weight of urine therein can be transferred to interface 1720 and then to weight scale 1710. In this example, stand 1730 is U-shaped. Stand 1730 includes, in some embodiments, a base member 1732, a first wall member 1734, and a second wall member 1736. Stand 1730 can be formed of any lightweight, rigid, durable, and washable material, such as molded plastic or metal (e.g., aluminum, stainless steel). Further, base member 1732, first wall member 1734, and second wall member 1736 of stand 1730 can be, for example, about 0.2 to 20 cm thick.

In some embodiments, base member 1732 includes a first end 1746, a second end 1748, and an opening 1740 between the first end 1746 and second end 1748. In this example, first wall member 1734 extends radially from the first end 1746 of base member 1732, and is angled at less than 90 degrees with respect to a horizontal axis of base member 1732. The first wall member 1734 can be angled at any angle less than 90 degrees from perpendicular with respect to base member 1732 (e.g., angle α of FIG. 21) that will help place a urinometer mounted on stand 1730 within the line of sight of a clinician (e.g., anesthesiologist). In some embodiments, first wall member 1734 can be angled up to between about 85 degrees to 40 degrees from perpendicular with respect to base member 1732, with one example being 65 degrees.

In some embodiments, second wall member 1736 extends radially from the second end 1748 of base member 1732, and is arranged substantially perpendicular with respect to base member 1732. Optionally, a handle 1738 is provided on the upper edge of second wall member 1736. In some embodiments, the second wall member 1736 includes a handle 1738. Stand 1730 has an overall width dimension W (see FIG. 17), an overall height dimension H (see FIG. 18), and an overall depth dimension D (see FIG. 18). The width W, height H, and depth D of stand 1730 can be designed to specifications. In some embodiments, stand 1730 has an overall width W of between about 7 inches and 11 inches, an overall height H of between about 8 inches and 12 inches, and an overall depth D of between about 4 and 8 inches. In one example, stand 1730 has an overall width W of about 9.3 inches, an overall height H of about 10 inches, and an overall depth D of about 5.9 inches. In some embodiments, the heights of first wall member 1734 and second wall member 1736 are the same. In other embodiments, the heights of first wall member 1734 and second wall member 1736 are different. In some embodiments, the second wall member 1736 has a height that is greater than the height of the first wall member 1734. In some embodiments, the height of the second wall member 1736 is between at least 10 and 70 percent greater than the height of the first wall member. In some embodiments, the height of the second wall member 1736 is between at least 0.5 and 8 inches greater than the height of the first wall member.

The center of mass of urine sensing device 110 is along the vertical center axis of weight scale 1710, interface 1720, and stand 1730. Optionally, more mass can be added to the lower portion of stand 1730 to lower the center of gravity of entire device.

Further, an alignment feature (e.g., opening) 1740 can be provided in base member 1732 of stand 1730 for engaging with first alignment member 1722 of interface 1720. In some embodiments, the first alignment member 1722 comprises a protuberance that extends through opening 1740 of base member 1732 and securely holds stand 1730 in place on interface 1720. In some embodiments, the protuberance 1722 engages base member 1732 on at least a portion of the perimeter of the opening 1740. In the example embodiments shown in FIG. 18 and FIG. 19, protuberance 1722 engages at least four points of contact on the perimeter of opening 1740 of base member 1732. In some embodiments, protuberance 1722 engages at least three points of contact on the perimeter of opening 1740 of base member 1732, for example, when protuberance 1722 has a triangular shape (not shown). In other embodiments, the protuberance 1722 engages the base member 1732 on the entire perimeter of opening 1740, for example, when protuberance 1722 is configured with the same shape as the perimeter of opening 1740.

In one example, the first alignment member 1722 of interface 1720 is a square pedestal type feature and alignment feature 1740 of stand 1730 is an opening 1740 or through-hole for receiving the first alignment member 1722. In this way, proper positioning of stand 1730 with respect to weight scale 1710 is ensured for transferring the weight thereof.

In one example, first alignment member 1722 of interface 1720 is about 1.5 inches square and alignment feature 1740 of stand 1730 is about 2 inches in in diameter.

A set of foot pads 1742 (see FIG. 17) may be provided on the underside of base member 1732 of stand 1730. When stand 1730 is removed from interface 1720, foot pads 1742 allow stand 1730 to be freestanding. Further, a plurality of retaining members 1744 are provided on the outside surface of first wall member 1734 of stand 1730. Retaining members 1744 can be separately formed features that are adhered to stand 1730 or formed as an integral part of stand 1730. Retaining members 1744 are used to secure an urinometer. Namely, the urinometer can be hung on the edge of first wall member 1734 of stand 1730 as shown in FIG. 22A and FIG.

22B. Retaining members 1744 help prevent the urinometer from swinging from side-to-side when urine sensing device 110 is in use. Accordingly, in some embodiments, the first wall member 1734 comprises a first side aligned with a front face of the digital weight scale, and an opposite second side facing the second wall member 1736, and wherein the first side of the first wall member 1734 further comprises a plurality of retaining members 1744 for securing a urinometer thereto in such a way as to prevent the urinometer from swinging from side-to-side.

Referring now to FIG. 20A and FIG. 20B are perspective views of urine sensing device 110 of FIG. 17, FIG. 18, and FIG. 19 absent stand 1730 and showing interface 1720. In this example, interface 1720 is a flat plate that is about 5 inches square and is about 1 inch thick. Generally, the size and shape of interface 1720 can be tailored to fit any type or brand of weight scale 1710 as long as the center of mass is distributed across weight scale 1710. Further, in this example, interface 1720 includes first alignment member 1722, which is shown in FIG. 20A as a square pedestal type feature protruding from the upper surface of interface 1720. This square pedestal type feature is designed to be engaged (e.g., by pressure-fitting or snap-fitting) with opening 1740 of stand 1730. In one example, alignment feature 1722 is about 1.5 inches square and is about 0.4 inches high. In some embodiments, such as FIG. 20B which shows a bottom perspective view of interface 1720, second alignment member 1724 comprises a groove in support member 1721 that receives a perimeter of the platform (e.g., weighing platform) of weight scale 1710. In this way, the platform of weight scale (hidden) acts as a corresponding ridge to groove 1724 ensuring that interface 1720 is stably secured to weight scale 1710 (e.g., snap-fit or pressure-fit). FIG. 20B shows groove 1724 in the shape of a circle, however, groove 1724 can be custom tailored to have any shape that will enable groove 1724 to receive the perimeter of the platform of weight scale 1710. As will be appreciated by those skilled in the art, the shape of groove 1724 will depend on the shape of the platform. In some embodiments, second alignment member 1724 comprises a ridge on support member 1721 that encloses a perimeter of the platform, as shown in FIG. 20C. Second alignment member 1724 is shown in the shape of a circle, but the actual shape may vary, and will depend on the shape of the platform of the particular weight scale 1710.

Interface 1720 can be formed of any lightweight, rigid, durable, and washable material, such as plastic or metal (e.g., aluminum, stainless steel). In one example, interface 1720 can be formed using a three-dimensional (3D) printing process. In another example, interface 1720 can be formed of molded plastic.

Referring now to FIG. 21 is an exploded side view of urine sensing device 110 of FIG. 17, FIG. 18, and FIG. 19 and showing weight scale 1710, interface 1720, and stand 1730. In some embodiments, urine sensing device 110 includes a urine collection device 1750 hanging from the second wall member 1736 such that it is positioned in between the first wall member 1734 and the second wall member 1736, as is shown in FIG. 22A and FIG. 22B. In some embodiments, the urine collection vessel 1750 includes and is in fluid communication with a urinometer that is secured to the first wall member 1734.

Referring now to FIG. 22A and FIG. 22B are a front perspective view, and side perspective view, respectively, of urine sensing device 110 of FIG. 17, FIG. 18, and FIG. 19 with a urine collection vessel (Foley bag 1750 and a urinometer 1752) installed in/on stand 1730. Namely, the Foley bag 1750 sits in the space within stand 1730. The edge of the Foley bag 1750 can attach to handle 1738 of stand 1730. Optionally, prior to installing Foley bag 1750 and urinometer 1752 in/on stand 1730, a plastic bag or covering 1751 may be placed over urine sensing device 110 to cover substantially the entirety thereof. The purpose of the plastic bag or covering 1751 is simply to try to preserve the general cleanliness of urine sensing device 110. In some embodiments, the covering 1751 comprises a draw-string (not shown) for securing the covering 1751 around the weight scale 1710, the interface 1720, and the stand 1730. In some embodiments, the covering is disposable. In some embodiments, urine sensing device 110 includes a covering 1751 placed over the stand 1730, the interface 1720, and the weight scale 1710, in such a way that at least a portion of the covering 1751 hangs over and in between the first and second wall members to create a pocket 1753, as is shown in FIG. 22B. In some embodiments, a urine collection vessel (e.g., Foley bag 1750) is positioned in pocket 1753.

In practice, after weight scale 1710, interface 1720, and stand 1730 are assembled; and after the covering 1751 is placed over urine sensing device 110; and after the empty Foley bag 1750 and urinometer 1752 are installed in stand 1730; the weight scale 1710 is zeroed out so that any increase in weight is due only to urine collected in Foley bag 1750. Further, tubing of Foley bag 1750 can partially rest on handle 1738 to prevent the tubing from having dependent loops (e.g., tubing sags below rest of the bag). Further, having the height of first wall member 1734 less than the height of second wall member 1736 can also aid in preventing the tubing from having dependent loops.

The shape of stand 1730 and interface 1720 is not limited to that shown in FIG. 17 through FIG. 22. Referring now to FIG. 23A, FIG. 23B, FIG. 23C, and FIG. 23D are side views of examples of other shapes of stand 1730 and interface 1720 of urine sensing device 110. In a first example and referring now to FIG. 23A, first wall member 1734 is not angled. Namely, both first wall member 1734 and second wall member 1736 are arranged substantially perpendicular with respect to base member 1732. In a second example and referring now to FIG. 23B, the lower portion of stand 1730 has angled sidewalls leading to base member 1732. Further, interface 1720 forms a trough (not a flat plate) that is shaped to receive this stand 1730 design. In a third example and referring now to FIG. 23C, stand 1730 has a V-shaped lower portion. Further, interface 1720 forms a V-shaped trough (not a flat plate) that is shaped to receive this stand 1730 design. In a fourth example and referring now to FIG. 23D, U stand 1730 has a halfpipe-shaped lower portion. Further, interface 1720 forms a halfpipe-shaped trough (not a flat plate) that is shaped to receive this stand 1730 design. Yet other shapes of stand 1730 and interface 1720 are possible as long at the center of mass can be transferred to weight scale 1710.

Referring now to FIG. 24 is a block diagram of an example self-learning AKI risk algorithm 122 of the presently disclosed kidney function monitoring system 100 for early detection of AKI. AKI risk algorithm 122 is a patient-specific algorithm that incorporates in real-time patient-specific pre-operative risk factors, fluids and medications administered to a patient, and real-time measurements of urine parameters, such as urine output volume/flow, optionally levels of at least one urinary component (e.g., at least one urinary component selected from the group consisting of urine sodium levels, urine oxygen tension levels, urine creatinine levels, urine potassium levels and urine chloride levels, and combinations thereof), and/or real-time changes in at least one intra-operative risk factor for acute kidney injury, and using these inputs can correlate such urine parameters to kidney function in real-time. That is, AKI risk algorithm 122 uses a combination of continuous urine output and optionally monitoring of at least one urinary component (e.g., sodium monitoring) and a support vector machine and decision trees to analyze time-dependent patterns and variations, while taking into account fluids, medications, and individual patient risk factors, and verifying the urine analysis against established thresholds that are a measure of AKI. In other words, AKI risk algorithm 122 uses the combination of urinalysis, pre-operative risk factors, fluids, medications, and real-time intra-operative hemodynamic thresholds (mean arterial pressure (MAP), nadir oxygen delivery (DO2)) for specific indication of kidney perfusion. Then, AKI risk algorithm 122 calculates an AKI risk score and generates alerts based on weighting of the acute kidney injury factors. The output of AKI risk algorithm 122 is real-time AKI risk %. As shown in the examples in FIG. 2 and FIG. 3, the real-time AKI risk % is displayed on AKI risk GUI 124. AKI risk GUI may also categorize real-time risk as low, moderate, or high based on threshold risk percentages or scores calculated for a patient based on an AKI risk algorithm 122 optimized for a specific patient 105 as a result of the self-learning capability of AKI risk algorithm 122.

AKI risk algorithm 122 categorizes real-time risk as low (green alert color), moderate (yellow alert color) or high (red alert color), and assigns risk scores or percentages based on a patient-specific weighting of acute kidney injury risk factors. The AKI risk algorithm 122 may compare the patient-specific weighting of acute kidney injury risk factors to established or accepted AKI patient risk profiles. Exemplary AKI patient risk profiles for low, medium, and high AKI risk patients are as follows.

Example values of a low AKI patient risk profile would be a patient whose preoperative STS risk analysis yields less than 5% chance for adverse effects including mortality risk, morbidity or mortality, long length of stay, permanent stroke, prolonged ventilation, DSW infection and Reoperation, while precedence will be given to a less than 0.5% chance of Renal Failure. Intraoperative MAP levels would drop below 60 mmHg for no more than 10 minutes, while $DO_2$ levels would be no less than 250 mL $O_2$/min/m$^2$ with an average last pressor dose before leaving the OR less than 0.03 mcg/kg/min.

An illustrative moderate AKI risk patient would be a patient whose preoperative STS risk analysis yields less than 7% chance for adverse effects including mortality risk, morbidity or mortality, long length of stay, permanent stroke, prolonged ventilation, DSW infection and Reoperation, while precedence will be given to a less than 2% chance of Renal Failure. Intraoperative MAP levels would drop below 60 mmHg for no more than 15 minutes, while $DO_2$ levels would be no less than 235 mL $O_2$/min/m$^2$ with an average last pressor dose before leaving the OR greater than 0.03 mcg/kg/min.

An illustrative high AKI risk patient would be a patient whose preoperative STS risk analysis yields greater than 7% chance for adverse effects including mortality risk, morbidity or mortality, long length of stay, permanent stroke, prolonged ventilation, DSW infection and Reoperation, while precedence will be given to a greater than 2% chance of Renal Failure. Intraoperative MAP levels would drop below 60 mmHg for 15 minutes or more, while $DO_2$ levels would be less than 235 mL O2/min/m$^2$ and especially less than 225 mL $O_2$/min/m$^2$ with an average last pressor dose before leaving the OR greater than 0.03 mcg/kg/min.

Preferably, AKI risk algorithm 122 calculates a catheterized patient's 105 risk of developing acute kidney injury based on a weighting of various acute kidney injury risk factors. Exemplary acute kidney injury risk factors weighted by the AKI risk algorithm 122 in real-time for the continuous assessment of a catheterized patient's 105 AKI risk include, without limitation, the pre-operative Society of Thoracic Surgeon (STS) Risk Factors; KDIGO, RIFLE, or AKIN Criteria for Urine Output; KDIGO/AKIN Criteria for Serum Creatinine; volumetric flow rate calculations based on baseline urine density, pre-operative patient weight, and real-time second to second fluctuations in weight of the urine collection vessel; real-time urine output adjusted for changes due to medication and/or fluid administered to the catheterized patient; real-time levels of at least one urinary component adjusted for changes due to medication and/or fluid administered to the catheterized patient; real-time changes in the at least one intra-operative risk factor indicative of acute kidney injury, and combinations thereof.

One input to AKI risk algorithm 122 is pre-operative STS Risk Factors. the STS National Database has been reviewed (see, e.g., Shahian D M et al, "The Society of Thoracic Surgeons 2008 Cardiac Surgery Risk Models: part 1—coronary artery bypass grafting surgery" in Ann Thorac Surg 2009 July; 88(1 Suppl):S2-22; and Shahian D M et al, "The society of thoracic surgeons national database" in Heart 2013; 99(20):1494-501). Pre-operative STS Risk Factors include, for example, considerations including the planned, unplanned, complicated, or unexpected nature of a Coronary Artery Bypass operation, whether or not a valve is being altered in the surgery, whether or not another cardiac procedure is indicated, if the patient is admitted with a ventricular assist device (VAD), if a VAD is implanted during current hospitalization, if an aortic procedure is to be performed, if an atrial fibrillation procedure is performed, if the current case is canceled, if there are other non-cardiac related operations, patient age, gender, height, and weight, if hemodynamic data such as ejection fraction is done, if a patient had experienced heart failure within 2 weeks, patient race, if the patient is Hispanic, Latino, or Spanish Ethnicity, if the patient is in renal failure or on dialysis, the patient's last creatinine level, the occurrence of certain cardiac symptoms at time of current admission (stable angina, unstable angina, angina equivalent, non-ST Elevation myocardial infarction, ST Elevation myocardial infarction, other), the occurrence of same cardiac symptoms parenthetically listed at time of surgery, if a prior myocardial infarction existed, if cardiac arrhythmia is present, if patient has chronic lung disease, if patient has cerebrovascular disease, if peripheral arterial disease is present, if patient has diabetes, if hypertension is present, whether or not the patient is immunocompromised, if endocarditis is present, if coronary disease exists, the nature of the surgery (elective, urgent, emergent, emergent salvage), if the patient has been resuscitated (within one hour of the start of the procedure, or between 1 and 24 hours), if the patient is experiencing cardiogenic shock, if patient has an intra-aortic balloon pump installed, if patient is on inotropes, if patient has had a previous cardiac intervention, if mitral valve or aortic disease is present, the degree of mitral valve insufficiency, the degree of tricuspid insufficiency, the degree of aortic insufficiency, and the incidence of current surgery (first, second, etc. cardiovascular surgery). Pre-operative STS Risk Factors can be observed by a user (e.g., a nurse), and manually entered into the portable monitoring system 120 by the user when prompted by AKI risk GUI 124. In some embodiments, the AKI risk GUI 124 displays a form prompting the user to enter pre-operative STS Risk Factors, such as the Online STS Adult Cardiac Surgery Risk Calculator available on the World Wide Web. In some embodiments, the AKI risk GUI 124 includes a link or button that redirects the user to the Online STS Adult Cardiac Surgery Risk Calculator where the user can enter pre-operative STS Risk Factors, and the entered factors are stored in the patient database 154 for the patient 105.

The ordinarily skilled artisan will appreciate that pre-operative STS Risk Factors are one of a variety of pre-operative cardiac surgery risk-stratification models that can be factored by AKI risk algorithm 122 while calculating AKI risk for any given patient 105. The particular risk-stratification model employed may depend on a variety of factors, for example, the type of cardiac surgery for which AKI risk is being predicted. Exemplary cardiac surgery risk-stratification models of use in the AKI risk algorithm 122 have been reviewed by Prins et al. (see, e.g., Table 1 of "Cardiac surgery risk-stratification models," *Cardiovasc J. Afr.* 2012; 23(3):160-164, incorporated herein by reference in its entirety). Accordingly, in some embodiments, the AKI risk algorithm 122 alternatively, or additionally, weights a cardiac surgery risk-stratification model other than STS Risk Factors, such as the European System for Cardiac Operative Risk Evaluation, or the Parsonnet score.

Another input to AKI risk algorithm 122 is Kidney Disease: Improving Global Outcomes (KDIGO) Criteria for Urine Output. (KDIGO) Criteria for Urine Output includes, for example, stratification of acute kidney injury in increasing severity stages. Stage 1 is defined as <0.5 ml/kg/h for 6-12 hours, stage 2 is defined as <0.5 ml/kg/h for >12 hours, and stage three is defined as <0.3 ml/kg/h for more than 24 hours, or anuria for more than 12 hours. AKI risk algorithm 122 automatically and continuously factors and weights the KDIGO Criteria for Urine Output based on real-time inputs obtained for urine output by the urine sensing device 110 and optionally real-time inputs obtained for the at least one urinary component by the at least one ionic species sensor.

Another input to AKI risk algorithm 122 is KDIGO/AKIN Criteria for Serum Creatinine. KDIGO/AKIN Criteria for Serum Creatinine includes, for example, stratification of acute kidney injury in increasing severity stages. AKI Stage 1 is defined as a 50%-99% increase in serum creatinine from baseline, or an acute increase of 0.3 mg/dL or more from baseline. AKI Stage 2 is defined as a 100%-199% increase in serum creatinine from baseline. AKI Stage 3 is defined as a 200% or greater increase in serum creatinine from baseline, or any new need for hemodialysis. AKI risk algorithm 122 automatically and continuously factors and weights the KDIGO/AKIN Criteria for Serum Creatinine based on real-time inputs obtained for serum creatinine, for example, by the levels determined in lab results from analysis of patient's drawn blood.

Yet another input to AKI risk algorithm 122 is volumetric flow rate calculations. Volumetric flow rate calculations include, for example, the (1) assumed or calculated baseline urine density, (2) urine bag weight, (3) pre-operative patient weight, and (4) time (in seconds). It should be appreciated that such volumetric flow rate calculations are obtained by and manually entered by a user into the portable monitoring device 120 via the AKI risk GUI 124 (e.g., baseline urine density, pre-operative patient weight, etc.) or may be automatically calculated continuously in real-time based on the measurements obtained by urine sensing device 110 (e.g., second to second urine output volume/flowrate), and optionally at least one ionic species sensor (e.g., a sodium sensor).

Yet another input to AKI risk algorithm 122 is at least one intra-operative factor for acute kidney risk. At least one intra-operative factor for acute kidney risk can be, for example, (1) real-time urine output from urine sensing device 110, (2) changes to the urine output due to fluids and/or medications, (3) optionally real-time urine sodium level from urine sensing device 110, (4) optionally changes to the urine sodium level due to fluids and/or medications, (5) real-time cerebral oximetry autoregulation thresholds, (6) Nadir DO2 level from the perfusion pump, and (7) mean arterial blood pressure (MAP) from the anesthesia monitor, or other patient monitoring system.

In one example, in kidney function monitoring system 100, HL7 communication protocol (Capsule Technologies) can be used to receive data from existing devices for intra-operative factors.

An aspect of the portable monitoring device 120, which is a multi-parameter monitoring device, of the presently disclosed kidney function monitoring system 100 is the self-learning capability of the AKI risk algorithm 122 that translates a weighting of pre-operative and real-time inputs into an AKI risk score. The self-learning algorithm adjusts the weighting of the acute kidney injury risk factors for each catheterized patient 105 based on the relative significance of the acute kidney injury risk factors toward influencing actual kidney injury outcomes of other catheterized patients presenting with similar acute kidney injury risk factors. This is achieved in part by provision of a patient database 154 in electronic communication (e.g., networked via a server 152, e.g., a cloud server) with the portable monitoring device 120. The patient database 154 includes patient-specific records and/or information for each catheterized patient 105 whose risk of developing acute kidney injury (e.g., AKI risk score) was calculated with AKI risk algorithm 122. Examples of such information includes, without limitation, a calculation of the patient's acute kidney injury risk, acute kidney injury risk factors present in the patient, weighting of the patient's acute kidney injury risk factors, and an indication of whether the patient developed acute kidney injury, to name a few.

Referring now to FIG. 25 is an image of an operating room and an example of using the presently disclosed kidney function monitoring system 100 for early detection of AKI. Namely, FIG. 25 shows, for example, the urine sensing device 110 shown in FIG. 17 through FIG. 22 connected to portable monitoring device 120, which is a tablet device. As shown in the example of FIG. 25, urine sensing device 110 continuously monitors urine output flowing through a catheter (e.g., Foley catheter) of a catheterized patient into a urine collection vessel 107 (a Foley bag) installed in stand 1730 of urine sensing device 110. The angled portion of stand 1730 allows any user, such as the anesthesiologist, to easily view the urinometer 1752 hanging thereon.

FIG. 25 also shows the anesthesia monitor as an example of an external information source 128 (i.e., an external device) connected to portable monitoring device 120. Anesthesia monitor 128 (and/or another patient monitor) continuously monitors in real-time at least one of a mean arterial pressure of the catheterized patient, a medication administered to the catheterized patient, a fluid administered to the catheterized patient, and combinations thereof. AKI risk GUI 124 of portable monitoring device 120 can display, for example, the information shown in FIG. 2 and/or FIG. 3. Further, FIG. 25 shows that portable monitoring device 120 can be provided in a convenient carrying case 121. Further, a clip may be provided on the back of portable monitoring device 120 for clipping onto an IV pole in the operating room.

Referring now to FIG. 26 is a flow diagram of an example of a method 2600 of using the presently disclosed kidney function monitoring system 100 for early detection of AKI. Method 2600 may include, but is not limited to, the following steps.

At a step 2610, is installed in line with the Foley system. For example, just before the Foley catheter is inserted into the patient 105, a circulating nurse attaches urine sensing device 110 to the Foley system between the Foley catheter and urine collection vessel 107 (e.g., Foley bag 1750 (see FIG. 22)).

At a step 2615, the patient is catheterized using the Foley catheter. For example, before surgery, the Foley catheter is inserted into patient 105.

At a step 2620, the initial urine density (i.e., specific gravity) measurement is acquired. For example, as patient 105 is being prepped for surgery, the surgical nurse will measure the patient 105's initial urine density (specific gravity) using a dipstick on a small urine sample. If this value is unattainable, the nurse can assume that urine density is normal, which means that it is within the range of 1.003-1.035 g/cm$^3$ for all patients. Density should approach 1.0 g/cm$^3$ (density of water) over time as the amount of diuretics given to the patient increases. Accordingly, a maximum error of about +/−0.035 g/cm$^3$ must be taken into account.

At a step 2625, urine sensing device 110 is connected to portable monitoring device 120. For example, portable monitoring device 120 is attached to the anesthesiologist's stand, where it can be controlled and monitored by the anesthesiologist throughout the course of the surgical procedure. Portable monitoring device 120 can be connected via a cable and/or wirelessly to the anesthesiologist's monitor screen to capture fluid and medication input data.

At a step 2630, portable monitoring device 120 is placed within view/reach of the anesthesiologist. For example, the nurse ensures that urine sensing device 110 is connected to portable monitoring device 120 via electric cables and/or wirelessly.

At a step 2635, to portable monitoring device 120 is connected to the anesthesiologist's monitor to capture fluid and medication input data.

At a step 2640, kidney function monitoring system 100 is initiated in order to start the timer and data collection. For example, once the cardiac surgery begins, the anesthesiologist presses the start button on portable monitoring device 120 to start the timer and begin collecting data from urine sensing device 110.

At a step 2645, readings from kidney function monitoring system 100 are continuously observed by, for example, the anesthesiologist. For example, the following factors can be reported back to the user (e.g., the anesthesiologist) via AKI risk GUI 124 of portable monitoring device 120 and/or any other visual, audible, and/or tactile indicators of portable monitoring device 120:

a) Minute-to-minute urine output, reported to clinician in graph form (flow vs time), as shown, for example, in FIG. 2 and FIG. 27;
 b) Fluids administered to the patient by the anesthesiologist and perfusionist, as per the anesthesiologist's monitor screen, as shown in FIG. 27;
   a. Includes fluid name/type and volume over time
 c) Medications administered to the patient by the anesthesiologist and perfusionist, as per the anesthesiologist's monitor screen; and
   a. Includes medication name/type and dosage over time.

At a step 2650, portable monitoring device 120 is disconnected from the anesthesiologist's monitor, allowing portable monitoring device 120 to remain at patient's bedside. For example, at the end of the surgical procedure, portable monitoring device 120 can be detached from the anesthesiologist stand and transferred to the patient's bedside in the ICU, where the intensivist will be in charge of operating portable monitoring device 120.

In one particular aspect, the presently disclosed subject matter includes a method for real-time assessment of a patient's risk of developing acute kidney injury, the method comprising: (a) connecting a catheter of a catheterized patient to a urine collection vessel hanging on or positioned on a urine sensing device, wherein the urine sensing device measures second to second urine output, and optionally at least one ionic species sensor for second to second monitoring of at least one urinary component; (b) continuously monitoring urine output of said catheterized patient by measuring real-time second to second fluctuations in urine output (e.g., with a gravimetric sensor); (c) optionally continuously monitoring a level of the at least one urinary component by measuring real-time second to second fluctuations in the level of the at least one urinary component with the at least one ionic species sensor; (d) transmitting the continuously monitored real-time fluctuations in urine output measured in (b) and optionally transmitting the continuously monitored real-time fluctuations in the level of the at least one urinary component measured in (c) to a patient monitoring device, wherein the patient monitoring device comprises: (i) a communications interface for automatically receiving the continuously monitored real-time fluctuations transmitted in (d); (ii) a non-transitory computer readable storage medium having computer readable program code embodied thereon for executing an acute kidney injury risk algorithm that calculates the catheterized patient's risk of developing acute kidney injury as a percentage of the likelihood that the catheterized patient will develop acute kidney injury; and (iii) a graphical user interface comprising means for prompting a user to input pre-operative patient information; (e) calculating the catheterized patient's risk of developing acute kidney injury as a percentage of the likelihood that the catheterized patient will develop acute kidney injury; and (f) displaying through the graphical user interface the catheterized patient's risk of developing acute kidney injury as a percentage of the likelihood that the catheterized patient will develop acute kidney injury. In some embodiments, the method further includes continuously monitoring at least one intra-operative risk factor indicative of acute kidney injury by measuring real-time second to second changes in at least one intra-operative risk factor indicative of acute kidney injury using an external device or external information source described herein. In some embodiments, the method further includes automatically receiving, via the communications interface, the measured real-time second to second changes in at least one intra-operative risk factor indicative of acute kidney injury. In some embodiments, the method further includes displaying via graphical user interface at least one of real-time second to second urine output, real-time levels of at least one urinary component, real-time input comprising the at least one intra-operative risk factor indicative of acute kidney injury, real-time second to second fluctuations in urine output, optionally real-time second to second fluctuations in levels of the at least one urinary component, real-time second to second changes in the at least one intra-operative risk factor indicative of acute kidney injury, a plot of urine weight over time, an AKI risk score in the form of a numerical percentage, alert color, or literary instruction, and combinations thereof. In some embodiments, the method includes adjusting the weighting of the acute kidney injury risk factors for each catheterized patient via the acute kidney injury risk algorithm based on the relative significance of the acute kidney injury risk factors toward influencing outcomes of other catheterized patients presenting with similar acute kidney injury risk factors. It should be appreciated that adjusting of the weighting of the acute kidney injury risk factors occurs in real time via the presently disclosed AKI risk algorithm due to its self-learning capabilities. In that regard, adjustment of weighting of the factors occurs perioperatively, that is before, during, and after surgery, all in real-time AKI risk algorithm is running simultaneously and independently on different portable monitoring devices to assess a plurality of patient's AKI risk. In some embodiments, the method for real-time assessment of a patient's AKI risk includes storing in a patient database in communication with the portable monitoring device, for each catheterized patient, calculations of the patient's acute kidney injury risk, the acute kidney injury risk factors for the patient, the weighting of the patient's acute kidney injury risk factors, an indication of whether the patient developed acute kidney injury, and any other information that would enable the presently disclosed self-learning AKI risk algorithm to optimize its ability to accurately predict AKI risk for each individual patient assessed.

The presently disclosed kidney function monitoring system 100 and method 2600 can be used to provide substantially real-time continuous monitoring of both urine output and a functional biomarker, such as urine sodium levels. Kidney function monitoring system 100 and method 2600 uses the combination of real-time continuous urine output and urine sodium monitoring and a self-learning algorithm (e.g., AKI risk algorithm 122) that analyzes time-dependent patterns and variations. Kidney function monitoring system 100 and method 2600 also uses the combination of urine analysis in AKI risk algorithm 122 with pre-operative risk factors, fluids and medications, plus two real-time intra-operative hemodynamic thresholds that are independent indicators of AKI, to provide a more specific and direct indication of kidney perfusion. The combination of each of these elements are used to calculate a kidney injury risk score and subsequent alerts.

Aspects of the presently disclosed subject matter involve assessing AKI risk of a patient (i.e., a catheterized patient) 105. The systems (e.g., 100) and methods (e.g., 2600) of the present disclosure can be used to assess AKI risk of any patient, including without limitation, a patient undergoing, or scheduled to undergo, coronary artery bypass grafting, a patient admitted with a ventricular assist device (VAD), a patient requiring implantation of a VAD during hospitalization, a patient undergoing, or scheduled to undergo, an aortic procedure, a patient undergoing, or scheduled to undergo, an atrial fibrillation procedure, a patient undergoing, or scheduled to undergo, a non-cardiac related operation, a patient that suffered from heart failure within 2 weeks of admission for cardiac surgery, a patient of Hispanic, Latino, or Spanish Ethnicity, a patient in renal failure, a patient on dialysis, a patient presenting with a cardiac symptom at time of admission for cardiac surgery selected from the group consisting of stable angina, unstable angina, angina equivalent, non-ST Elevation myocardial infarction, ST Elevation myocardial infarction, a patient presenting with a cardiac symptom at time of cardiac surgery selected from the group consisting of stable angina, unstable angina, angina equivalent, non-ST Elevation myocardial infarction, ST Elevation myocardial infarction; a patient with a history of prior myocardial infarction, a patient diagnosed with or presenting symptoms of cerebrovascular disease, a patient diagnosed with or presenting symptoms of arterial disease, a patient diagnosed with or presenting symptoms of a cardiac arrhythmia, a patient diagnosed with, presenting symptoms of, or having a family history of hypertension, a patient diagnosed with, presenting symptoms of, or having a family history of diabetes, an immunocompromised patient, a patient diagnosed with, presenting symptoms of, or having a family history of endocarditis, a patient diagnosed with, presenting symptoms of, or having a family history of coronary disease, a patient resuscitated within one hour of the start of a surgical procedure, such as cardiac surgery, a patient resuscitated within between one hour and 24 hours of the start of a surgical procedure, such as cardiac surgery, a patient experiencing cardiogenic shock, a patient having an intra-aortic balloon pump installed, a patient prescribed with or taking inotropes, a patient having a previous history of cardiac intervention, a patient presenting with mitral valve disease, a patient presenting with aortic disease, a patient experiencing a mitral valve insufficiency, a patient experiencing tricuspid insufficiency, a patient experiencing aortic insufficiency, and combinations thereof.

In summary, the value of kidney function monitoring system 100 that comprises urine sensing device 110 and portable monitoring device 120 is seen with its real-time automated measurements of urine output, with concurrent tracking of fluid and medication inputs. Urine sensing device 110 substantially removes the component of human error, providing greater accuracy and reliability, and it reduces the manual workload on the anesthesiologist. Recent studies have demonstrated that minute-to-minute changes in urine output flow are important indicators of renal blood flow and kidney function (see, e.g., Otero A et al, "On the minute by minute variations of urine output: a study in a porcine model" J Nephrol 2014 February; 27(1): 45-50).

Thus an immediate value of kidney function monitoring system 100 can be seen by the staff in the cardiac operating room. In particular, kidney function monitoring system 100 is extremely valuable to perfusionists and anesthesiologists who can now have power to change outcomes. Further, the value of kidney function monitoring system 100 can be seen by ICU staff, where intensivists and nurses can have more knowledge about individual patient conditions to allow more directed care.

Figure 28:
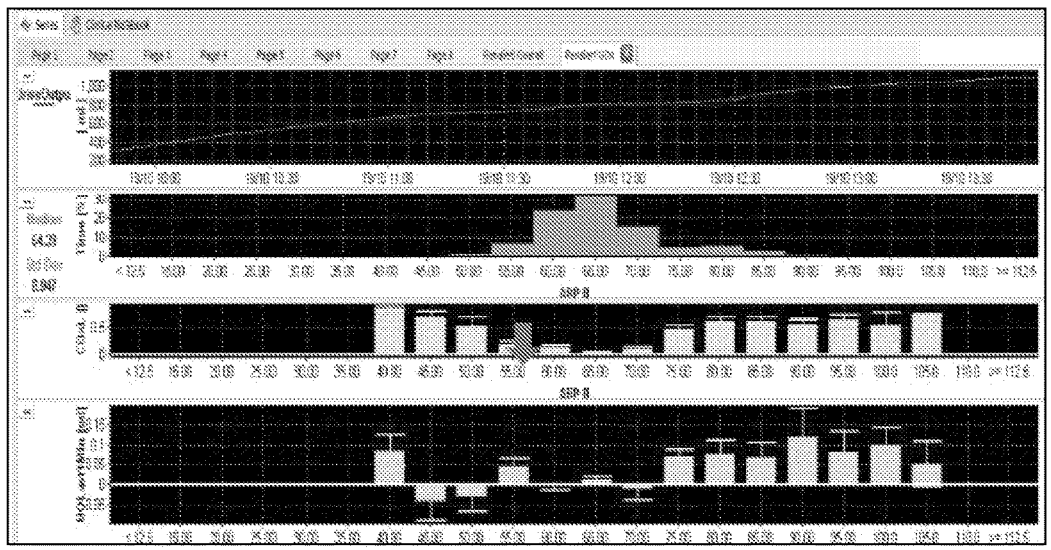

Referring now to FIG. 28 is another view of AKI risk GUI 124 showing a plot of minute-to-minute urine output and blood pressure monitoring. Namely, FIG. 28 shows several plots. For example, a plot of urine output, a plot of percent time spent at each blood pressure bin, a plot of urine produced at different blood pressures, and a plot of urine output in last 15 minutes vs blood pressure.

Figure 29:
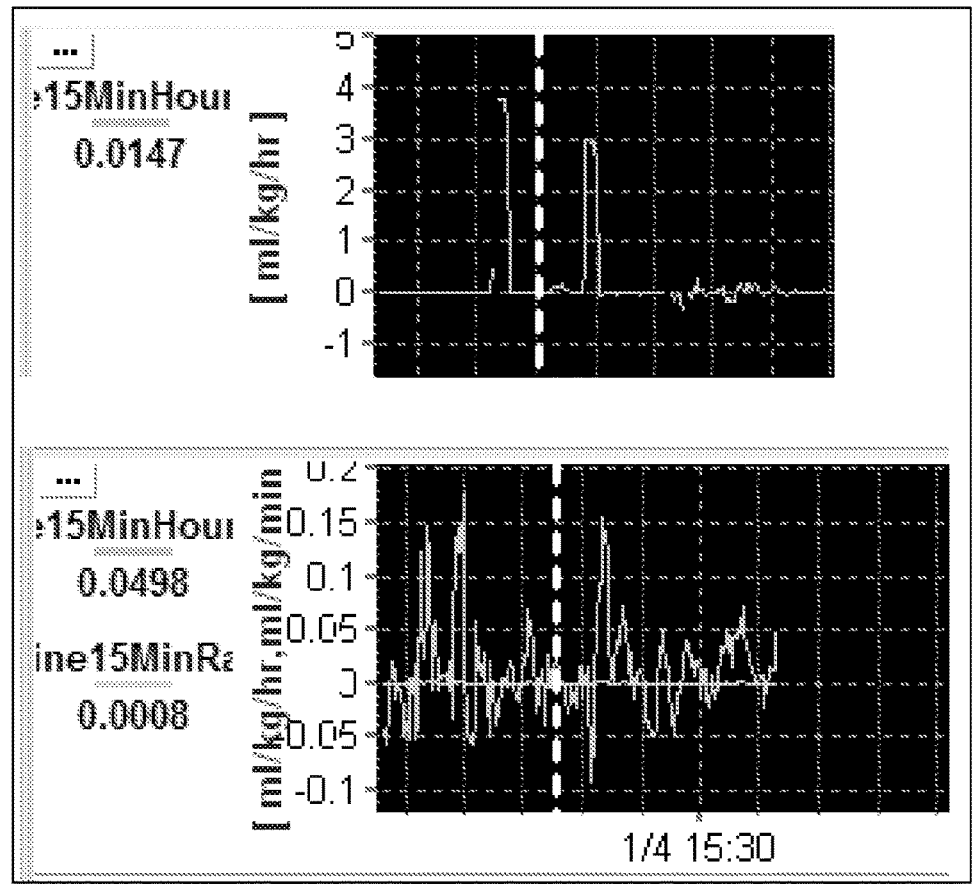
Figure 30:
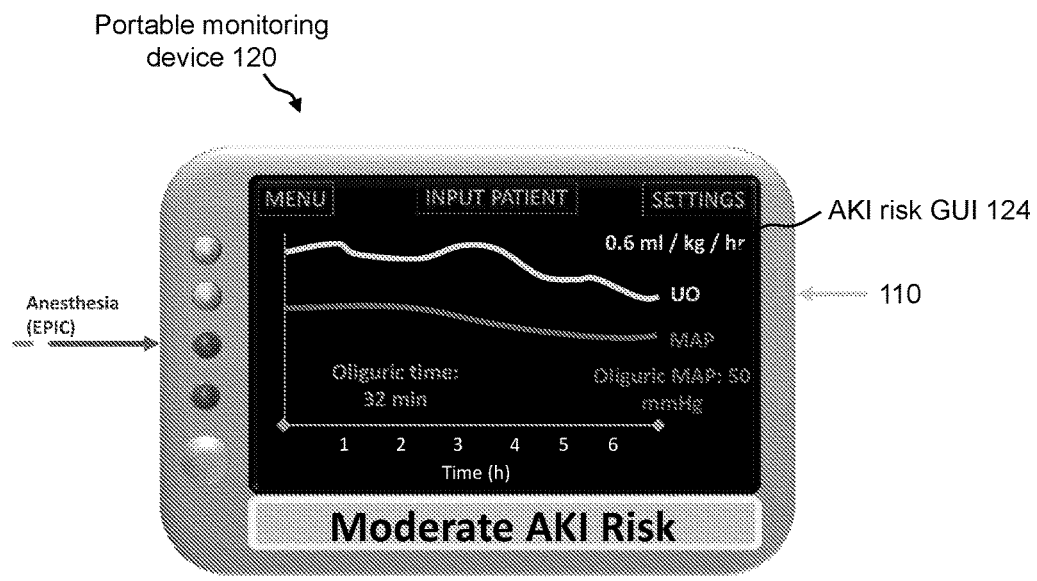
Figure 31:
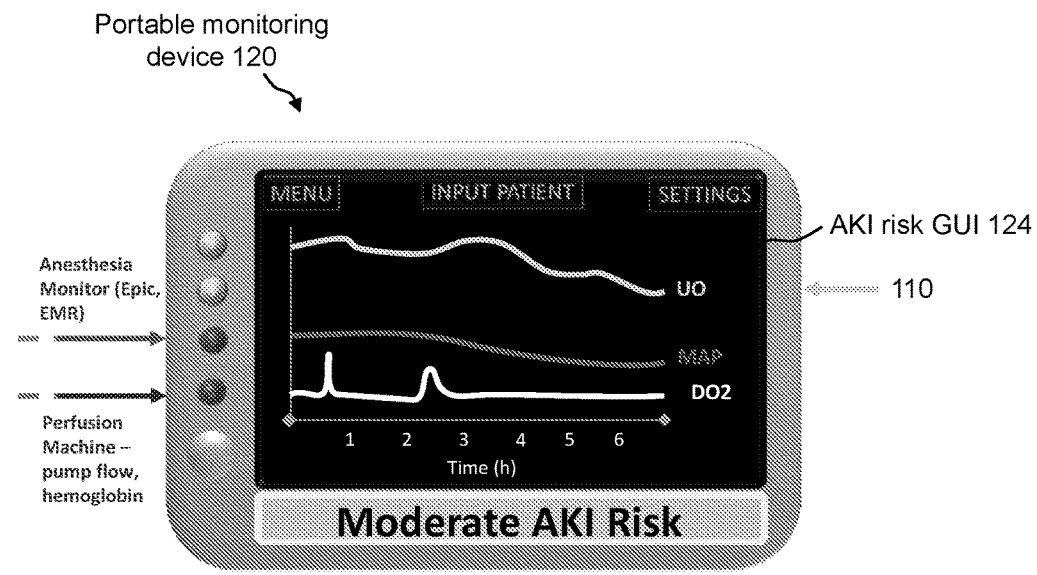

Referring now to FIG. 29 is another view of AKI risk GUI 124 showing a plot of real time urine output rates based on urine outputs in last 15 minutes (or 5 or 10 or 30). Values can be reported in ml/kg/hr or ml/kg/min. Referring now to FIG. 30 is another view of AKI risk GUI 124 showing a plot of the urine outflow vs anesthesia. Referring now to FIG. 31 is another view of AKI risk GUI 124 showing a plot of the urine outflow vs anesthesia vs perfusion machine output.

EXAMPLE

Referring now to FIG. 32 through FIG. 46 is an example of using the presently disclosed kidney function monitoring system 100. In this example, the urine sensing device 110 shown in FIG. 17 through FIG. 22 was utilized. Further, this example illustrates an example of signal filtering with respect to the signal returned from the urine sensing device 110, wherein certain signal anomalies may exist, for example, due to accidental movement of the urine sensing device (e.g., bumping).

Normalizing—Places where kidneys are oliguric and any increase or decrease in blood pressure (BP) would not affect urine output (UO), urinary output index, close to zero theoretically, where increasing, any increase in BP would increase UO, UOx would be more positive and totally linear would be 1.

Correlations over 1 minute, 5 minute, 10 minutes.

Figure 32:
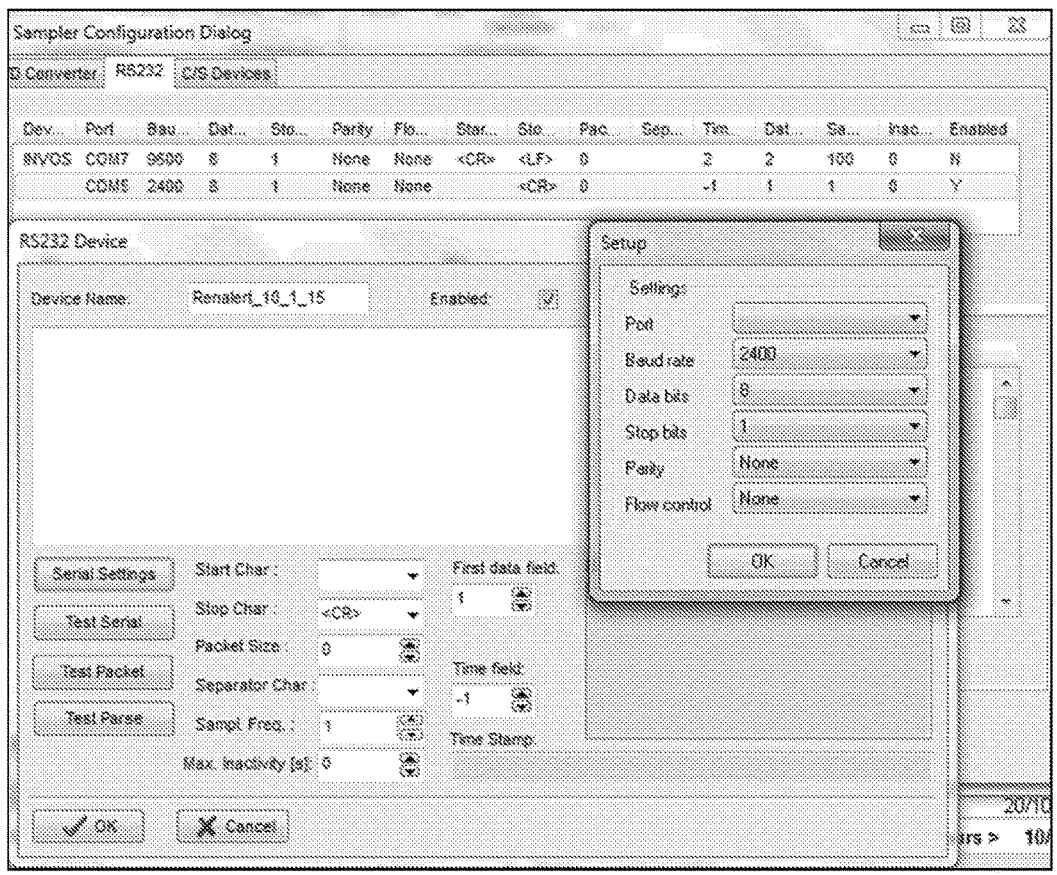

In FIG. 32, AKI risk GUI 124 shows the setup of the weight scale 1710 of urine sensing device 110.

Figure 33:
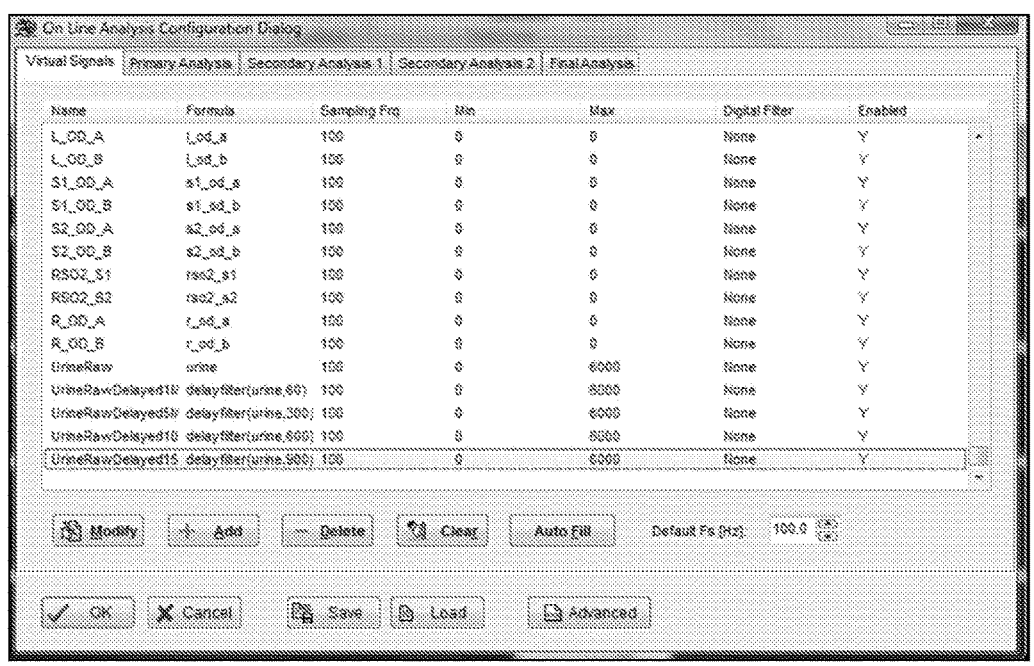

In FIG. 33, AKI risk GUI 124 shows an on line signal analysis—Virtual signals: Reading in weight measurements at 100 Hz. Delayed signals at 1 min, 5 min, 10 min, 15 min for future rate calculations.

Figure 34:
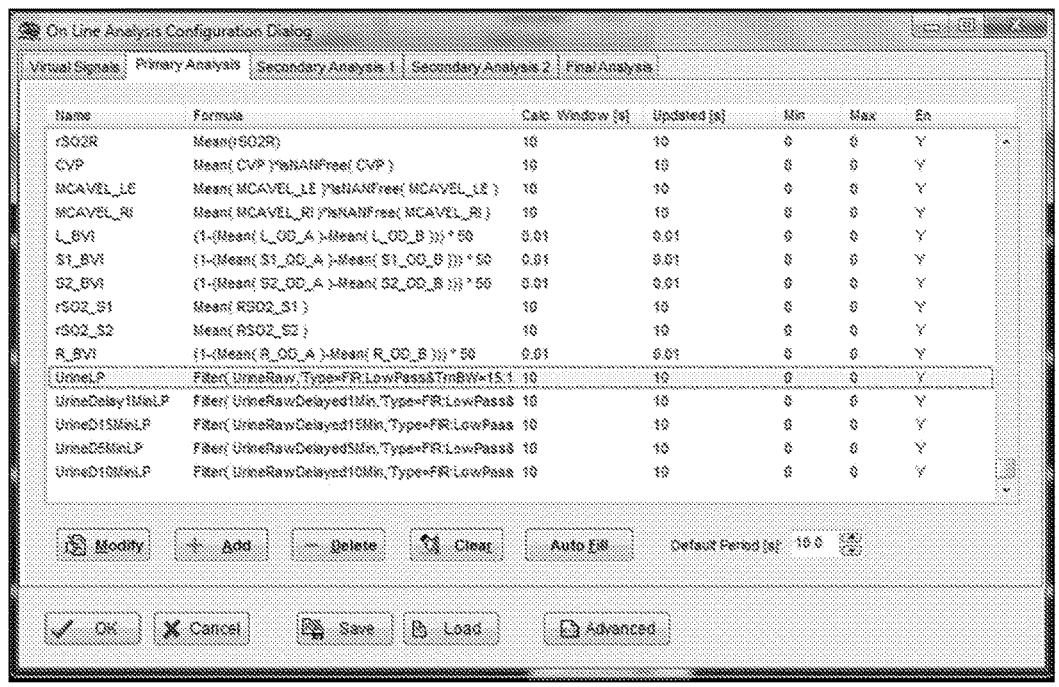
Figure 35:
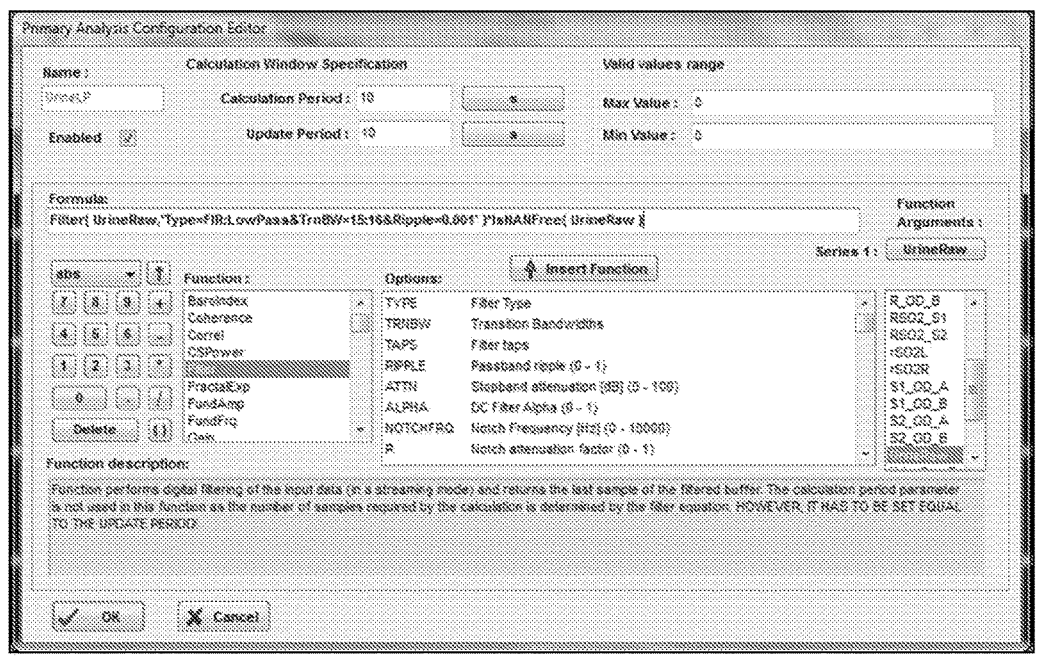
Figure 36:
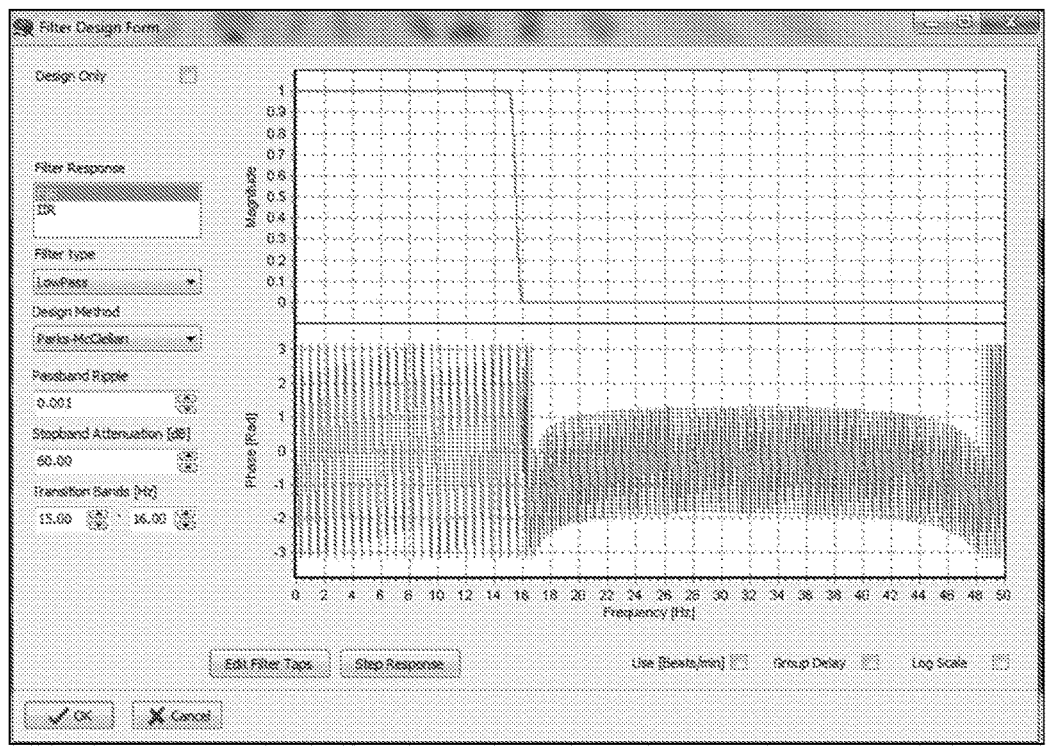

In FIG. 34, FIG. 35, and FIG. 36, AKI risk GUI 124 shows a primary analysis—Every 10 seconds, update the overall urine output. Filters applied: 16 Hz Low Pass Filter on the previous UrineRaw Virtual signal. Looking at previous 10 patients' raw data, this cutoff was experimentally found to allow the increases in urine output to pass through, both incremental as well as any inadvertent bumps into the device. A NAN filter was also applied to filter out any not-a-number readings from the weight scale (the weight scale sends an 'unstable' signal when it does not have a stable reading, i.e. very temporary bumps into the device which this should filter for).

Figure 37:
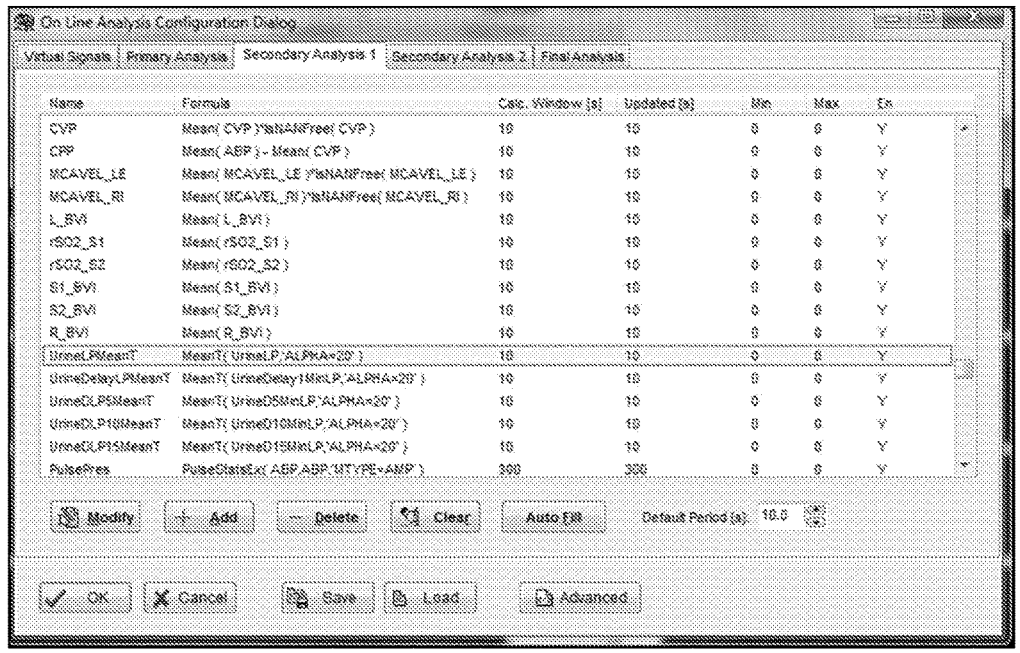
Figure 39:
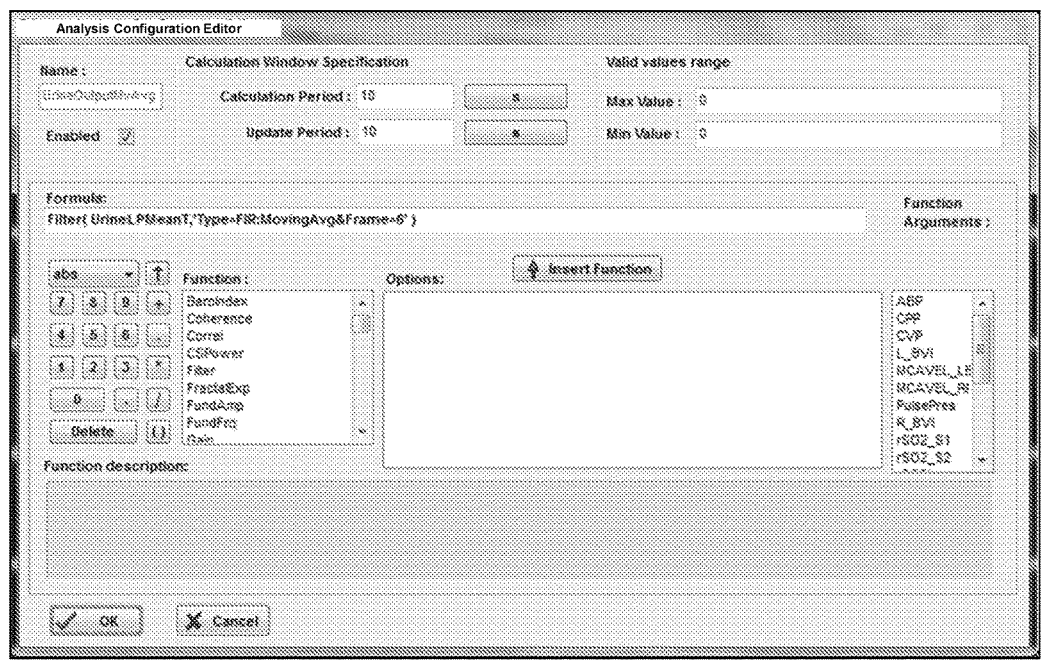
Figure 40:
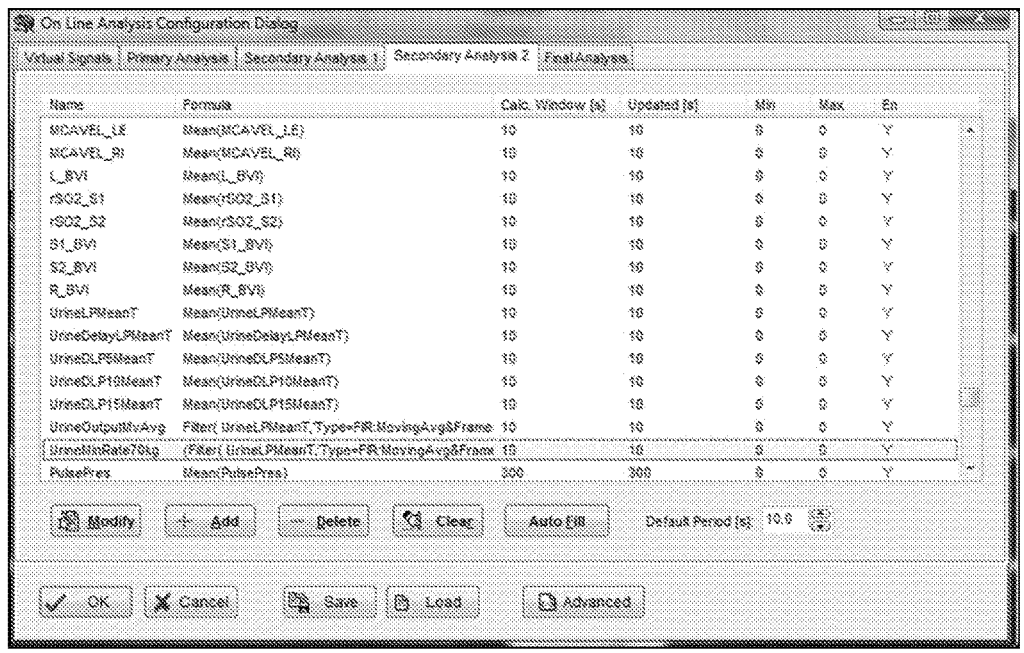
Figure 41:
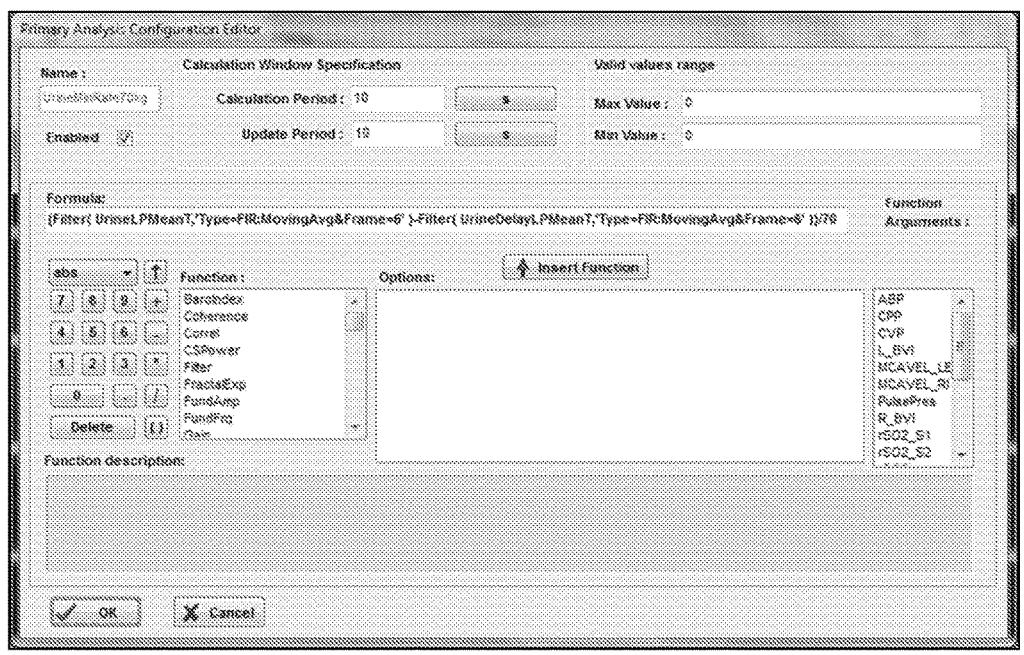

In FIG. 37, AKI risk GUI 124 shows a secondary analysis 1—Every 10 seconds, a mean threshold filter with alpha 20 (excluding top and bottom 10% of measurements) was applied. This was to further filter out any bumps which were passed through, and works to initially smooth the data every 10 seconds.

In FIG. 38, FIG. 39, FIG. 40, and FIG. 41, AKI risk GUI 124 shows a secondary analysis 2—A standard moving average filter was applied over the previous six 10 second mean values from Secondary Analysis 1 in order to give the average minute to minute urine output. In this level of analysis, another variable is made to calculate the urine output rate in the last minute in ml/kg/min by taking the current urine output and subtracting the urine output that was delayed by 1 minute. The patient kg needs to be changed here for each patient's weight going into surgery. Default is set at 70 kg as seen in the analysis configuration editor.

Figure 42:
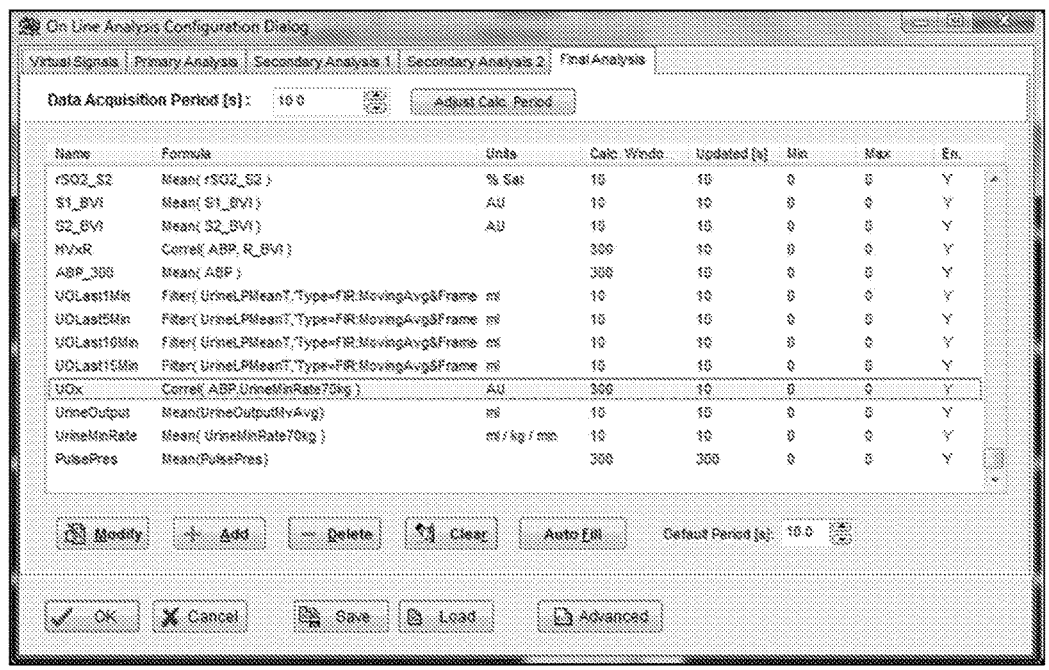
Figure 43:
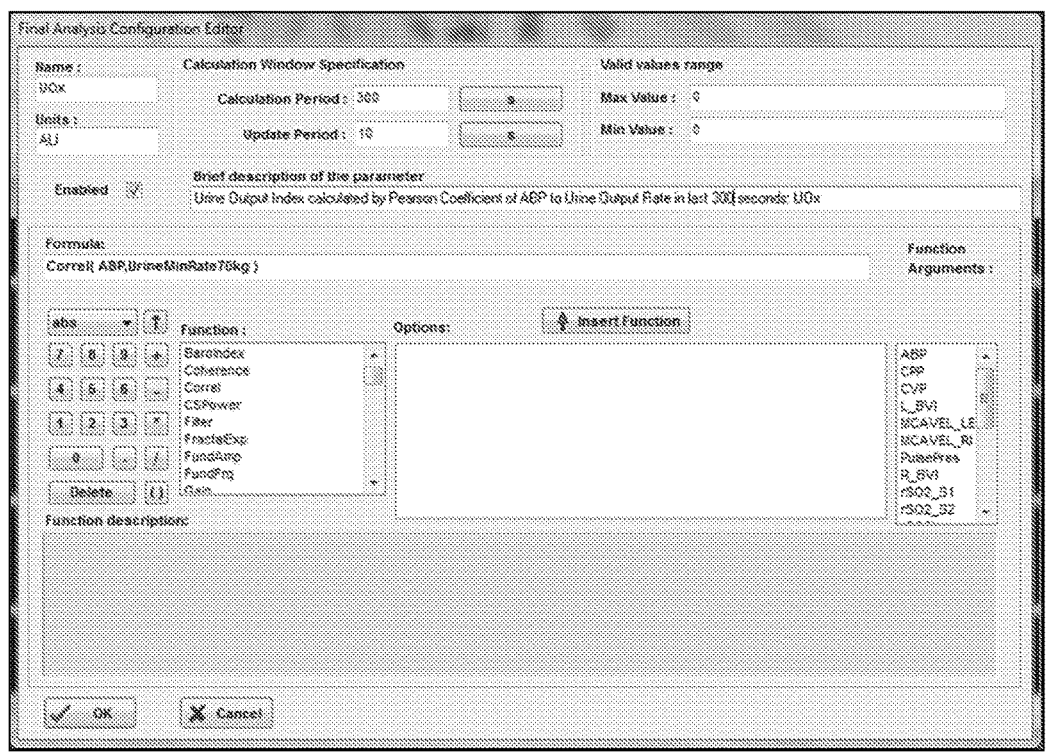

In FIG. 42 and FIG. 43, AKI risk GUI 124 shows a final analysis—Every 10 seconds UOx was calculated by taking a Pearson Correlation of the urine output rate and the ABP in the last 5 minutes—in other words, it shows time at a certain blood pressure correlated with an increase in urine output.

Figure 44:
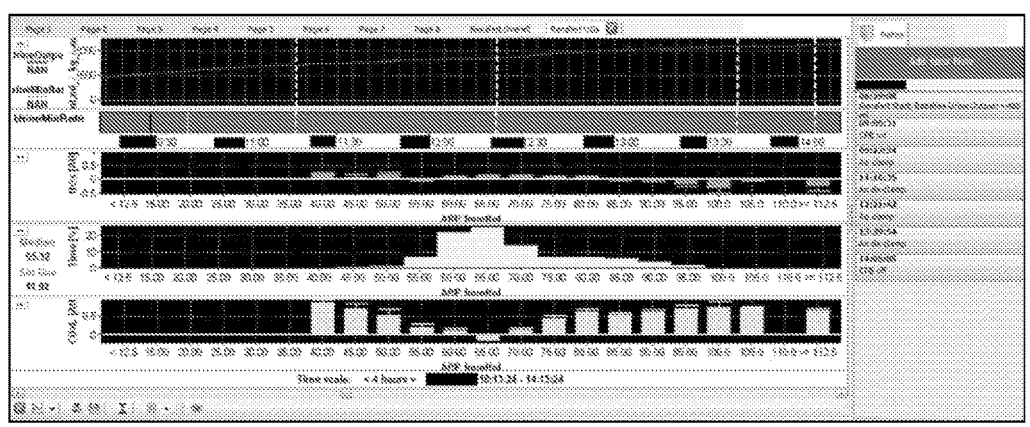

Example Use Case—As can be seen in FIG. 44, the Renalert UOx panel has urine output, urine output rate, UOx, time at each ABP (in 5 mmHg bins), and COx (Pearson correlation of cerebral oximetry to ABP). The lower limit of cerebral autoregulation can be seen to be at 55 mmHg here, and by looking at UOx, a blood pressure above 55 mmHg is slightly correlated to a positive urine output production. Thus, this example shows, in real time, the bypass period correlation shown by D. Hiori, C. Hogue, et. al that keeping ABP above the lower limit of cerebral autoregulation is correlated with improved kidney status during surgery, and subsequent rates of CSA-AKI. Since the kidney's autoregulation is determined in part due to sensed arterial blood pressure as well as ion status (i.e. chloride concentration as sensed by the macula densa cells, renin, angiotensin, aldosterone etc.), the kidney's autoregulation is linked through ABP to cerebral autoregulation, and this dashboard sets the stage for investigating real time hemodynamic and fluid management setpoints that could proactively affect kidney status during surgery.

Figures 45, 46:
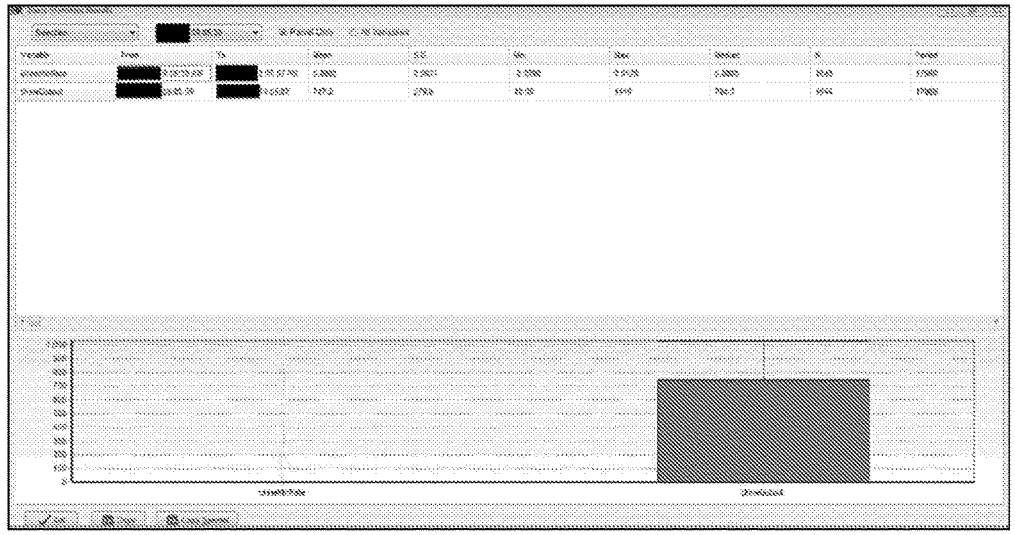

In FIG. 45, by highlighting the CPB period, summary statistics can be seen during bypass.

In FIG. 46, subsequently, urine output rates during bypass can be measured, as well as compared to perfusion sheets. Note that in this example, urine output was not recorded on the perfusion sheet initially (in many cases this measure is very approximate as well).

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A urine sensing device, the device comprising:
   (a) a weight scale comprising a platform;
   (b) a stand for positioning a urine collection vessel thereon, the stand comprising:
      (i) a base member, the base member comprising a first end, a second end, and an opening between the first end and second end;
      (ii) a first wall member extending radially from the first end of the base member, and angled at less than 90 degrees with respect to a horizontal axis of the base member, and
      (iii) a second wall member extending radially from the second end of the base member; and
   (c) an interface, for transferring the force of the stand and any contents thereon to the weight scale, positioned between the weight scale and the stand, the interface comprising:
      (i) a support member onto which the stand rests,
      (ii) a first alignment member atop the support member for interfacing with the stand via the opening, and
      (iii) a second alignment member underneath the support member for interfacing with the weight scale via the platform, wherein the first alignment member and the second alignment member are positioned such that the center of mass of the stand is aligned with respect to the center of mass of the weight scale.

2. The device of claim 1, wherein the first wall member comprises a first side aligned with a front face of the weight scale, and an opposite second side facing the second wall member, and wherein the first side of the first wall member further comprises a plurality of retaining members for securing a urinometer thereto in such a way as to prevent the urinometer from swinging from side-to-side.

3. The device of claim 1, wherein the second wall member further comprises a handle.

4. The device of claim 1, wherein the second wall member has a height that is greater than the height of the first wall member.

5. The device of claim 1, wherein the interface is constructed using a 3-D printer.

6. The device of claim 1, wherein the first alignment member comprises a protuberance that extends through the opening of the base member and securely holds the stand in place on the interface.

7. The device of claim 1, wherein the protuberance engages the base member on at least a portion of the perimeter of the opening.

8. The device of claim 1, wherein the protuberance engages the base member on the entire perimeter of the opening.

9. The device of claim 1, wherein the second alignment member comprises a groove in the support member that receives a perimeter of the platform, or wherein the second alignment member comprises a ridge on the support member that encloses perimeter of the platform.

10. The device of claim 1, wherein the urine sensing device further comprises a covering placed over the stand, the interface, and the weight scale, in such a way that at least a portion of the covering hangs over and in between the first wall member and the second wall member to create a pocket.

11. The device of claim 10, further comprising a urine collection vessel positioned in the pocket.

12. The device of claim 1, further comprising a urine collection vessel hanging from the second wall member such that it is positioned in between the first wall member and the second wall member.

13. The device of claim 12, wherein the urine collection vessel in fluid communication with a urinometer that is secured to the first wall member.

14. The device of claim 1, wherein the urine sensing device comprises a force transducer for converting the force transferred to the weight scale into to a digital output signal indicating the weight of the urine collected in the urine collection vessel.

15. The device of claim 14, further comprising a communications interface for continuously transmitting in real-time the digital output signal from the urine sensing device to a portable monitoring device for real-time and continuous monitoring of urine output, and optionally at least one intra-operative risk factor indicative of acute kidney injury.

16. The device of claim 15, wherein the portable monitoring device continuously monitors the urine output, and optionally monitors the at least one intra-operative risk factor indicative of acute kidney injury in real-time in second to second intervals or minute to minute intervals.

17. A system for real-time and continuous monitoring of kidney function, comprising:
   (a) the urine sensing device of claim 1, wherein the urine sensing device continuously monitors urine output flowing through a catheter of a catheterized patient into the urine collection vessel; and
   (b) a portable monitoring device for real-time and continuous assessment of kidney function based on a combination of real-time and continuous monitoring of urine output and volumetric flow rate based on second to second measurement of the weight of the urine collection vessel, and real-time and continuous monitoring of at least one intra-operative risk factor indicative of acute kidney injury.

18. The system of claim 17, the catheter comprises a Foley catheter.

19. The system of claim 17, further comprising an external device selected from the group consisting of an anesthesia monitor, a perfusion pump, a heart-lung machine, a cerebral oximeter, an oxygenator, a patient monitor, or any combination thereof.

20. The system of claim 19, wherein the anesthesia monitor or the patient monitor continuously monitors in real-time at least one of a mean arterial pressure of the catheterized patient, a medication administered to the catheterized patient, a fluid administered to the catheterized patient, and combinations thereof.

21. The system of claim 17, wherein the portable monitoring device comprises:
   (i) a communications interface for automatically receiving real-time urine output continuously transmitted via the communications interface of the urine sensing device, optionally real-time levels of at least one urinary component, and real-time input comprising the at least one intra-operative risk factor indicative of acute kidney injury continuously transmitted from the external device via the communications interface of (i);
   (ii) a non-transitory computer readable storage medium having computer readable program code embodied thereon for executing an acute kidney injury risk algorithm that calculates the catheterized patient's risk of developing acute kidney injury as a percentage of the likelihood that the catheterized patient will develop acute kidney injury; and (iii) a graphical user interface comprising:
(1) means for prompting a user to input pre-operative patient information, and
(2) a display for graphically displaying the percentage of the likelihood that the catheterized patient will develop acute kidney injury.

22. The system of claim 21, wherein the pre-operative patient information is selected from group the consisting of a pre-operative Society of Thoracic Surgeons Risk Factor, pre-operative baseline urine density, pre-operative patient weight, and combinations thereof.

23. The system of claim 21, wherein the display graphically displays at least one of real-time second to second urine output, real-time levels of the at least one urinary component, real-time input comprising the at least one intra-operative risk factor indicative of acute kidney injury, real-time second to second fluctuations in urine output, real-time second to second fluctuations in levels of the at least one urinary component, real-time second to second changes in the at least one intra-operative risk factor indicative of acute kidney injury, a plot of urine weight over time, an AKI risk score in the form of a percentage, alert color, literary instruction, and combinations thereof.

24. The system of claim 21, wherein the acute kidney injury risk algorithm calculates the catheterized patient's risk of developing acute kidney injury based on a weighting of acute kidney injury risk factors selected from the group consisting of the pre-operative Society of Thoracic Surgeon Risk Factors; KDIGO, RIFLE, and/or AKIN risk stratification Criteria for Urine Output; KDIGO/AKIN Criteria for Serum Creatinine; volumetric flow rate calculations based on baseline urine density, pre-operative patient weight, and real-time second to second fluctuations in weight of the urine collection vessel; real-time urine output adjusted for changes due to medication and/or fluid administered to the catheterized patient; real-time levels of the at least one urinary component adjusted for changes due to medication and/or fluid administered to the catheterized patient; and real-time input comprising changes in the at least one intra-operative risk factor indicative of acute kidney injury.

25. The system of claim 24, wherein the pre-operative Society of Thoracic Surgeon Risk Factors are selected from the group consisting of: the planned, unplanned, complicated, or unexpected nature of a Coronary Artery Bypass operation; whether or not a valve is being altered in the surgery; whether or not another cardiac procedure is indicated; if the patient is admitted with a ventricular assist device (VAD); if a VAD is implanted during current hospitalization; if an aortic procedure is to be performed; if an atrial fibrillation procedure is performed; if the current case is canceled; if there are other non-cardiac related operations; patient age, gender, height, and weight; if hemodynamic data such as ejection fraction is done; if a patient had experienced heart failure within 2 weeks; patient race, if the patient is Hispanic, Latino, or Spanish Ethnicity; if the patient is in renal failure or on dialysis; the patient's last creatinine level; the occurrence of a cardiac symptoms at time of current admission selected from the group consisting of stable angina, unstable angina, angina equivalent, non-ST Elevation myocardial infarction, ST Elevation myocardial infarction, and combinations thereof; the occurrence of a cardiac symptoms at time of surgery selected from the group consisting of stable angina, unstable angina, angina equivalent, non-ST Elevation myocardial infarction, ST Elevation myocardial infarction, and combinations thereof; if a prior myocardial infarction existed; if cardiac arrhythmia is present; if patient has chronic lung disease; if patient has cerebrovascular disease; if peripheral arterial disease is present; if patient has diabetes; if hypertension is present; whether or not the patient is immunocompromised; if endocarditis is present; if coronary disease exists; the nature of the surgery; if the patient has been resuscitated within one hour of the start of the procedure; if the patient has been resuscitated between 1 and 24 hours from the start of the procedure; if the patient is experiencing cardiogenic shock; if patient has an intra-aortic balloon pump installed; if patient is on inotropes; if patient has had a previous cardiac intervention; if mitral valve or aortic disease is present, the degree of mitral valve insufficiency, the degree of tricuspid insufficiency; the degree of aortic insufficiency, and the incidence of current cardiovascular surgery, and combinations thereof.

26. The system of claim 24, wherein the KDIGO Criteria for Urine Output is selected from the group consisting of stratification of acute kidney injury in increasing severity stages wherein said stages are defined as the following: stage 1 is defined as <0.5 ml/kg/h for 6-12 hours, stage 2 is defined as <0.5 ml/kg/h for >12 hours, and stage three is defined as <0.3 ml/kg/h for more than 24 hours, or anuria for more than 12 hours, and combinations thereof, and/or wherein the KDIGO/AKIN Criteria for Serum Creatinine is selected from the group consisting of stratification of acute kidney injury in increasing severity stages wherein said stages are defined as the following: stage 1 is defined as a 50%-99% increase in serum creatinine from baseline, or an acute increase of 0.3 mg/dL or more from baseline, stage 2 is defined as a 100%-199% increase in serum creatinine from baseline, and stage 3 is defined as a 200% or greater increase in serum creatinine from baseline, or any new need for hemodialysis.

27. The system of claim 24, wherein the at least one urinary component is selected from the group consisting of urine sodium levels, urine oxygen tension levels, urine creatinine levels, urine potassium levels, and urine chloride levels.

28. The system of claim 22, wherein the at least one intra-operative risk factor indicative of acute kidney injury is selected from the group consisting of a real-time cerebral oximetry autoregulation threshold, nadir oxygen delivery, oxygen tension, mean arterial blood pressure, vasopressor dosage, diuretic delivery, fluid delivery, and combinations thereof.

29. The system of claim 17, wherein the acute kidney injury risk algorithm comprises a self-learning algorithm that adjusts the weighting of the acute kidney injury risk factors for each catheterized patient based on the relative significance of the acute kidney injury risk factors toward influencing outcomes of other catheterized patients presenting with similar acute kidney injury risk factors.

30. The system of claim 17, further comprising a patient database in electronic communication with the portable monitoring device, wherein the patient database comprises for each catheterized patient, the calculation of the patient's acute kidney injury risk, the acute kidney injury risk factors present in the patient, the weighting of the patient's acute kidney injury risk factors, and an indication of whether the patient developed acute kidney injury.

31. The system of claim 17, further comprising a function for filtering the digital output signal.

32. A method for real-time assessment of a patient's risk of developing acute kidney injury, the method comprising:

(a) connecting a catheter of a catheterized patient to a urine collection vessel positioned on a urine sensing device of claim 1, wherein the urine sensing device measures second-to-second urine output;

(b) continuously monitoring urine output of said catheterized patient by measuring real-time second to second fluctuations in urine output with the urine sensing device;

(c) transmitting the continuously monitored real-time fluctuations in urine output measured in (b) to a patient monitoring device, wherein the patient monitoring device comprises:

(i) a communications interface for automatically receiving the continuously monitored real-time fluctuations transmitted in (c);

(ii) a non-transitory computer readable storage medium having computer readable program code embodied thereon for executing an acute kidney injury risk algorithm that calculates the catheterized patient's risk of developing acute kidney injury as a percentage of the likelihood that the catheterized patient will develop acute kidney injury; and (iii) a graphical user interface comprising means for prompting a user to input pre-operative patient information;

(e) calculating the catheterized patient's risk of developing acute kidney injury as a percentage of the likelihood that the catheterized patient will develop acute kidney injury; and (f) displaying through the graphical user interface the catheterized patient's risk of developing acute kidney injury as a percentage of the likelihood that the catheterized patient will develop acute kidney injury.

33. The method of claim 32, further comprising continuously transmitting via a communications interface the digital output signal from the urine sensing device to the portable monitoring device.

34. The method of claim 32, further comprising continuously monitoring at least one intra-operative risk factor indicative of acute kidney injury by measuring real-time second to second changes in the at least one intra-operative risk factor indicative of acute kidney injury using an external device.

35. The method of claim 34, wherein the external device is selected from the group consisting of an anesthesia monitor, a perfusion pump, a heart-lung machine, a cerebral oximeter, an oxygenator, a patient monitor, and combinations thereof.

36. The method of claim 34, further comprising automatically receiving, via the communications interface, the measured real-time second to second changes in the at least one intra-operative risk factor indicative of acute kidney injury.

37. The method of claim 32, wherein the pre-operative patient information is selected from group the consisting of a pre-operative Society of Thoracic Surgeons Risk Factor, pre-operative baseline urine density, pre-operative patient weight, and combinations thereof.

38. The method of claim 32, further comprising displaying at least one of real-time second to second urine output, real-time levels of the at least one urinary component, real-time input comprising the at least one intra-operative risk factor indicative of acute kidney injury, real-time second to second fluctuations in urine output, real-time second to second fluctuations in levels of the at least one urinary component, real-time second to second changes in the at least one intra-operative risk factor indicative of acute kidney injury, a plot of urine weight over time, an AKI risk score in the form of a numerical percentage, alert color, or literary instruction, and combinations thereof.

39. The method of claim 32, wherein the acute kidney injury risk algorithm calculates the catheterized patient's risk of developing acute kidney injury based on a weighting of acute kidney injury risk factors selected from the group consisting of the pre-operative Society of Thoracic Surgeon Risk Factors; KDIGO Criteria for Urine Output; KDIGO/AKIN Criteria for Serum Creatinine; volumetric flow rate calculations based on baseline urine density, pre-operative patient weight, and real-time second to second fluctuations in weight of the urine collection vessel; real-time urine output adjusted for changes due to medication and/or fluid administered to the catheterized patient; optionally real-time levels of the at least one urinary component adjusted for changes due to medication and/or fluid administered to the catheterized patient; and real-time changes in the at least one intra-operative risk factor indicative of acute kidney injury.

40. The method of claim 39, wherein the pre-operative Society of Thoracic Surgeon Risk Factors are selected from the group consisting of: the planned, unplanned, complicated, or unexpected nature of a Coronary Artery Bypass operation; whether or not a valve is being altered in the surgery; whether or not another cardiac procedure is indicated; if the patient is admitted with a ventricular assist device (VAD); if a VAD is implanted during current hospitalization; if an aortic procedure is to be performed; if an atrial fibrillation procedure is performed; if the current case is canceled; if there are other non-cardiac related operations; patient age, gender, height, and weight; if hemodynamic data such as ejection fraction is done; if a patient had experienced heart failure within 2 weeks; patient race, if the patient is Hispanic, Latino, or Spanish Ethnicity; if the patient is in renal failure or on dialysis; the patient's last creatinine level; the occurrence of a cardiac symptoms at time of current admission selected from the group consisting of stable angina, unstable angina, angina equivalent, non-ST Elevation myocardial infarction, ST Elevation myocardial infarction, and combinations thereof; the occurrence of a cardiac symptoms at time of surgery selected from the group consisting of stable angina, unstable angina, angina equivalent, non-ST Elevation myocardial infarction, ST Elevation myocardial infarction, and combinations thereof; if a prior myocardial infarction existed; if cardiac arrhythmia is present; if patient has chronic lung disease; if patient has cerebrovascular disease; if peripheral arterial disease is present; if patient has diabetes; if hypertension is present; whether or not the patient is immunocompromised; if endocarditis is present; if coronary disease exists; the nature of the surgery; if the patient has been resuscitated within one hour of the start of the procedure; if the patient has been resuscitated between 1 and 24 hours from the start of the procedure; if the patient is experiencing cardiogenic shock; if patient has an intra-aortic balloon pump installed; if patient is on inotropes; if patient has had a previous cardiac intervention; if mitral valve or aortic disease is present, the degree of mitral valve insufficiency, the degree of tricuspid insufficiency; the degree of aortic insufficiency, and the incidence of current cardiovascular surgery, and combinations thereof.

41. The method of claim 39, wherein the KDIGO Criteria for Urine Output is selected from the group consisting of stratification of acute kidney injury in increasing severity stages wherein said stages are defined as the following: stage 1 is defined as <0.5 ml/kg/h for 6-12 hours, stage 2 is defined as <0.5 ml/kg/h for >12 hours, and stage three is defined as <0.3 ml/kg/h for more than 24 hours, or anuria for more than 12 hours, and combinations thereof, and/or wherein the KDIGO/AKIN Criteria for Serum Creatinine is selected from the group consisting of stratification of acute kidney injury in increasing severity stages wherein said stages are defined as the following: stage 1 is defined as a 50%-99% increase in serum creatinine from baseline, or an acute increase of 0.3 mg/dL or more from baseline, stage 2 is defined as a 100%-199% increase in serum creatinine from baseline, and stage 3 is defined as a 200% or greater increase in serum creatinine from baseline, or any new need for hemodialysis.

42. The method of claim 39, wherein the at least one urinary component is selected from the group consisting of urine sodium levels, urine oxygen tension levels, urine creatinine levels, urine potassium levels, and urine chloride levels.

43. The method of claim 36, wherein the at least one intra-operative risk factor indicative of acute kidney injury is selected from the group consisting of a real-time cerebral oximetry autoregulation threshold, nadir oxygen delivery, oxygen tension, mean arterial blood pressure, and combinations thereof.

44. The method of claim 32, adjusting the weighting of the acute kidney injury risk factors for each catheterized patient via the acute kidney injury risk algorithm based on the relative significance of the acute kidney injury risk factors toward influencing outcomes of other catheterized patients presenting with similar acute kidney injury risk factors.

45. The method of claim 32, further comprising storing in a patient database in communication with the portable monitoring device, for each catheterized patient, the calculation of the patient's acute kidney injury risk, the acute kidney injury risk factors for the patient, the weighting of the patient's acute kidney injury risk factors, and an indication of whether the patient developed acute kidney injury.

* * * * *